United States Patent
Duignan et al.

(10) Patent No.: US 9,750,902 B2
(45) Date of Patent: Sep. 5, 2017

(54) DISPENSER

(71) Applicant: EURO-CELTIQUE S.A., Luxembourg (LU)

(72) Inventors: Cathal Duignan, Leitrim (IE); Iain Grierson McDerment, Hertfordshire (GB); Peter Prior, Roscommon (IE)

(73) Assignee: EURO-CELTIQUE S.A., Luxembourg (LU)

( * ) Notice: Subject to any disclaimer, the term of this patent is extended or adjusted under 35 U.S.C. 154(b) by 122 days.

(21) Appl. No.: 14/776,991

(22) PCT Filed: Mar. 10, 2014

(86) PCT No.: PCT/EP2014/054523
§ 371 (c)(1),
(2) Date: Sep. 15, 2015

(87) PCT Pub. No.: WO2014/139912
PCT Pub. Date: Sep. 18, 2014

(65) Prior Publication Data
US 2016/0038696 A1 Feb. 11, 2016

(30) Foreign Application Priority Data
Mar. 15, 2013 (GB) .................................. 1304784.0

(51) Int. Cl.
*A61M 15/00* (2006.01)
*A61M 16/12* (2006.01)
(Continued)

(52) U.S. Cl.
CPC ...... *A61M 15/0073* (2014.02); *A61M 15/009* (2013.01); *A61M 15/0026* (2014.02);
(Continued)

(58) Field of Classification Search
None
See application file for complete search history.

(56) References Cited

U.S. PATENT DOCUMENTS 3,380,610 A * 4/1968 Krieps ............... B65D 43/0218
215/320
3,742,898 A * 7/1973 Souza .................... B65D 39/04
116/268

(Continued)

FOREIGN PATENT DOCUMENTS

WO  WO 2004/073776 A1   9/2004
WO  WO2010/103315        9/2010
(Continued)

OTHER PUBLICATIONS

International Preliminary Report on Patentability dated Sep. 15, 2015 and Written Opinion, issued in connection with PCT/EP2014/054523.

(Continued)

*Primary Examiner* — Tan-Uyen (Jackie) T Ho
*Assistant Examiner* — Joseph D Boecker
(74) *Attorney, Agent, or Firm* — Nixon & Vanderhye P.C.

(57) ABSTRACT

The present invention relates to dispensers, in particular to dispensers for dispensing a dose of a gaseous, gas borne or droplet substance from a substance source and dispensers comprising dosage counters. The present invention therefore provides a dispenser for dispensing a dose of a gaseous, gas borne or droplet substance from a substance source, the dispenser comprising: a body (1) for receiving a substance source, the body having a mouthpiece (2); a junction member (41) slideably arranged in the body for movement in a longitudinal axis of the body to release a dose of a substance from a substance source (C), the junction member receiving (Continued)

a spout (S) of a substance source in a socket (43); and a dispenser driver for moving the junction member in the longitudinal axis of the body to release a dose of a substance from a substance source. A cam follower (16) is slideably arranged within the body having rigid protrusions (18*a*, 18*b*) projecting from a base (17) and the protrusion being arranged between the dispenser driver and the junction member such that a force applied by the cam of the dispenser driver to the protrusion causes the cam follower to slideably move in the longitudinal axis of the body and apply a force to the junction member so as to release a dose of a substance from a substance source. The dispenser also comprises a dispenser cap (91) comprising a hollow body having a lower open end (92) engageable with the body, and an upper open end (94) for receiving a cap closure device (120) for closing the upper open end. The dispenser also comprises a dose counter (203) for indicating a number of actuations of the dispenser corresponding to a number of doses dispensed from a substance source, or a number of doses remaining in a substance source, the dose counter comprising: a first ring member (202) having a first indicia and being rotatable in increments about the longitudinal axis, the first indicia indicating a count; and a limiting member comprising a limiting mechanism (1506), wherein the limiting mechanism comprises an engaging portion arranged to act radially with respect to the first ring member to contact the first ring member to limit free rotation of the first member relative to the limiting member about the axis.

59 Claims, 31 Drawing Sheets

(51) Int. Cl.
*A61M 16/14* (2006.01)
*A61M 16/20* (2006.01)
*G06M 1/14* (2006.01)

(52) U.S. Cl.
CPC ........ *A61M 15/0091* (2013.01); *A61M 16/12* (2013.01); *A61M 16/14* (2013.01); *A61M 16/20* (2013.01); *G06M 1/143* (2013.01); *A61M 15/0093* (2014.02)

(56) References Cited

U.S. PATENT DOCUMENTS

| | | | |
|---|---|---|---|
| 5,060,643 A | 10/1991 | Rich et al. | |
| 5,447,150 A * | 9/1995 | Bacon | A61M 15/0091 128/200.14 |
| 6,179,139 B1 * | 1/2001 | Heilman | B65D 55/026 215/230 |
| 6,283,365 B1 * | 9/2001 | Bason | G06M 1/041 235/116 |
| 6,701,917 B2 * | 3/2004 | O'Leary | A61M 15/0045 128/200.14 |
| 7,721,731 B2 | 5/2010 | Bacon | |
| 9,572,945 B2 * | 2/2017 | Duignan | A61M 15/009 |
| 2003/0178021 A1 * | 9/2003 | Rasmussen | A61M 15/0096 128/200.23 |
| 2004/0069301 A1 | 4/2004 | Bacon | |
| 2005/0081846 A1 | 4/2005 | Barney | |
| 2006/0150971 A1 * | 7/2006 | Lee | A61M 15/009 128/203.15 |
| 2007/0062522 A1 * | 3/2007 | Bacon | A61M 15/0095 128/200.23 |
| 2007/0187353 A1 * | 8/2007 | Fox | B01L 3/50825 215/354 |
| 2008/0105253 A1 | 5/2008 | Pearson et al. | |
| 2008/0178872 A1 * | 7/2008 | Genova | A61M 15/0065 128/200.23 |
| 2009/0139516 A1 * | 6/2009 | Augustyn | A61M 15/0045 128/200.23 |
| 2010/0012115 A1 * | 1/2010 | Bacon | A61M 15/0065 128/200.23 |
| 2010/0192946 A1 * | 8/2010 | Oi | A61M 15/009 128/200.23 |
| 2012/0111323 A1 * | 5/2012 | Bacon | A61M 15/0065 128/203.12 |
| 2014/0290648 A1 * | 10/2014 | Duignan | A61M 15/009 128/200.23 |
| 2014/0311484 A1 * | 10/2014 | Duignan | A61M 15/009 128/200.23 |
| 2015/0347894 A1 * | 12/2015 | Duignan | G06M 1/163 128/203.12 |

FOREIGN PATENT DOCUMENTS

| | | |
|---|---|---|
| WO | WO2013/064820 | 5/2013 |
| WO | WO2013/064821 | 5/2013 |

OTHER PUBLICATIONS

International Search Report dated May 13, 2014, issued in connection with PCT/EP2014/054523.
EPO Machine English translation of FR1082285 (RICAL SA "Plastic seal material for sealing bottles and other containers" Dec. 28, 1954).
Office Action dated May 22, 2017 received in U.S. Appl. No. 14/797,318 (Bacon; Title: Counter; filed Jul. 13, 2015).

\* cited by examiner

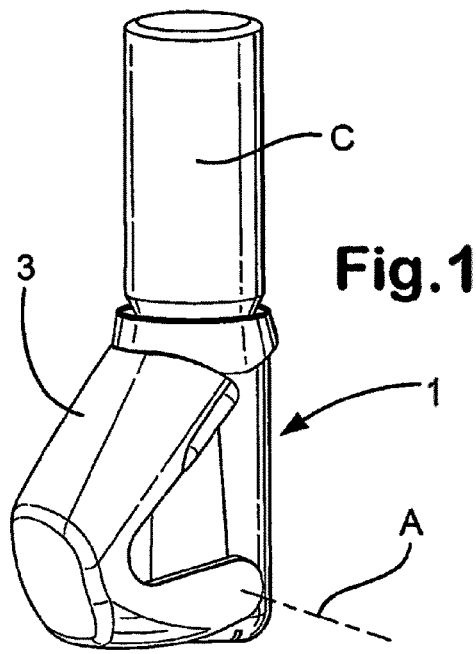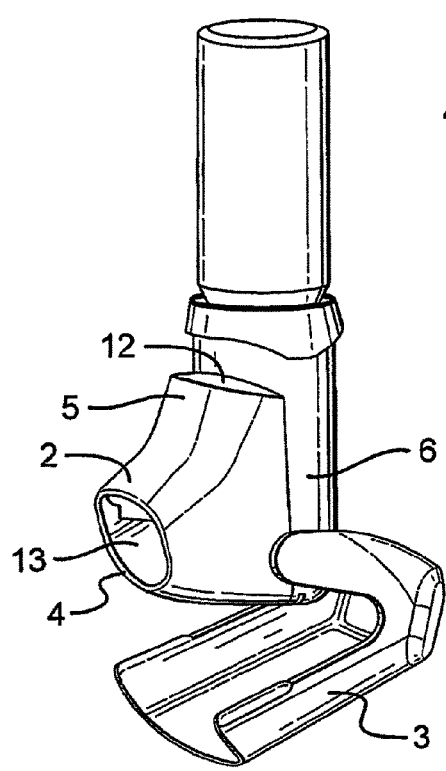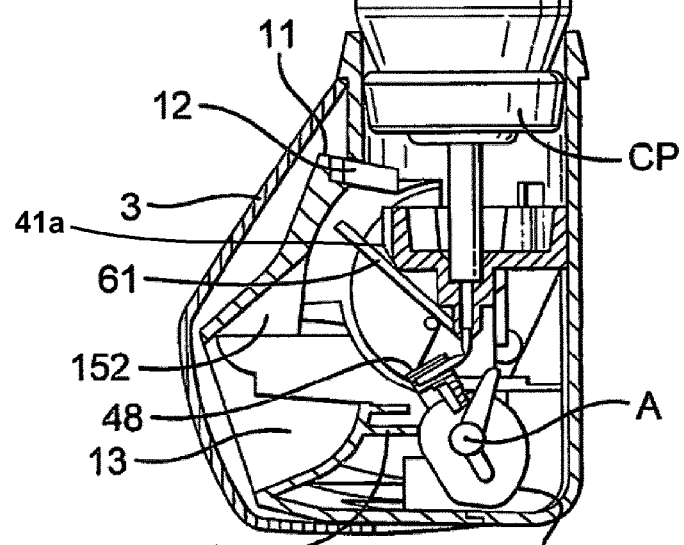

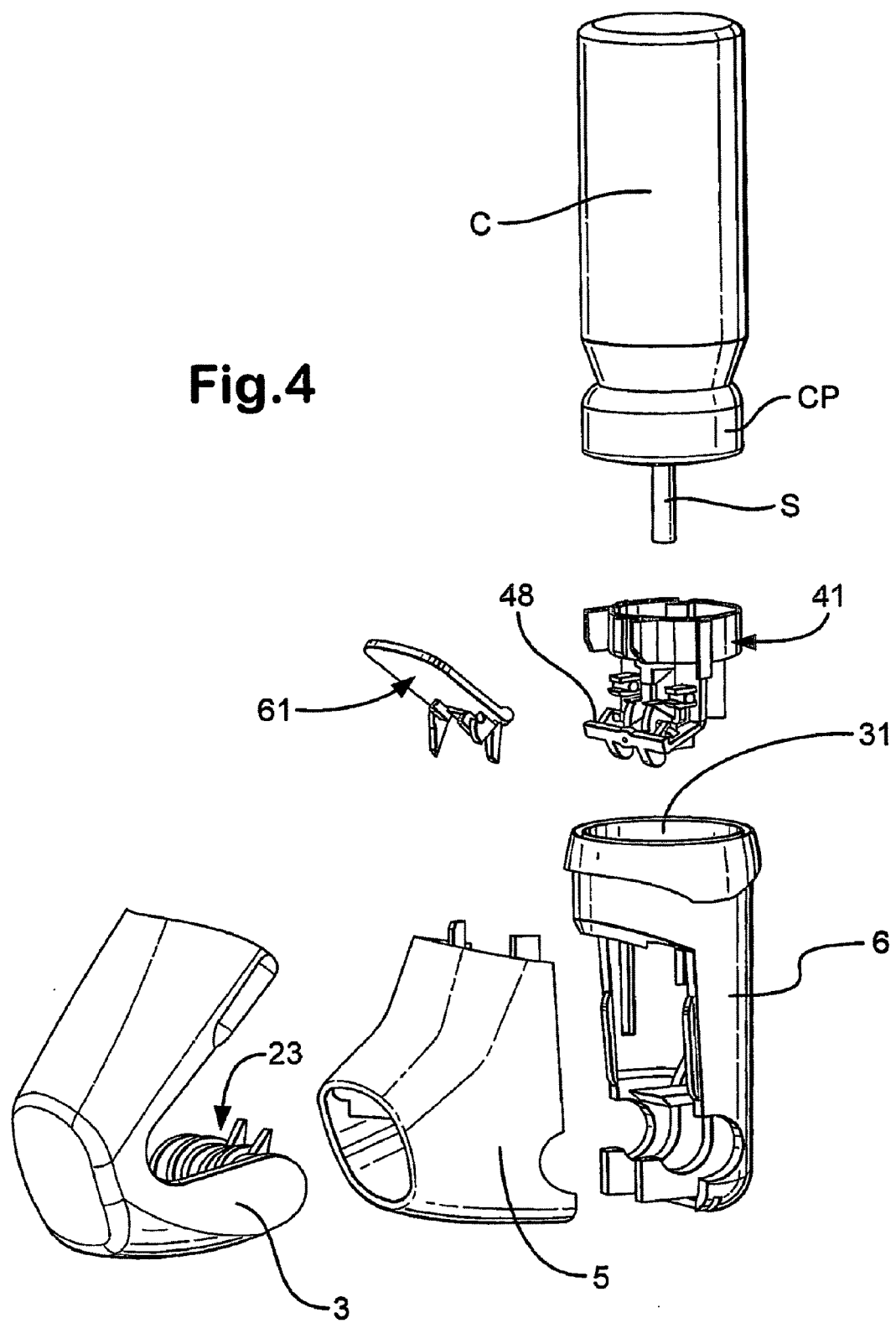

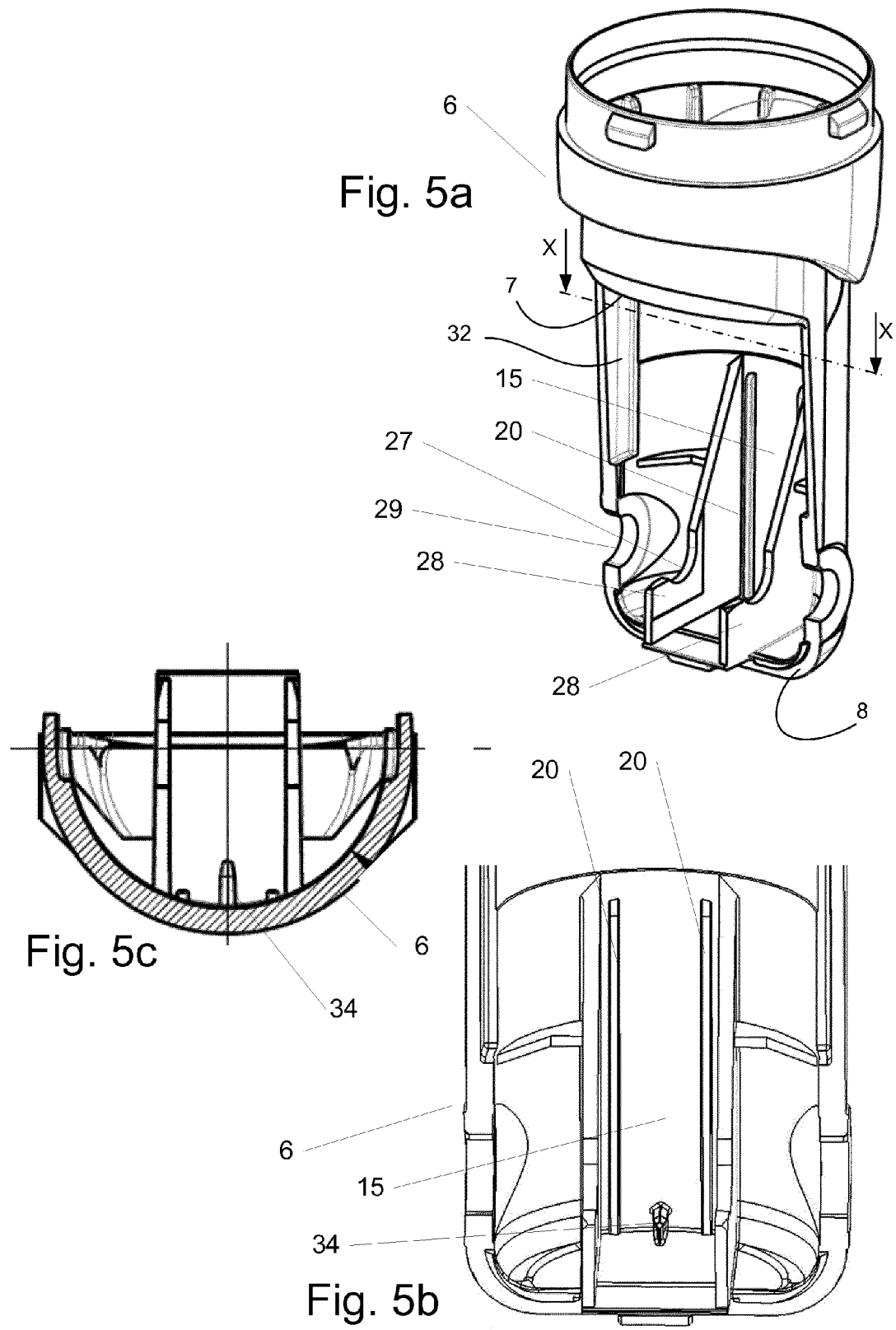

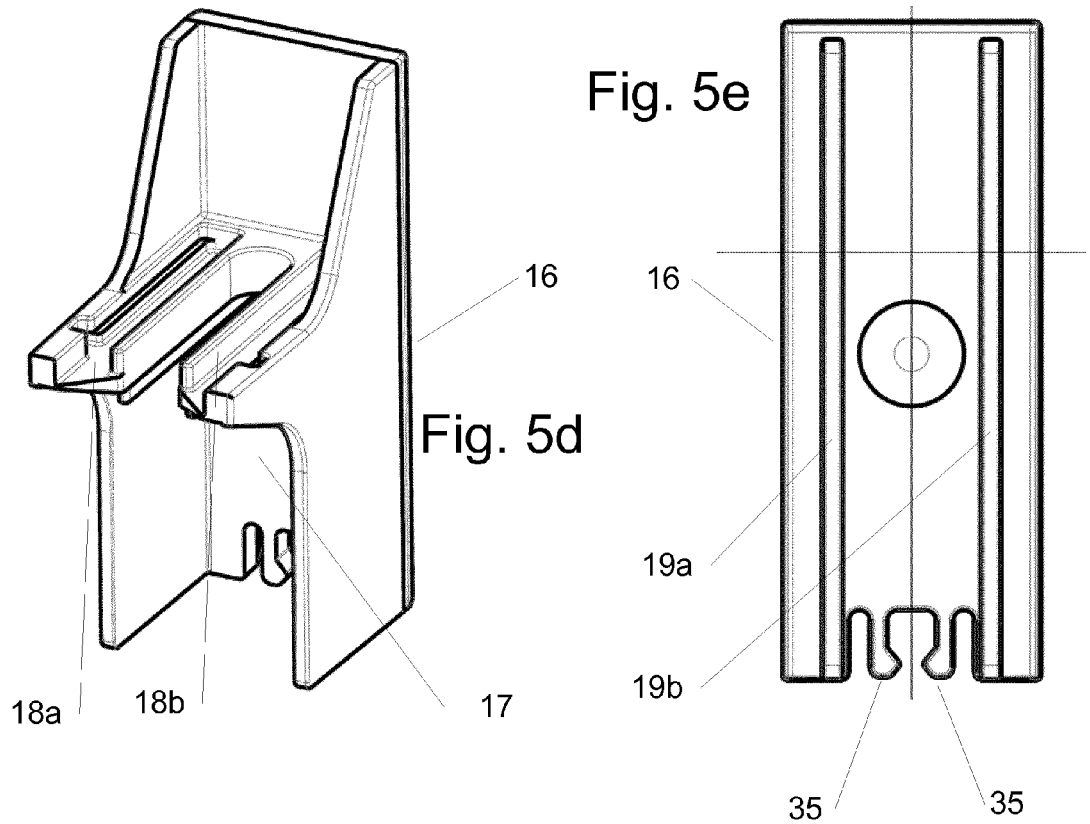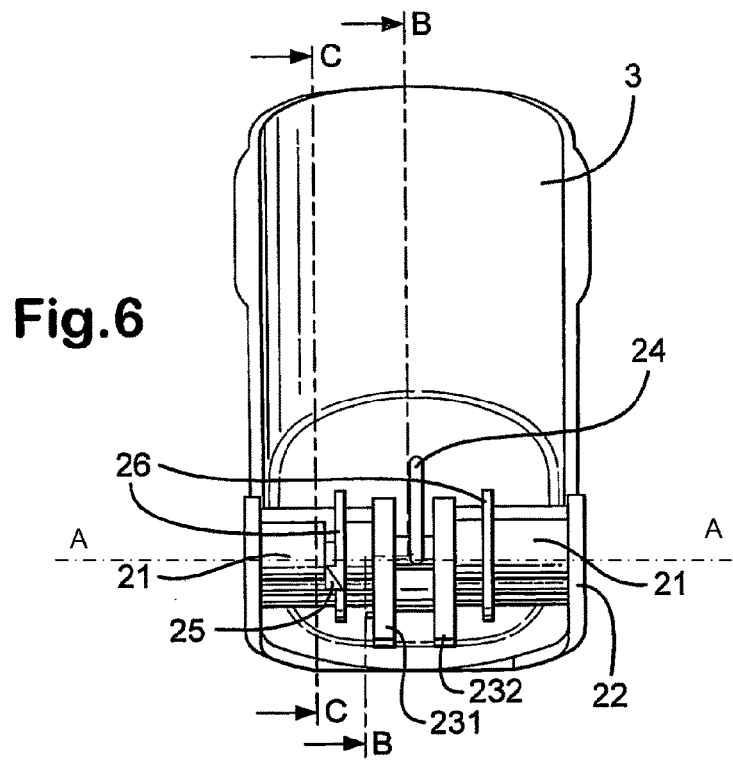

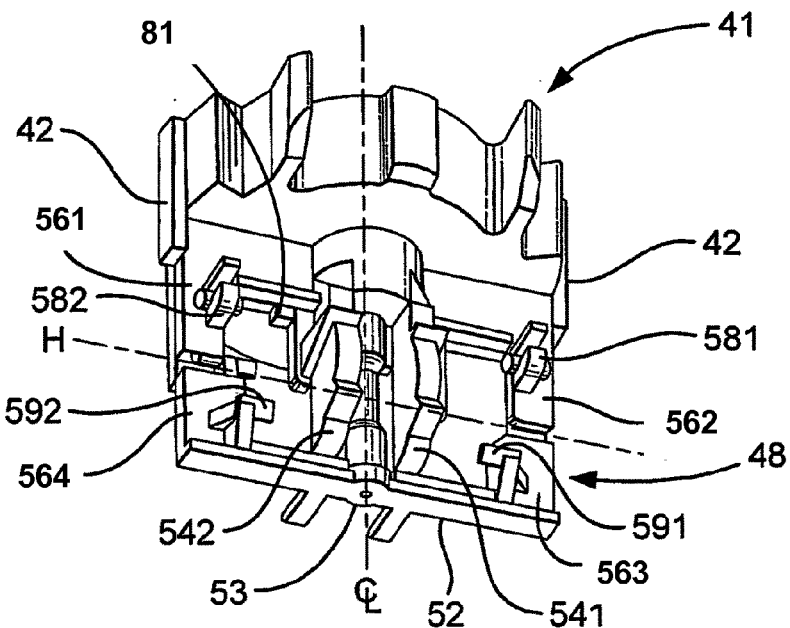
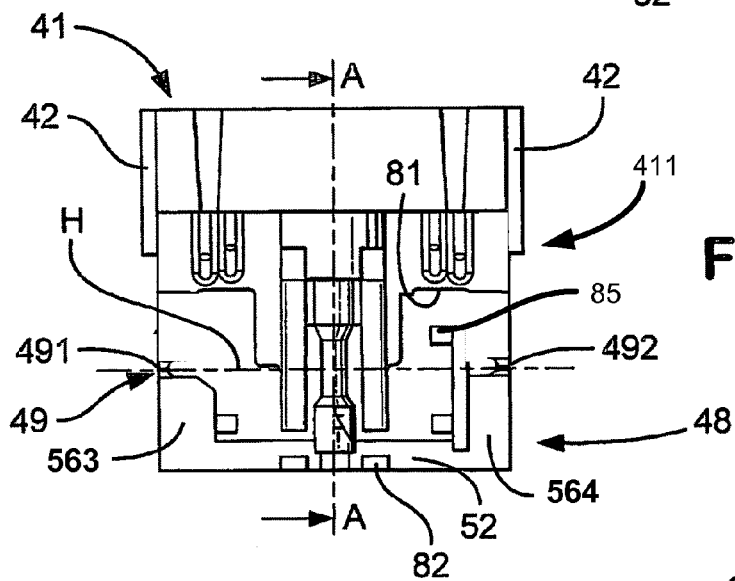
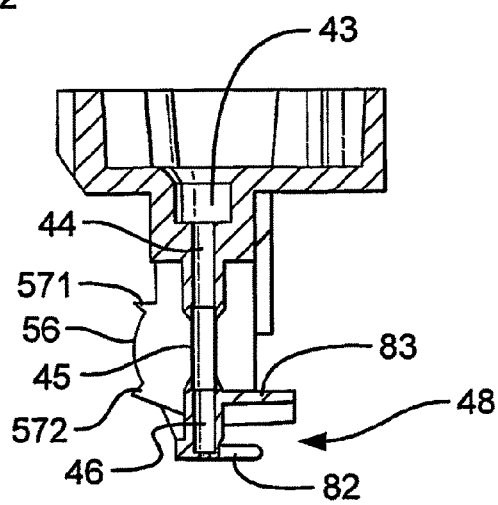

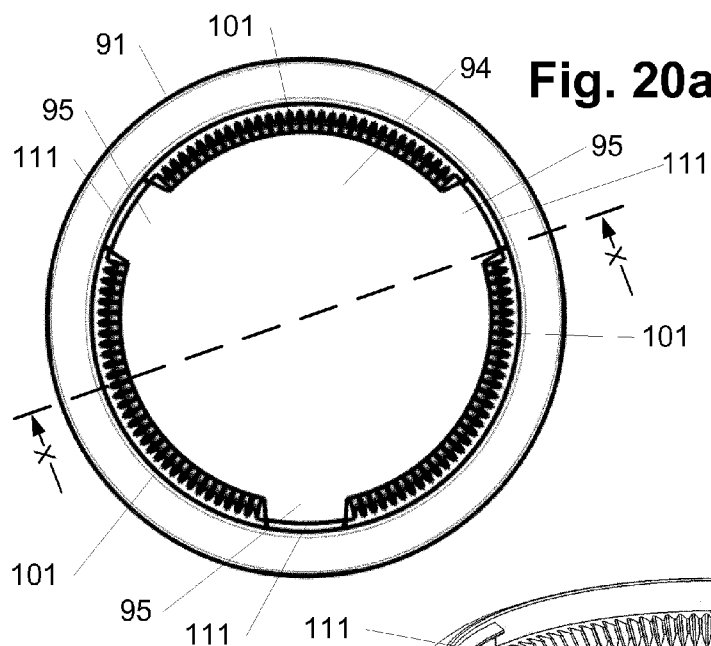
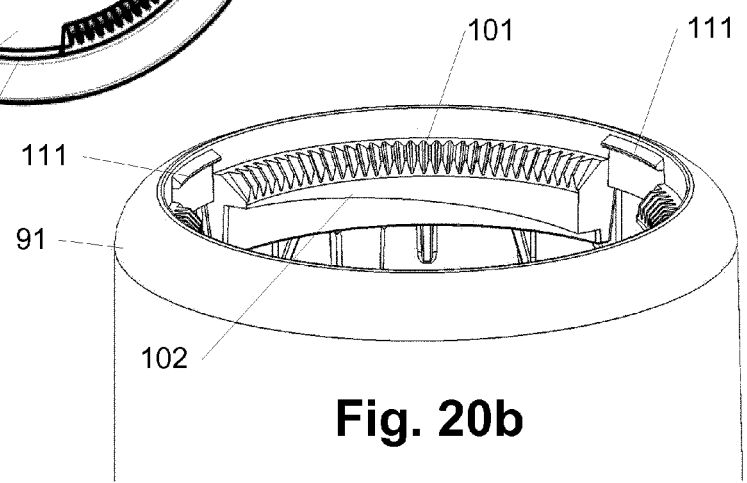
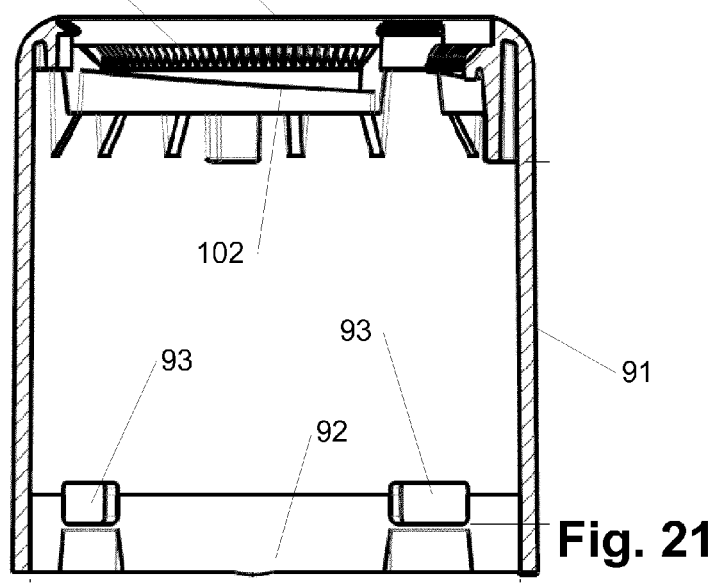

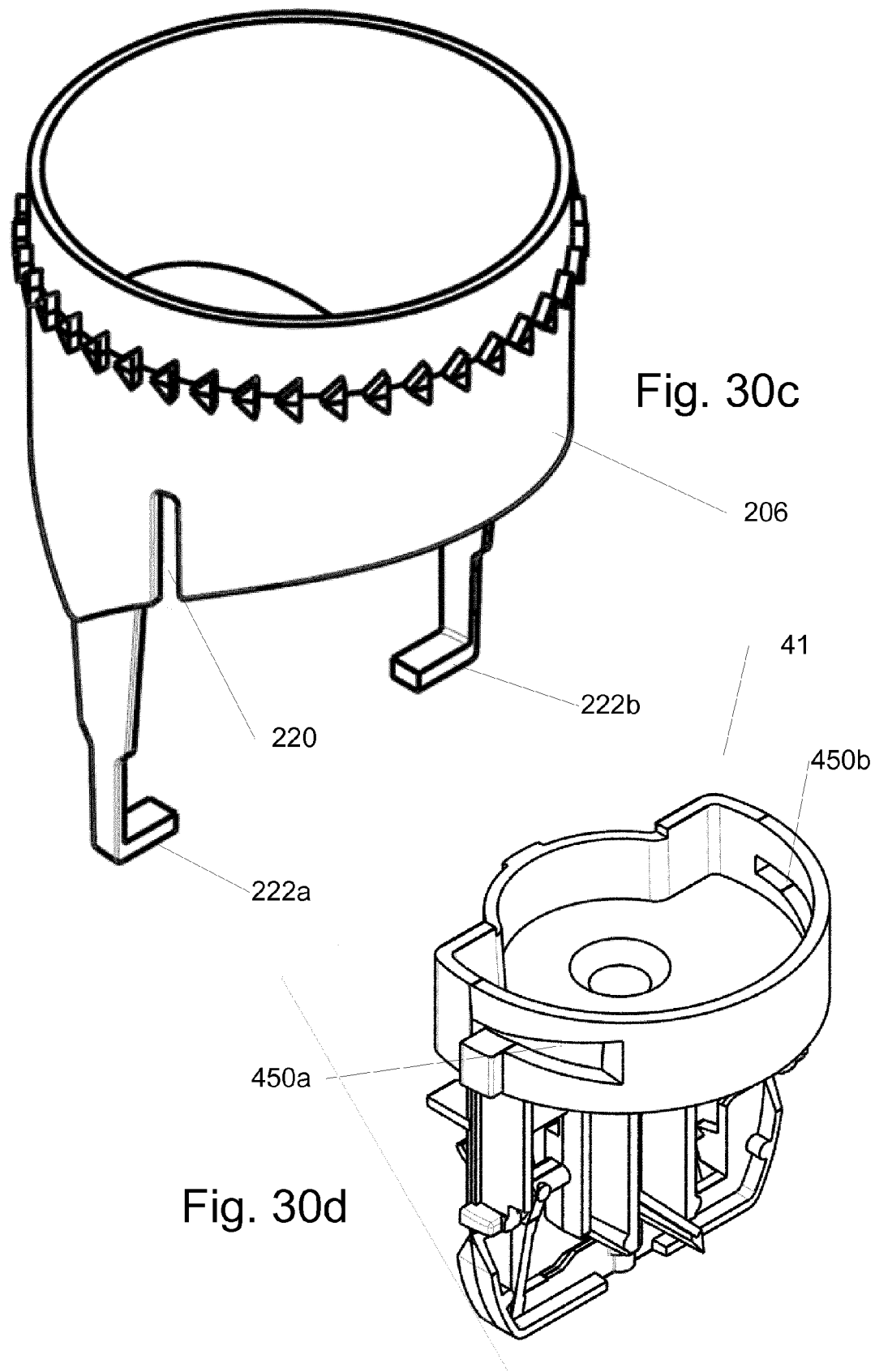

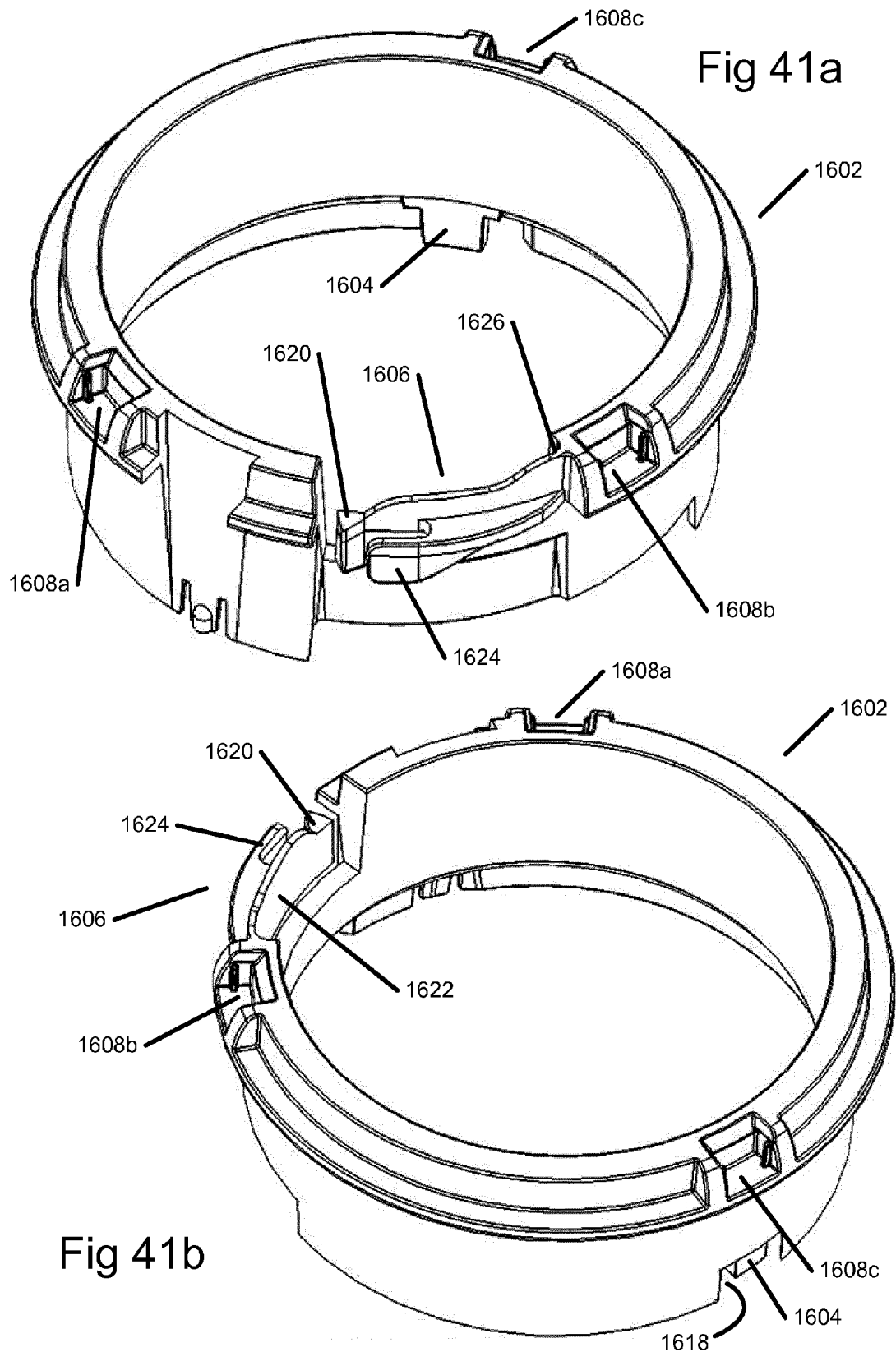

DISPENSER

This application is the U.S. national phase of International Application No. PCT/EP2014/054523 filed 10 Mar. 2014 which designated the U.S. and claims priority to GB Patent Application No. 1304784.0 filed 15 Mar. 2013, the entire contents of each of which are hereby incorporated by reference.

FIELD OF THE INVENTION

The present invention relates to dispensers, in particular to dispensers for dispensing a dose of a gaseous, gas borne or droplet substance from a substance source and dispensers comprising dosage counters.

BACKGROUND OF THE INVENTION

In general, metered-dose inhalers (MDIs) are devices for dispensing medicaments, e.g. in aerosol form, to the lungs. Broadly speaking dispensers such as MDIs are comprised of two components: a container and a delivery device. The container holds the medication, e.g. dissolved or suspended in a propellant under high pressure to maintain a liquid phase. Additionally the container often comprises an internal metering valve, which is designed to release a precisely measured, reproducible dose of medicament when the valve is actuated. The delivery device typically includes an actuator and a mouthpiece. The actuator, which can be triggered by the user, for example by inhalation or manual operation, typically interacts with the metering valve of the container to induce release of a dose. The mouthpiece serves to direct the medication towards the user.

We have previously described a number of dispensers, see for example U.S. Pat. No. 7,721,731 and WO 2013/064821. We have also described a dispenser cap arrangement, see WO 2013/064820. We have also disclosed dosage counters for use with such dispensers, see for example WO 2010/103315. Further examples of dose counters and dispensers may be found in WO2005/060535, GB2372542 and US2011/259324.

As medicament containers are typically made of an opaque material such as aluminium, and may be housed entirely within a delivery device, it is generally not possible for a user to gauge effectively how many doses of medicament remain therein. This may result in a user prematurely discarding a MDI still containing doses of medicament or worse using the MDI beyond its recommended lifetime. Neither situation is desirable—the former is wasteful while the latter is potentially dangerous. Users sometimes shake MDIs to try to obtain a measure of whether any medicament is present therein, but this only provides a very crude qualitative measure of the container contents. It would not, for example, enable a user to distinguish between a container comprising enough medicament and propellant to form a dose and one comprising a quantity of medicament and propellant that is less than that needed to fill the metering valve. In other words, there is a risk that users overestimate the amount of medicament present in a container and mistakenly conclude that there is sufficient medicament remaining for another dose when in fact there is not. Additionally a user may not be provided with sufficient warning to obtain a replacement medicament container prior to the one in use running out.

It is therefore desirable to provide dispensers, e.g. inhalers, with a counter mechanism that enables a user to track how many doses have been dispensed therefrom and, complementarily, how many doses remain. Indeed, regulatory bodies such as the Food and Drug Administration (FDA) of the United States and the European Medicines Agency (EMEA) have issued guidelines encouraging the implementation of dose-counters (Food and Drug Administration, "Guidance for industry: integration of dose counting mechanisms into MDI drug products", 2003; European Agency for Evaluation of Medicinal Products, "Final guideline on the quality of inhalation and nasal products", 2005).

Dose counters can generally be classified according to the manner by which a 'count' is registered, these being mechanical counters comprised of a series of moving parts that respond to a movement or mechanical force resulting, for example, in a displacement of the container/housing; electronic counters having electrical circuitry to sense an event associated with an actuation such as sound, temperature or pressure change; and electro-mechanical counters which combine electrical and mechanical parts.

Some background prior art relating to dose counters includes: EP1169245 Dispensing Apparatus Comprising a Dosage Counting Device; PCT/GB97/03480 Inhaler Dose Counter; PCT/US1996/008418 Indicator Device Responsive to Axial Force; PCT/FR2004/001844 Improved Dose Indicator for Fluid Product Dispensing Device; GB2372542 Dosage Counting Device; PCT/CA04/001884 Indicating Device with Warning Dosage Indicator; PCT/US04/039926 Dose Counter for Dispensers; and U.S. Pat. No. 7,047,964 Dispenser for Medicament.

Other developments in the field of dose counters include Bang & Olufsen Medicom's 'Insulair' (Trade Mark) device, and the disclosures of: WO 98/056444 Dispenser with Doses Counter; WO 04/001664 Actuation Indicator for a Dispensing Device; WO 07/012854 Canister-Supported Rotating Ring Count Readout Assembly for a Metered Dose Inhaler; and DE 10061723 Zählwerk zum Zählen dosierter Abgaben flüssiger oder fester Produkte sowie Einrichtung zum dosierten Abgeben solcher Produkte.

It has been found that, during use of the dispenser and counter, manufacturing tolerances may in some instances affect the performance. For example, it has been found that manufacturing tolerances mean that the length of a container or substance source can vary from container to container. Furthermore, the length of the spout of the container may vary, too.

This can cause problems in dispenser devices wherein the aerosol can is stationary and another part is moved relative to the can to displace its valve and dispense medicament. Typically the other moving part can only move a certain distance (i.e. a predetermined amount of travel) which means that if, for example a can or its valve is relatively short, the valve may not be fully displaced. As a result, a full dose of medicament may not be dispensed.

There have been different approaches taken to overcoming this problem. See, for example, WO2003/080161 or WO2007/029019.

In the above-mentioned previous approaches, the dispenser body and cap are a constant size and the canister is placed in the body at the same position in all dispensers. The variation in the resulting space between the end of the canister and the cap is taken by deformable materials placed atop the container. However, the above solutions do not always provide satisfactory results.

Furthermore, with reference to the counter, it has proven difficult to provide dose counters that reliably "count" the release of medicament doses from containers. The difficulty encountered is that a relatively small movement, typically of the metering valve stem, needs to be detected and translated into a count. This difficulty is exacerbated by manufacturing tolerances in the length of medicament containers which means they do not have a consistent length, and also manufacturing tolerances in the dimensions of the components comprising the counter mechanism and its coupling to the dispenser mechanism. At the same time, it is highly undesirable for any movements to not be counted since this will lead to the counter indicating a higher number of doses remaining than is actually the case. Moreover there is also regulatory pressure to minimise the number of false counts.

As such, we have appreciated the need for an improved dispenser.

SUMMARY OF THE INVENTION

The present invention therefore provides a dispenser for dispensing a dose of a gaseous, gas borne or droplet substance from a substance source, the dispenser comprising: a body for receiving a substance source, the body having a mouthpiece; a junction member slideably arranged in the body for movement in a longitudinal axis of the body to release a dose of a substance from a substance source, the junction member comprising a socket for receiving a spout of a substance source; a dispenser driver for moving the junction member in the longitudinal axis of the body to release a dose of a substance from a substance source, the dispenser driver comprising a pivot shaft and a cam arranged on the shaft, the dispenser driver being arranged within the body such that rotation of the pivot shaft causes the cam to rotate and apply a force to the junction member so as to move the junction member in the longitudinal axis; a cam follower slideably arranged within the body, the cam follower comprising a base and a substantially rigid protrusion extending from the base, the protrusion being arranged between the dispenser driver and the junction member such that a force applied by the cam of the dispenser driver to the protrusion causes the cam follower to slideably move in the longitudinal axis of the body and apply a force to the junction member so as to release a dose of a substance from a substance source; a dispenser cap comprising a hollow body having a lower open end engageable with the body, and an upper open end for receiving a cap closure device for closing the upper open end, the upper open end comprising an engageable portion; and a cap closure device, comprising: an upper cap closure portion for engaging with the upper open end of the dispenser cap to close the upper open end of the dispenser cap; a lower cap closure portion for engaging with the engageable portion to secure the cap closure device to the dispenser cap; and a bistable portion connecting the upper cap closure portion and the lower cap closure portion, the bistable portion being switchable between a first stable form in which the bistable portion is extended, and a second stable form in which the bistable portion is collapsed, wherein, when the bistable portion is in the second stable form, the upper cap closure portion engages with the upper open end of the dispenser cap to close the dispenser cap; a dose counter for indicating a number of actuations of the dispenser corresponding to a number of doses dispensed from a substance source, or a number of doses remaining in a substance source, the dose counter comprising: a first ring member having a first indicia and being rotatable in increments about the longitudinal axis, the first indicia indicating a count; and a limiting member comprising a limiting mechanism, wherein the limiting mechanism comprises an engaging portion arranged to act radially with respect to the first ring member to contact the first ring member to limit free rotation of the first ring member relative to the limiting member about the axis.

The provision of a cam follower between the junction member and the cam provides more reliable longitudinal movement of the junction member within the body to effect release of a dose of a medicament from a medicament container. Since the protrusions are substantially rigid, the whole cam follower moves longitudinally up and down as the cam arrangement imparts an upward force on the protrusion. As such, this enables a more reliable longitudinal action of the junction member.

The cap, in combination with the closure device, provides a means of enclosing a portion of the dispenser. Advantageously, the bistable portion of the closure device that is switchable between two stable forms (extended and collapsed) enables the closure device to be inserted and the cap closed when the closure device is in the desired position relative to the cap. Furthermore, the cap closure device, once in a stable form, requires a force to be applied to the upper closure portion to switch between the stable forms. As such, once in the collapsed form, the closure device is difficult to remove from the cap, thereby securing the closure device to the cap so that it cannot easily be removed. Furthermore, by using the above-mentioned cap closure device, a dispenser is able to be assembled where the medicament container of the dispenser can be fixed in the body in such a position that reliable and reproducible dosing can be achieved regardless of differences in the length of the spout and/or length of the container due to manufacturing tolerances.

Furthermore, by providing a limiting mechanism that acts radially on the first ring member, this alleviates the problems associated with manufacturing tolerances in the vertical direction (which is perpendicular to the radial direction acting on the first ring member). Tolerances in the vertical dimension have little effect on the action of the limiting mechanism acting radially with respect to the first ring member. As such, more reliable operation of the limiting mechanism, and thus the counter, is enabled.

In the above dispenser, the engaging portion may comprise one or more teeth arranged to contact an inner circumferential surface of the first ring member. Alternatively, the engaging portion may be arranged to contact an outer circumferential surface of the first ring member.

The first ring member may comprise an engaging portion arranged to co-operate with the engaging portion of the limiting member to limit free rotation of the first ring member relative to the limiting member about the axis. The engaging portion on the first ring member preferably comprises a plurality of teeth on an inner circumferential surface of the first ring member. Alternatively, the plurality of teeth may be located on an outer circumferential surface of the first ring member. The plurality of teeth on the inner or outer circumferential surface of the first ring may comprise ratchet shaped teeth. By providing ratchet teeth, this enables limited rotation in one direction (preferably the count direction) and enables rotation in a reverse count direction to be prevented.

The one or more teeth of the limiting member engaging portion may comprise one or more triangular or ratchet-shaped teeth. This enables the engaging portion to interact with the engaging portion on the first ring member to limit its free rotation.

The limiting mechanism may also comprise a guide, the guide comprising an arm spaced apart from the limiting member engaging portion in a fixed relation, the guide being configured to contact the first ring member such that the limiting member engaging portion maintains contact with the first ring member.

By providing the guide arm at a fixed distance from the engaging portion that may move radially, the engaging portion may more reliably track the first ring member, to ensure that the engaging portion remains in contact with the engaging portion on the first ring member. That is, movement of the first ring member in the radial direction (for example if there is some radial play between the first ring member and the limiting ring member) should not cause the engaging portion to disengage with the engaging portion on the first ring member, since the arm will follow the movement of the first ring member or any contours that the first ring member may have (since it is in contact with the first ring member) when the first ring member moves radially outwards, and the engaging portion will follow movement of the first ring member when the first ring member moves radially inwardly.

Preferably, the guide contacts the first ring member on an outer circumferential surface. In embodiments where the engaging portion on the first ring member is on the outer circumferential surface of the first ring member, the guide acts on the inner circumferential surface.

The limiting mechanism may also be supported on a base having a fixed end and a floating end, the fixed end being coupled to the limiting member and the floating end being free of the limiting member, and wherein the base is flexible at the fixed end such that the floating end is moveable radially with respect to the first ring member. Preferably, the limiting member engaging portion is located at the floating end of the base. The engaging portion may therefore move radially inwardly and outwardly with respect to the first ring member.

The limiting member may also comprise a limiting ring member coaxially arranged about the same axis as the first ring member.

When the limiting member comprises a limiting ring member, the limiting ring member may comprises one or more locating recesses disposed in an upper circumferential surface for engaging with correspondingly-shaped protrusions in the hollow body of the dispenser cap for preventing rotation of the limiting ring member about the axis.

Such an arrangement enables to the limiting mechanism to remain in a fixed relation to the first ring member.

In any of the above described limiting mechanisms, the limiting mechanism may be configured to provide a frictional resistance to the first ring member in a forward count direction of the first ring member, and to prevent movement of the first ring member in a reverse count direction. As such, this arrangement provides protection against over-counting in a forward count direction, and prevents rotation of the counter in a reverse count direction.

The present invention also provides a dispenser for dispensing a dose of a gaseous, gas borne or droplet substance from a substance source, the dispenser comprising: a body for receiving a substance source, the body having a mouthpiece; a junction member slideably arranged in the body for movement in a longitudinal axis of the body to release a dose of a substance from a substance source, the junction member comprising a socket for receiving a spout of a substance source; a dispenser driver for moving the junction member in the longitudinal axis of the body to release a dose of a substance from a substance source, the dispenser driver comprising a pivot shaft and a cam arranged on the shaft, the dispenser driver being arranged within the body such that rotation of the pivot shaft causes the cam to rotate and apply a force to the junction member so as to move the junction member in the longitudinal axis; a cam follower slideably arranged within the body, the cam follower comprising a base and a substantially rigid protrusion extending from the base, the protrusion being arranged between the dispenser driver and the junction member such that a force applied by the cam of the dispenser driver to the protrusion causes the cam follower to slideably move in the longitudinal axis of the body and apply a force to the junction member so as to release a dose of a substance from a substance source; a dispenser cap comprising a hollow body having a lower open end engageable with the body, and an upper open end for receiving a cap closure device for closing the upper open end, the upper open end comprising an engageable portion; and a cap closure device, comprising: an upper cap closure portion for engaging with the upper open end of the dispenser cap to close the upper open end of the dispenser cap; a lower cap closure portion for engaging with the engageable portion to secure the cap closure device to the dispenser cap; and a bistable portion connecting the upper cap closure portion and the lower cap closure portion, the bistable portion being switchable between a first stable form in which the bistable portion is extended, and a second stable form in which the bistable portion is collapsed, wherein, when the bistable portion is in the second stable form, the upper cap closure portion engages with the upper open end of the dispenser cap to close the dispenser cap.

The provision of a cam follower between the junction member and the cam provides more reliable longitudinal movement of the junction member within the body to effect release of a dose of a medicament from a medicament container. Since the protrusions are substantially rigid, the whole cam follower moves longitudinally up and down as the cam arrangement imparts an upward force on the protrusion. As such, this enables a more reliable longitudinal action of the junction member.

The cap, in combination with the closure device, provides a means of enclosing a portion of the dispenser. Advantageously, the bistable portion of the closure device that is switchable between two stable forms (extended and collapsed) enables the closure device to be inserted and the cap closed when the closure device is in the desired position relative to the cap. Furthermore, the cap closure device, once in a stable form, requires a force to be applied to the upper closure portion to switch between the stable forms. As such, once in the collapsed form, the closure device is difficult to remove from the cap, thereby securing the closure device to the cap so that it cannot easily be removed. Furthermore, by using the above-mentioned cap closure device, a dispenser is able to be assembled where the medicament container of the dispenser can be fixed in the body in such a position that reliable and reproducible dosing can be achieved regardless of differences in the length of the spout and/or length of the container due to manufacturing tolerances.

The body of the dispenser may comprise a guide for guiding the slideable motion of the cam follower base in the longitudinal axis, the guide being shaped to receive the base of the cam follower in a slideable engagement. Preferably, the guide comprises one or more guide rails arranged and adapted to co-operate with one or more guide rails on the cam follower base such that the cam follower is slideable within the body.

The cam follower may comprise a resiliently deformable clip disposed on a lower edge of the base for engaging with a correspondingly shaped protrusion in the body, and wherein, when the clip is engaged with the protrusion, the cam follower is retained in the longitudinal position in the body until a force is exerted on the cam follower by the cam. Such a clip aids assembly during manufacture of the dispenser, since the clip will maintain the cam follower in the correct position whilst other components are assembled around the cam follower.

The dispenser may comprise a pivotally mounted closure for the mouthpiece, the closure being coupled to the dispenser driver such that pivoting of the cover causes rotation of the pivot shaft of the dispenser driver.

The dispenser may also comprise: a breath actuatable valve incorporated with the junction member, for controlling the release of a gas and/or liquid comprising a substance, the valve comprising: a flexible tube for receiving a dose of a substance, the tube extending from an inlet end connected to the junction member socket, having a location which is kinkable for closure of the valve in a ready position and moveable to a release position in which the tube is un-kinked for opening of the valve, and having an outlet end moveable for kinking/un-kinking of the tube; and an outlet member carrying the outlet end of the flexible tube and pivotally connected to the junction member for control of kinking/un-kinking movement of the flexible tube; the tube being kinked to an obturating extent when the pivotal outlet member is in a ready position and un-kinked when the pivotal outlet member is moved to a release position. Preferably, the dispenser comprises: a sear on the outlet member to hold the outlet member in the ready position prior to inhalation; a breath actuatable flap carried on the junction member and arranged for action of inhalation breath on it, the flap having: a latch complementary to the sear; the flap being arranged: to releasably receive the pivotal outlet member for kinked closure of the flexible tube by cooperation of the latch and the sear and to release the pivotal outlet member for un-kinking of the tube, and substance release, on inhalation, by release of the sear from the latch and movement to the release position of the outlet member.

In such a dispenser, the pivotal outlet member is arranged to move by the force arising from pressure in the kinked location and/or under the resilience of the kinked location itself. Furthermore, the junction member, the kink tube and the pivotal outlet member are an integral plastics material injection moulding, the pivotal outlet member being pivoted to the junction member by one or more living hinges and having an outlet nozzle held by the outlet member.

The flap may have an integral spring acting on the junction member to bias it normally to a position in which the flap rests on an upper crown portion of the junction member. Furthermore, the flap may include a finger arranged to act on the pivoted outlet member to urge it towards its open position as the flap moves under the action of inhalation breath.

The bistable portion of the cap closure device may comprise: a substantially rigid separator connected to the upper cap closure portion; and a resiliently deformable separator having first and second ends, the first end being connected to the substantially rigid separator via a resiliently deformable joint, and the second end being connected to the lower cap closure portion via a resiliently deformable joint, wherein the resiliently deformable separator is configured to resiliently deform upon application of a force to the upper cap closure portion and lower cap closure portion so as to permit a change of form of the dispenser cap closure device between the first stable form and second stable form. Such a configuration advantageously provides the cap closure device with the ability to be switched between the two stable forms.

Preferably, an angle defined between an outer surface of the substantially rigid separator and the resiliently deformable separator is acute when in the second stable form, and obtuse when in the first stable form.

The lower cap closure portion may comprise a plurality of protrusions extending radially outwards having an upper surface for engaging with the engageable portion of the dispenser cap, and wherein a lower surface of the lower cap closure portion is engageable with a surface of a substance source when received in the dispenser. The plurality of protrusions extending from the lower cap closure portion thus provide a means to secure the cap closure portion to the cap.

The engageable portion of the dispenser cap may comprise a ramped portion, and wherein the ramped portion and the protrusions on the lower cap closure portion are configured such that rotation of the cap closure device causes the upper surface of the plurality of protrusions to ride along the ramped portion so as to draw the cap closure device further into the dispenser cap. Preferably, when the cap closure device is rotated, the riding of the upper surface of the protrusions along the ramped portion causes the lower surface of the lower cap closure portion to drive down onto a substance source when received in the dispenser.

By providing the ramped portions, the protrusions on the lower cap closure portion of the cap closure device may ride along the ramped portion and thus be drawn into the cap during rotation of the cap closure device. The position of the cap closure device relative to the cap may thus be adjusted prior to the bistable portion being switched from the extended to the collapsed forms. As such, tolerances in the length of the container or the container spout in the dispenser may be accounted for prior to final assembly of the dispenser.

The ramped portion may comprise a plurality of ramped portions around the circumference of a lip of the dispenser cap, the plurality of ramped portions equalling the number of plurality of protrusions on the lower cap portion of the cap closure device. Preferably, the ramped portions are separated from one and other by a gap having a width that is greater than or equal to the width of a protrusion on the lower cap closure portion.

An upper surface of the dispenser cap may comprise a limiting means for preventing rotation of the cap closure device when in the second stable form. Preferably, the limiting means comprises a plurality of teeth located on an upper surface of the dispenser cap, and wherein the dispenser cap closure device comprises a plurality of protrusions on a lower surface of the upper cap closure portion, the teeth and protrusions being configured to engage with one another so as to prevent rotation of the cap closure device when in the second stable form.

By providing a limiting means, further rotation of the cap closure device, once in the collapsed state, may be prevented. As such, the cap closure device is prevented from rotating further into, or out of the cap. The cap closure device is thus secured in place.

The dispenser cap may comprise one or more protrusions in the upper open end of the dispenser cap, the one or more protrusions being arranged to engage with a correspondingly shaped recess in the upper cap closure portion when the dispenser cap is closed by the dispenser closure device.

In embodiments comprising the cam follower and dispenser cap arrangement, the dispenser may also comprise a dose counter for indicating a number of actuations of the dispenser corresponding to a number of doses dispensed from a substance source, or a number of doses remaining in a substance source. In such embodiments, dispenser counter may comprise: a first ring member having a first indicia and being rotatable in increments about the longitudinal axis, the first indicia indicating a count; a second ring member having second indicia, the second ring member being rotatable in increments about the same axis as the first ring member, the second indicia indicating a count; a coupling mechanism for releasably coupling the second ring member to the first ring member, to allow the second and first ring members to rotate cooperatively when coupled and to allow independent rotating of the second ring member when not coupled; wherein the coupling mechanism comprises first and second engagement means, the first engagement means being movable radially outwardly and radially inwardly relative to the axis. This embodiment may also comprise a limiting member comprising a limiting mechanism, wherein the limiting mechanism limits free rotation of the first ring member relative to the limiting member about the axis.

By providing a limiting mechanism that acts radially on the first ring member, this alleviates the problems associated with manufacturing tolerances in the vertical direction (which is perpendicular to the radial direction acting on the first ring member). Tolerances in the vertical dimension have little effect on the action of the limiting mechanism acting radially with respect to the first ring member. As such, more reliable operation of the limiting mechanism, and thus the counter, is enabled.

In the dispenser comprising the cam follower, dispenser cap arrangement and counter comprising a limiting mechanism, the dispenser may also comprise a second ring member having second indicia, the second ring member being rotatable in increments about the same axis as the first ring member, the second indicia indicating a count; a coupling mechanism for releasably coupling the second ring member to the first ring member, to allow the second and first ring members to rotate cooperatively when coupled and to allow independent rotating of the second ring member when not coupled; wherein the coupling mechanism comprises first and second engagement means, the first engagement means being movable radially outwardly and radially inwardly relative to the axis.

In embodiments comprising the second ring member, the coupling mechanism may comprise a deflector to deflect the first engagement means radially outwardly. Preferably, the first engagement means is deflected radially outwardly after a predetermined degree of rotation of the second ring member, the predetermined amount of rotation of the second ring member being less than a full rotation of the second ring member about the axis. The deflector may be connected to, or integral with the limiting member.

The first engagement means is connected to, or integral with, the second ring member. The first engagement means may also comprise an arm having a slot and a contact end, preferably the first engagement means comprises four arms each having a slot and a contact end. The contact end may comprise an upwardly extending component that contacts the deflector.

The second engagement means may be connected to, or integral with, the first ring member. Furthermore, the second engagement means may comprise a plurality of protrusions. Preferably, the protrusions are equally spaced apart from one another.

When the first engagement means is moved radially outwardly, the first engagement means engages with one of the protrusions. When the first engagement means engages with one of the protrusions, the first ring member overcomes frictional resistance of the limiting mechanism in a forward count direction and the first ring member rotates in the forward count direction.

The first ring member may comprise a display cover element for obscuring a view of the second indicia.

The dispenser may also comprise a drive mechanism for rotating the second ring member, and wherein at least part of the drive mechanism is integral with the second ring member. Preferably, the drive mechanism comprises a pawl-and-teeth mechanism.

In such embodiments, the pawl-and-teeth mechanism comprises: a first and second pawl engageable with a plurality of teeth, and wherein each of the first and second pawls comprise a driving engagement face for engaging in a driving engagement with one of the plurality of teeth, and a sliding engagement face for sliding over one of the plurality of teeth.

Each of the first and second pawls may be arranged such that: the first pawl engages in a driving engagement with one of the plurality of teeth during a count stroke of the drive mechanism, and the second pawl engages in a driving engagement with one of the plurality of teeth during a return stroke of the drive mechanism.

Furthermore, each of the first and second pawls is arranged such that: the second pawl rides over one of the plurality of teeth during a count stroke of the drive mechanism, and the first pawl rides over one of the plurality of teeth during the return stroke of the drive mechanism.

Preferably, the first and second pawls are integral with the second ring member, and the plurality of teeth are disposed on a counter driver, the counter driver being coupleable to the junction member and arranged to be reciprocally moveable within a bore of the second ring member, and wherein the pawl-and-teeth mechanism is configured such that reciprocal movement of the counter driver within the bore of the second ring member causes rotational movement of the second ring member.

Preferably, the drive mechanism further comprise third and fourth pawls engageable with the plurality of teeth, the third and fourth pawls being integral with the first ring member on a surface radially opposing the first and second pawls.

The dispenser body may also comprise a counter driver guide configured to guide the counter driver in the body so as to prevent rotation of the counter driver in the longitudinal axis. Preferably, the counter driver guide comprises a protrusion extending from the body, the protrusion being configured and shaped so as to co-operate with a correspondingly shaped notch in the counter driver.

Furthermore, the junction member may also comprise one or more slots, and the counter driver comprises one or more protrusions for engaging with the junction member so as to couple the junction member and counter driver.

The first indicia may comprises one or more of: numbers, colours, letters and symbols. The second indicia comprises one or more of: numbers, colours, letters and symbols. The second indicia may comprise a first row of numbers, and said first indicia comprise a second and a third row of numbers.

In some embodiments, the first row of numbers represents units digits, said second row represents tens digits, and said third row represents hundreds digits. Furthermore, the first row of numbers may comprise repeated sets of integers. The second row of numbers may also comprise repeated sets of integers and said third row of numbers may comprise a set of integers.

The indicia may be printed, cut out from, embossed, moulded, adhered, incorporated, and/or painted on said first and second ring members.

The present invention also provides a dispenser for dispensing a dose of a gaseous, gas borne or droplet substance from a substance source, the dispenser comprising: a body for receiving a substance source, the body having a mouthpiece; a junction member slideably arranged in the body for movement in a longitudinal axis of the body to release a dose of a substance from a substance source, the junction member comprising a socket for receiving a spout of a substance source; a dispenser driver for moving the junction member in the longitudinal axis of the body to release a dose of a substance from a substance source, the dispenser driver comprising a pivot shaft and a cam arranged on the shaft, the dispenser driver being arranged within the body such that rotation of the pivot shaft causes the cam to rotate and apply a force to the junction member so as to move the junction member in the longitudinal axis; a cam follower slideably arranged within the body, the cam follower comprising a base and a substantially rigid protrusion extending from the base, the protrusion being arranged between the dispenser driver and the junction member such that a force applied by the cam of the dispenser driver to the protrusion causes the cam follower to slideably move in the longitudinal axis of the body and apply a force to the junction member so as to release a dose of a substance from a substance source; a dose counter for indicating a number of actuations of the dispenser corresponding to a number of doses dispensed from a substance source, or a number of doses remaining in a substance source, the dose counter comprising: a first ring member having a first indicia and being rotatable in increments about an axis, the first indicia indicating a count; and a limiting member comprising a limiting mechanism, wherein the limiting mechanism comprises an engaging portion arranged to act radially with respect to the first ring member to contact the first ring member to limit free rotation of the first ring member relative to the limiting member about the axis.

The provision of a cam follower between the junction member and the cam provides more reliable longitudinal movement of the junction member within the body to effect release of a dose of a medicament from a medicament container. Since the protrusions are substantially rigid, the whole cam follower moves longitudinally up and down as the cam arrangement imparts an upward force on the protrusion. As such, this enables a more reliable longitudinal action of the junction member.

Furthermore, by providing a limiting mechanism that acts radially on the first ring member, this alleviates the problems associated with manufacturing tolerances in the vertical direction (which is perpendicular to the radial direction acting on the first ring member). Tolerances in the vertical dimension have little effect on the action of the limiting mechanism acting radially with respect to the first ring member. As such, more reliable operation of the limiting mechanism, and thus the counter, is enabled.

In the above dispenser according to claim 67, the limiting mechanism is as described above.

In the above dispenser, the body is as defined as described above, and the cam follower is as described above.

The present invention also provides a dispenser for dispensing a dose of a gaseous, gas borne or droplet substance from a substance source, the dispenser comprising: a body for receiving a substance source, the body having a mouthpiece; a dispenser cap comprising a hollow body having a lower open end engageable with the body, and an upper open end for receiving a cap closure device for closing the upper open end, the upper open end comprising an engageable portion; and a cap closure device, comprising: an upper cap closure portion for engaging with the upper open end of the dispenser cap to close the upper open end of the dispenser cap; a lower cap closure portion for engaging with the engageable portion to secure the cap closure device to the dispenser cap; and a bistable portion connecting the upper cap closure portion and the lower cap closure portion, the bistable portion being switchable between a first stable form in which the bistable portion is extended, and a second stable form in which the bistable portion is collapsed, wherein, when the bistable portion is in the second stable form, the upper cap closure portion engages with the upper open end of the dispenser cap to close the dispenser cap; a dose counter for indicating a number of actuations of the dispenser corresponding to a number of doses dispensed from a substance source, or a number of doses remaining in a substance source, the dose counter comprising: a first ring member having a first indicia and being rotatable in increments about an axis, the first indicia indicating a count; and a limiting member comprising a limiting mechanism, wherein the limiting mechanism comprises an engaging portion arranged to act radially with respect to the first ring member to contact the first ring member to limit free rotation of the first ring member relative to the limiting member about the axis.

The cap, in combination with the closure device, provides a means of enclosing a portion of the dispenser. Advantageously, the bistable portion of the closure device that is switchable between two stable forms (extended and collapsed) enables the closure device to be inserted and the cap closed when the closure device is in the desired position relative to the cap. Furthermore, the cap closure device, once in a stable form, requires a force to be applied to the upper closure portion to switch between the stable forms. As such, once in the collapsed form, the closure device is difficult to remove from the cap, thereby securing the closure device to the cap so that it cannot easily be removed. Furthermore, by using the above-mentioned cap closure device, a dispenser is able to be assembled where the medicament container of the dispenser can be fixed in the body in such a position that reliable and reproducible dosing can be achieved regardless of differences in the length of the spout and/or length of the container due to manufacturing tolerances.

Furthermore, by providing a limiting mechanism that acts radially on the first ring member, this alleviates the problems associated with manufacturing tolerances in the vertical direction (which is perpendicular to the radial direction acting on the first ring member). Tolerances in the vertical dimension have little effect on the action of the limiting mechanism acting radially with respect to the first ring member. As such, more reliable operation of the limiting mechanism, and thus the counter, is enabled.

With the above dispenser, the limiting mechanism is as described above. The dispenser cap and dispenser cap closure device are as described as above.

In any of the above-described embodiments, the dispenser may further comprise a substance source. The substance source may be a pressurised metered-dose inhaler (pMDI).

LIST OF FIGURES

We shall now describe embodiments of the present invention, by way of example only, and with reference to the accompanying drawings, in which:

FIG. 1 is a perspective view of a dispenser according to the invention in closed position;

FIG. 2 is a similar view of the dispenser in open position;

FIG. 3 is a central cross-sectional view of the dispenser closed;

FIG. 4 is an exploded view of a prior version of the dispenser;

FIG. 5a is an inside, front view of a main body part of the dispenser;

FIG. 5b is an inside, front view of a portion of the main body part shown in FIG. 5a;

FIG. 5c is a cross-sectional view along line X-X of the main body part of FIG. 5a;

FIG. 5d is a cam follower component of a preferred embodiment of the dispenser;

FIG. 5e is a rear view of the cam follower of FIG. 5d;

FIG. 6 is an inside, rear, view of a cover of the dispenser;

FIG. 9 is an oblique view from the front and below of a junction member of the dispenser (shown in a form after moulding, but prior to insertion into the main body part);

Figure 12:
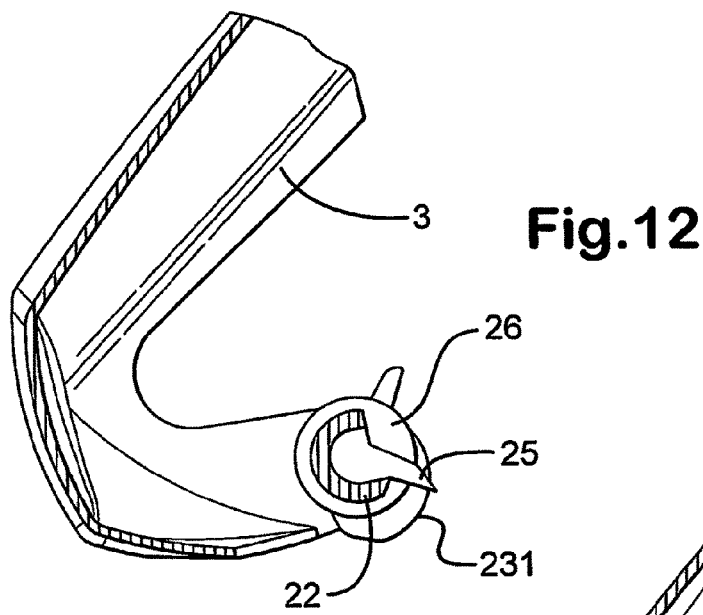
Figure 13:
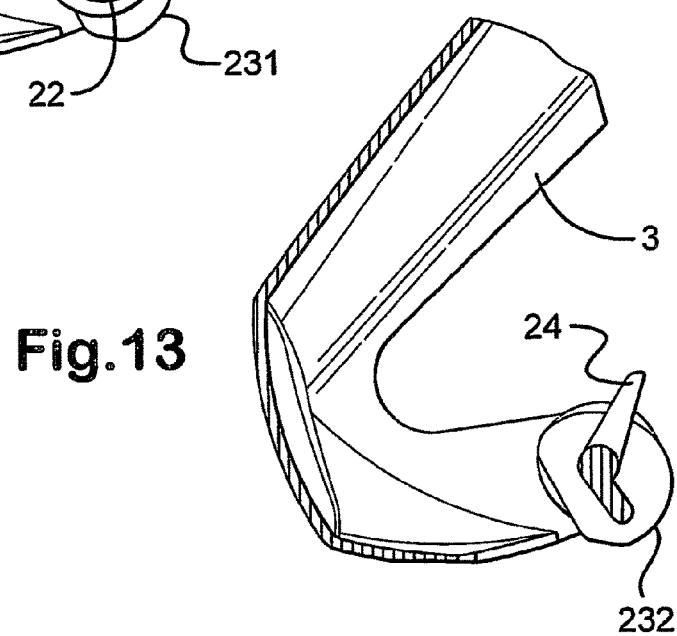
Figure 14:
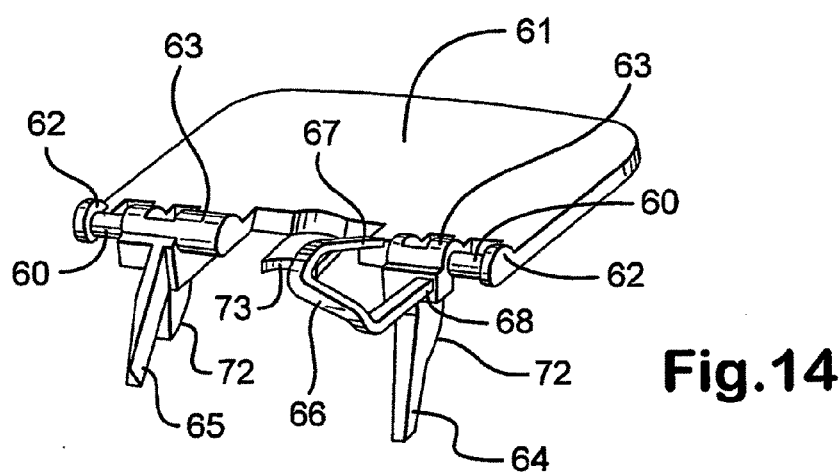
Figure 15:
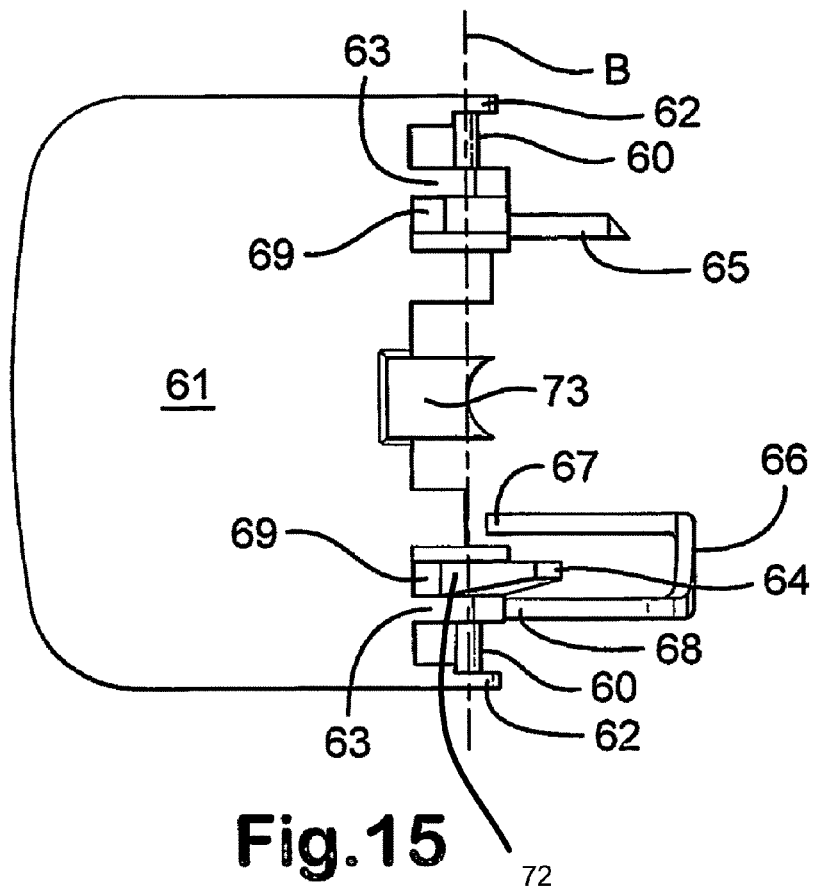
Figure 16:
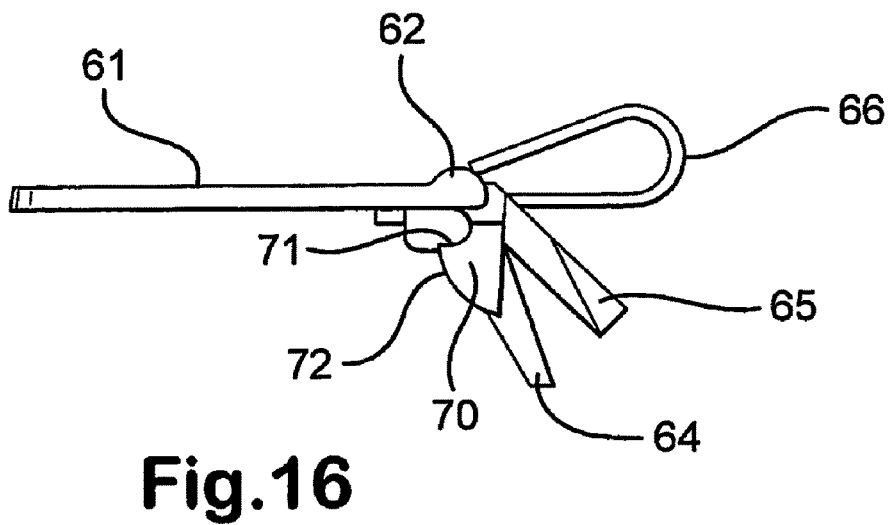
Figure 17:
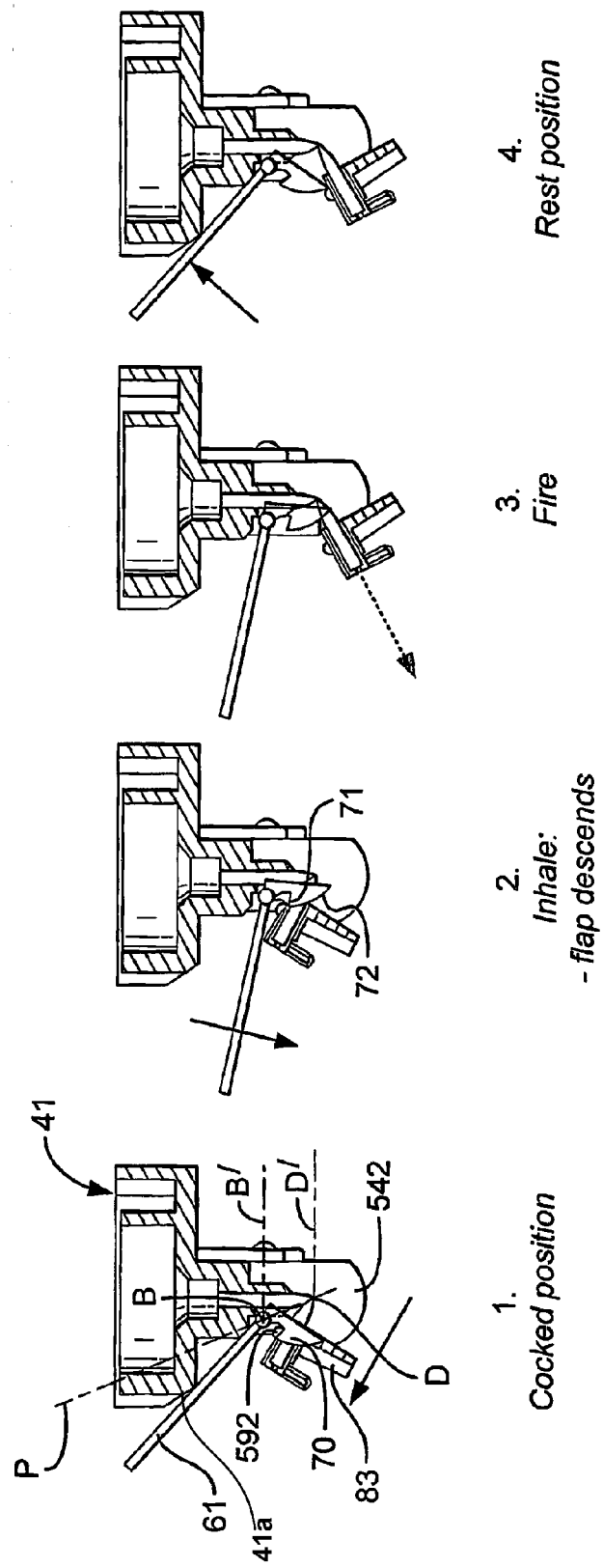
Figure 18:
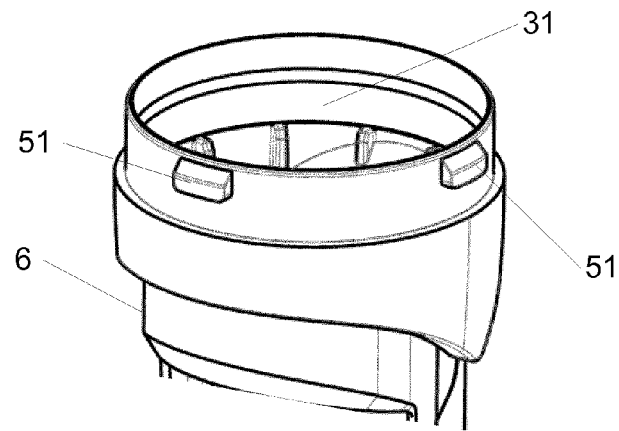
Figure 19:
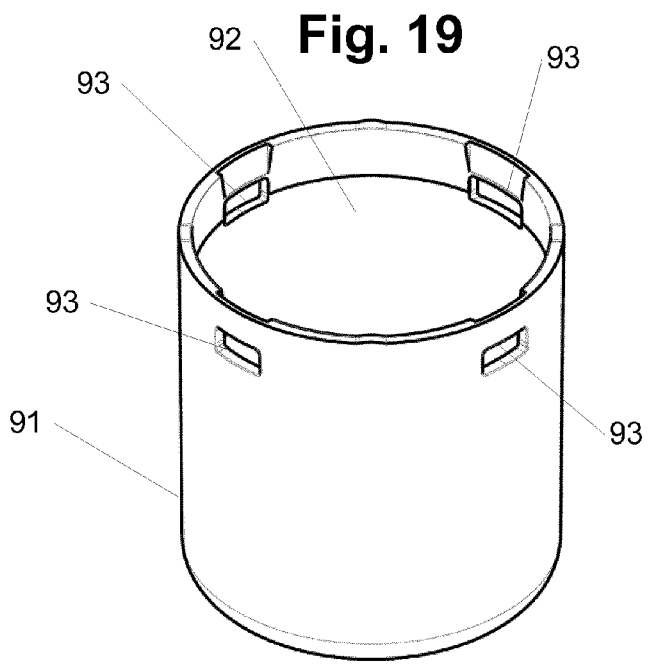
Figure 22:
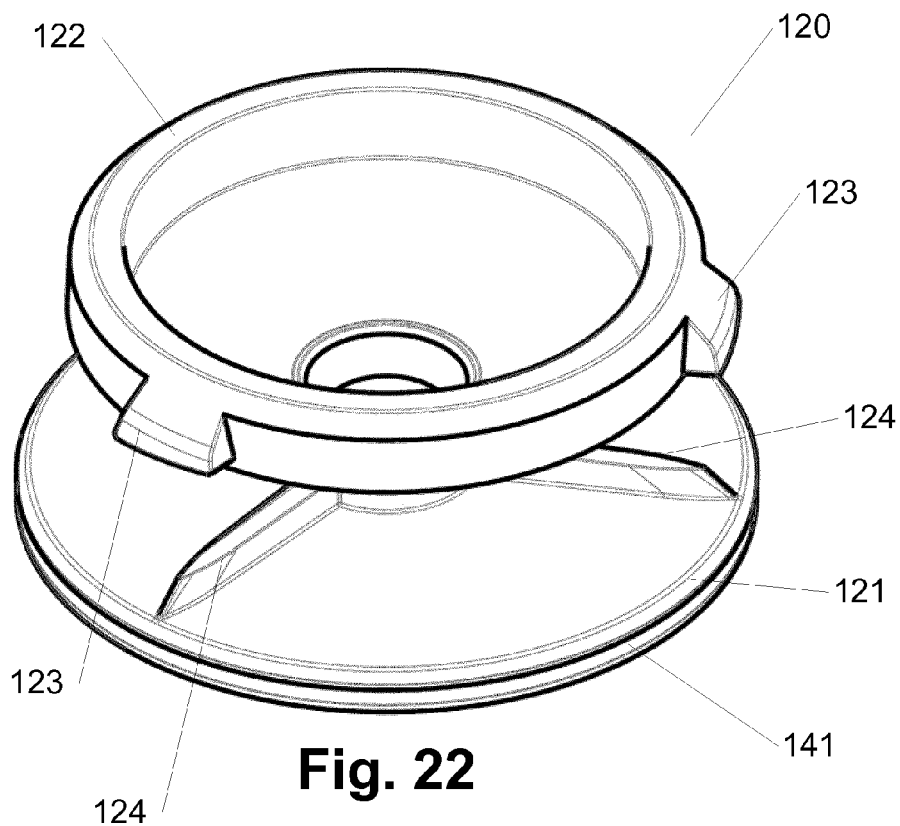
Figure 23:
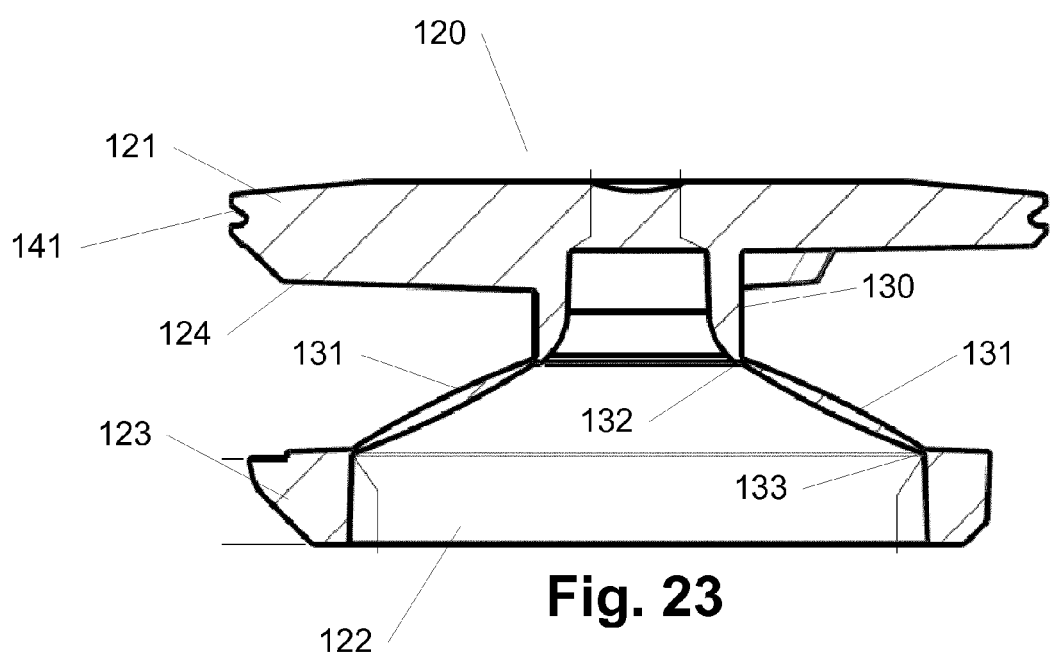
Figure 24A:
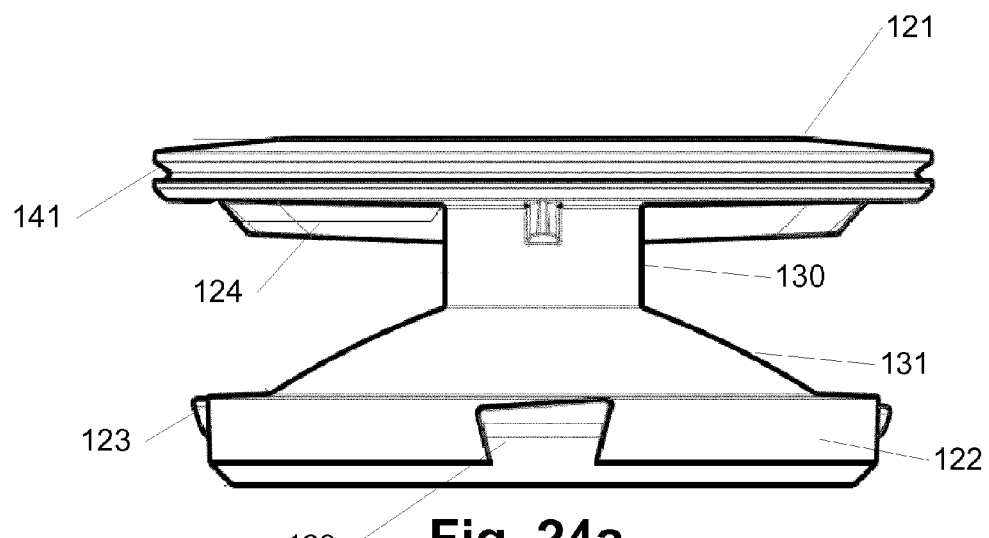
Figure 24B:
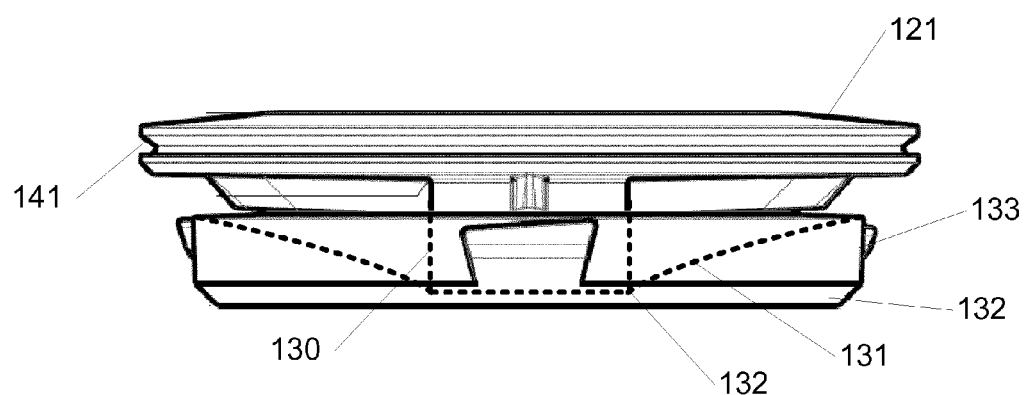
Figure 26A:
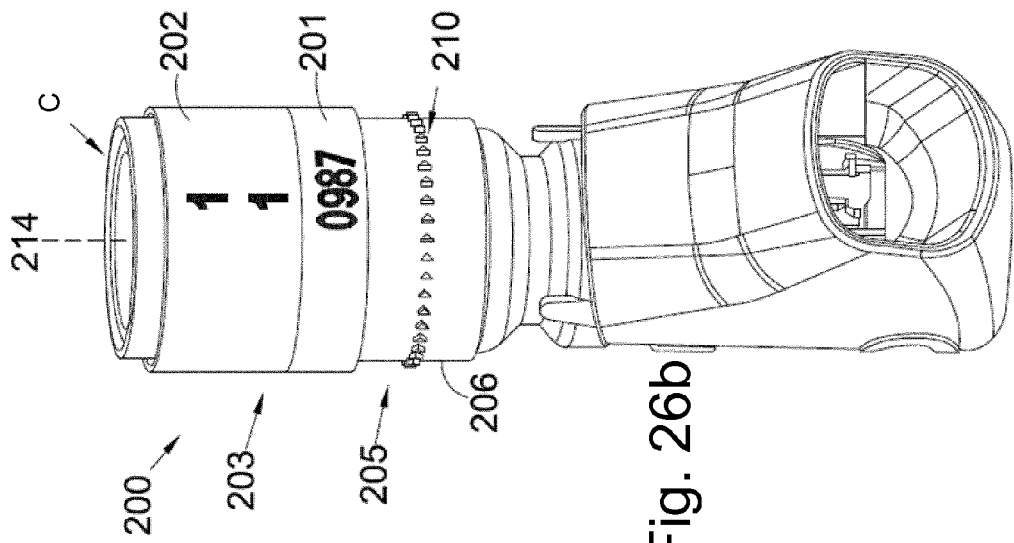
Figure 26B:
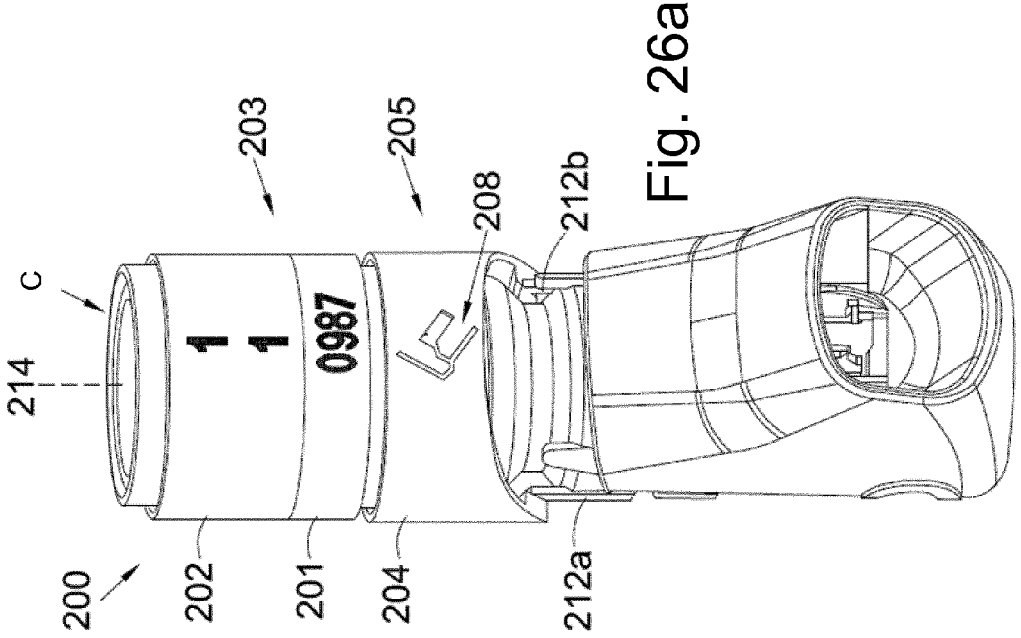
Figure 27A:
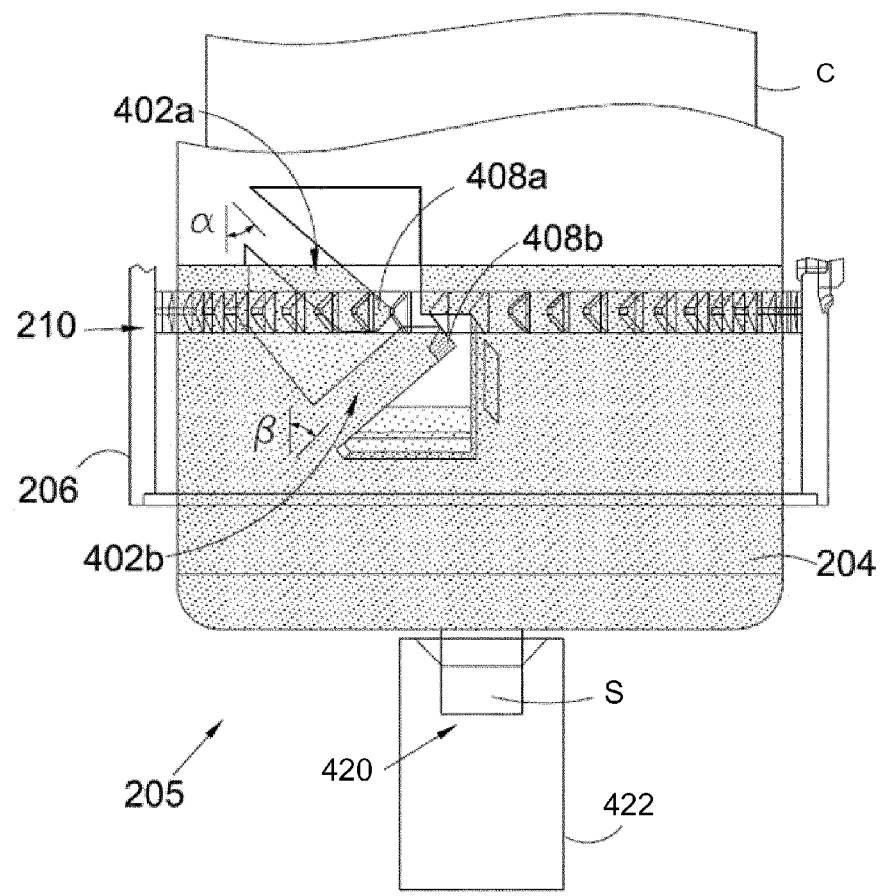
Figure 27B:
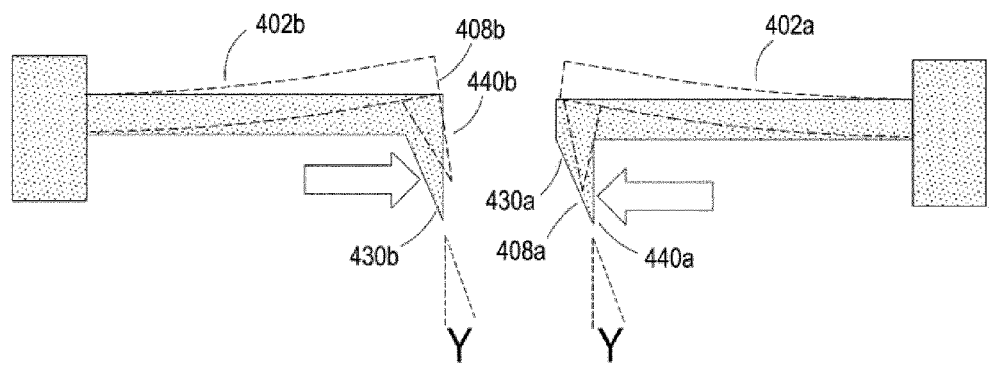
Figure 30A:
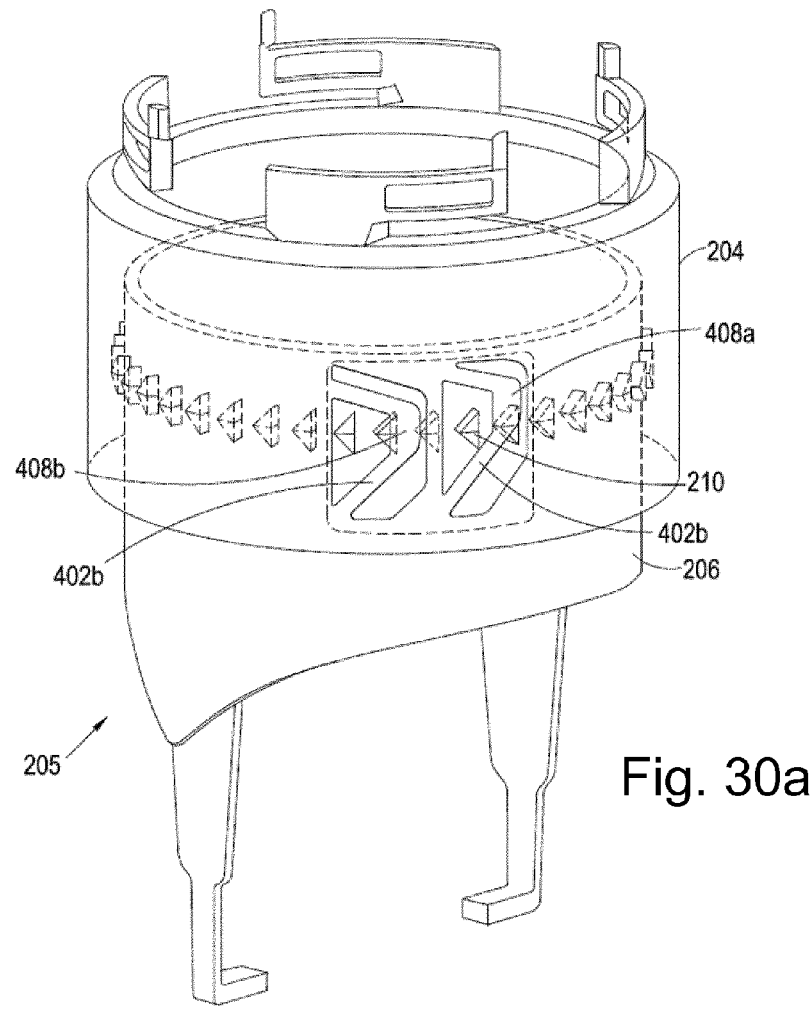
Figure 30B:
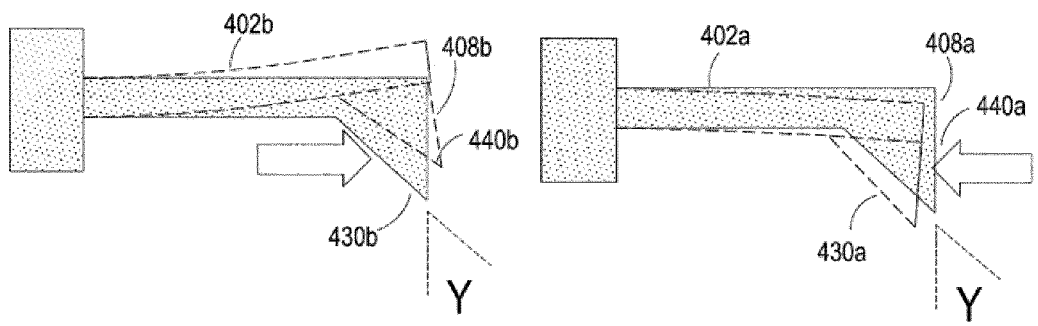
Figure 30E:
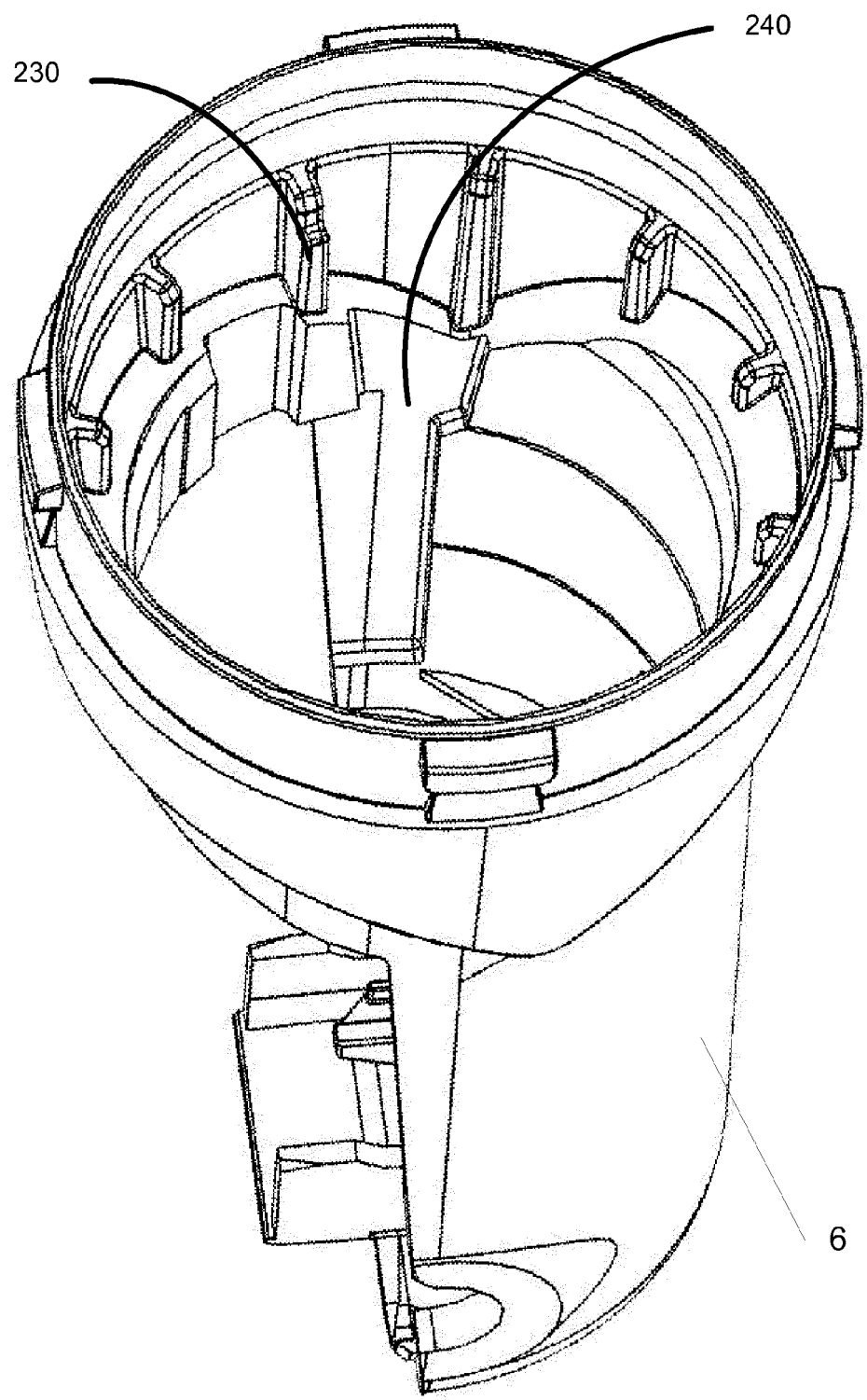
Figure 33:
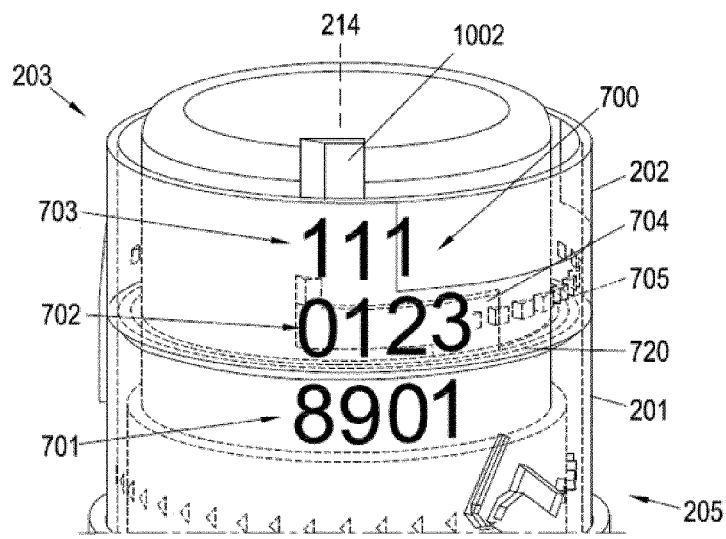
Figure 34:
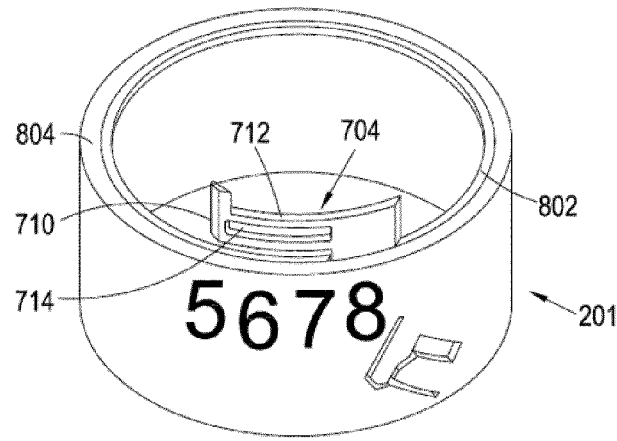
Figure 35:
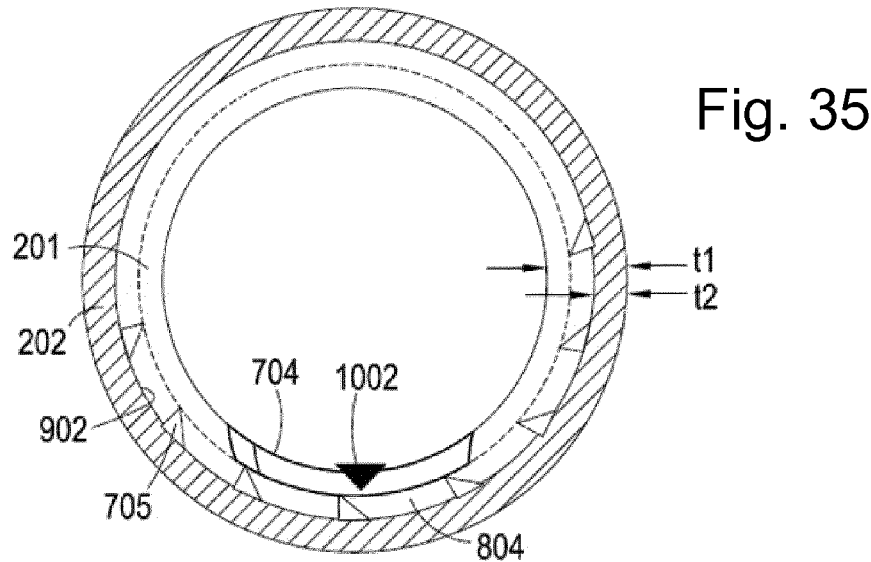
Figure 38A:
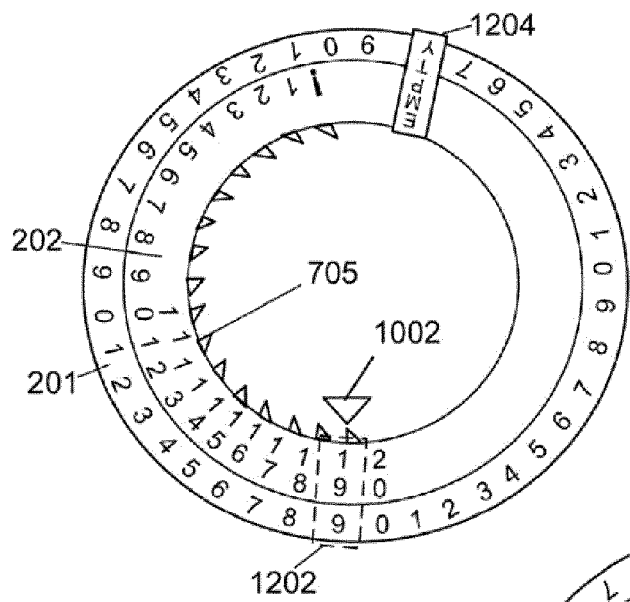
Figure 38B:
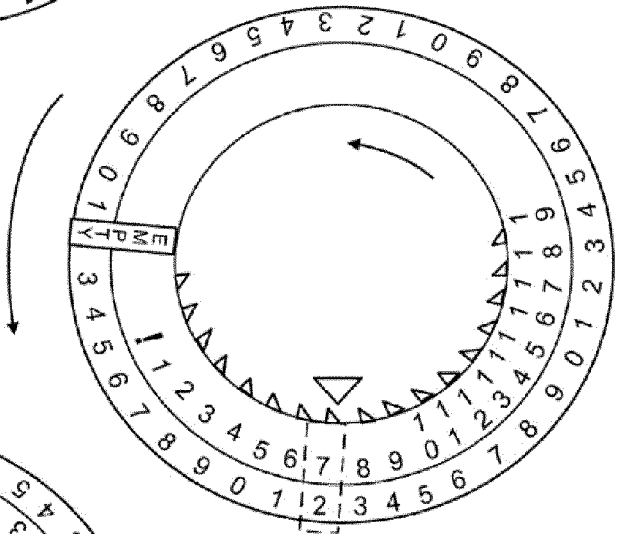
Figure 38C:
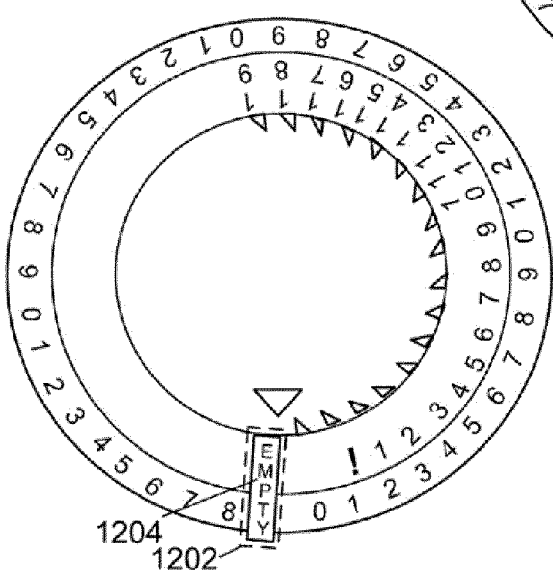
Figure 39:
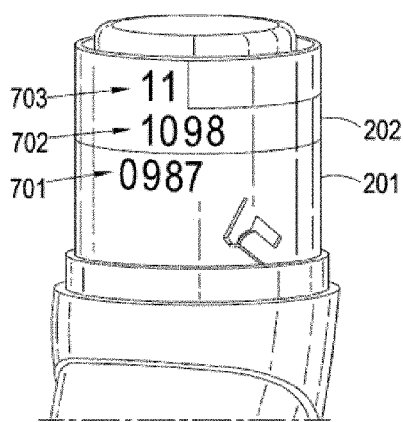
Figure 40:
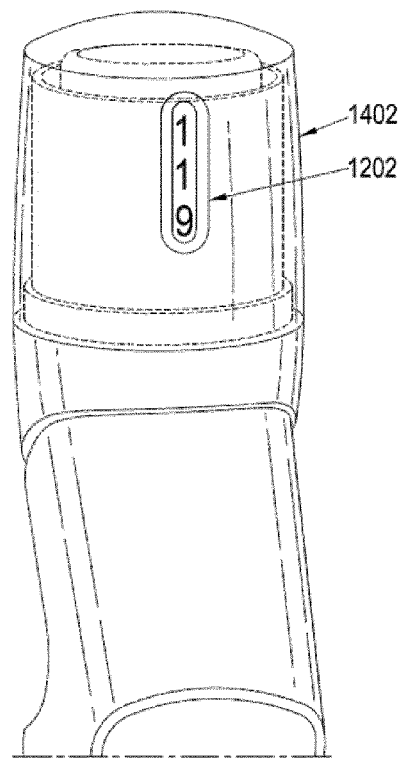
Figure 41C:
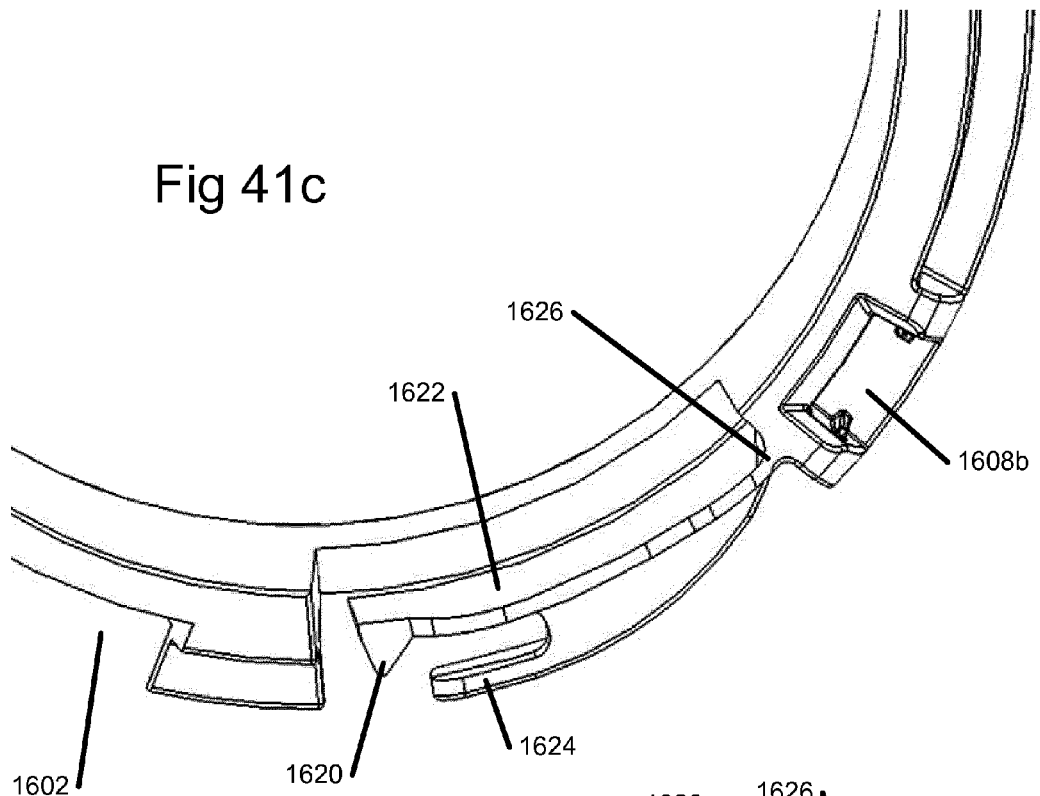
Figure 41D:
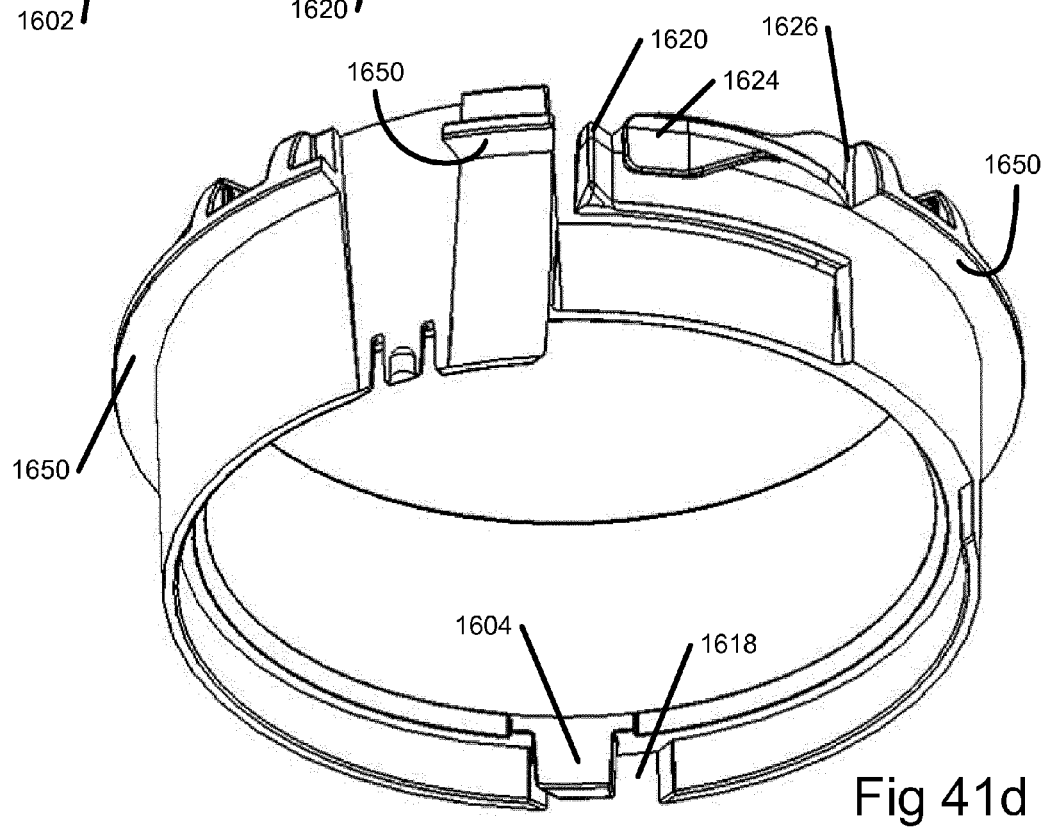
Figure 42:
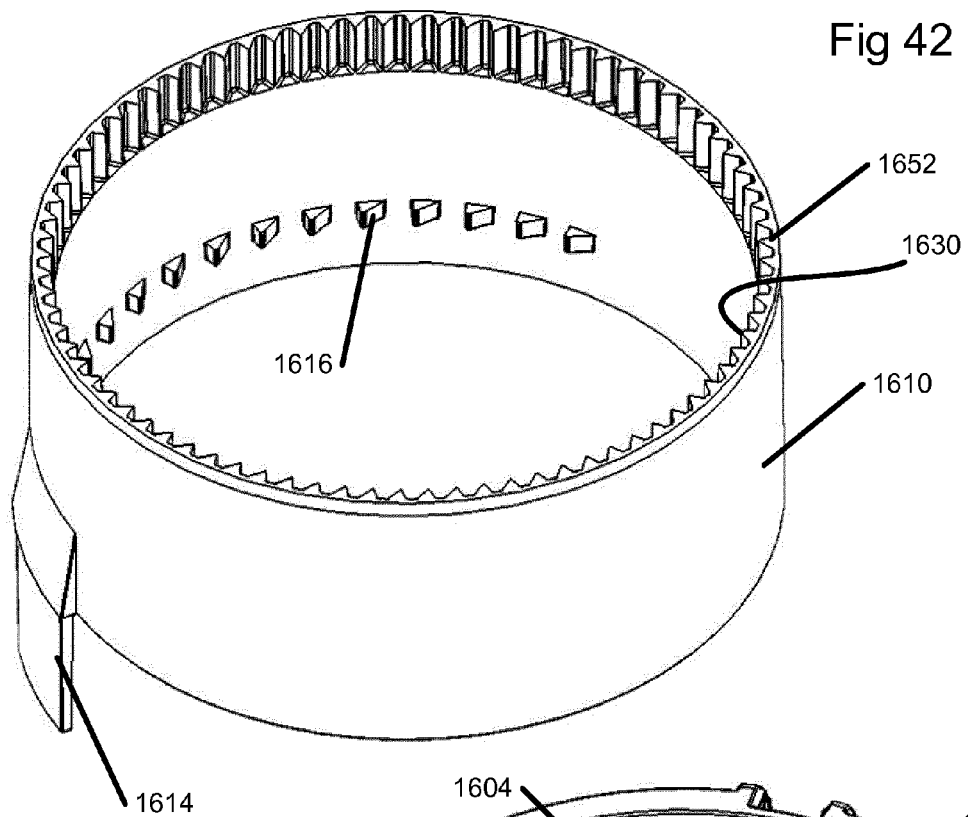
Figure 43A:
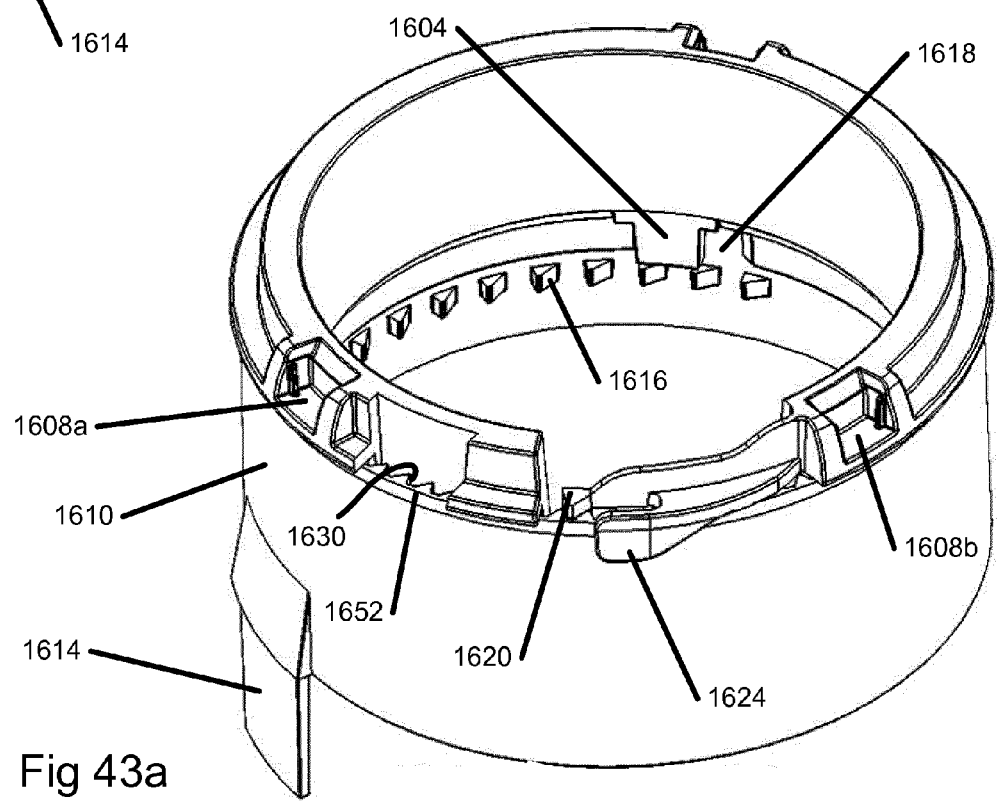
Figure 43B:
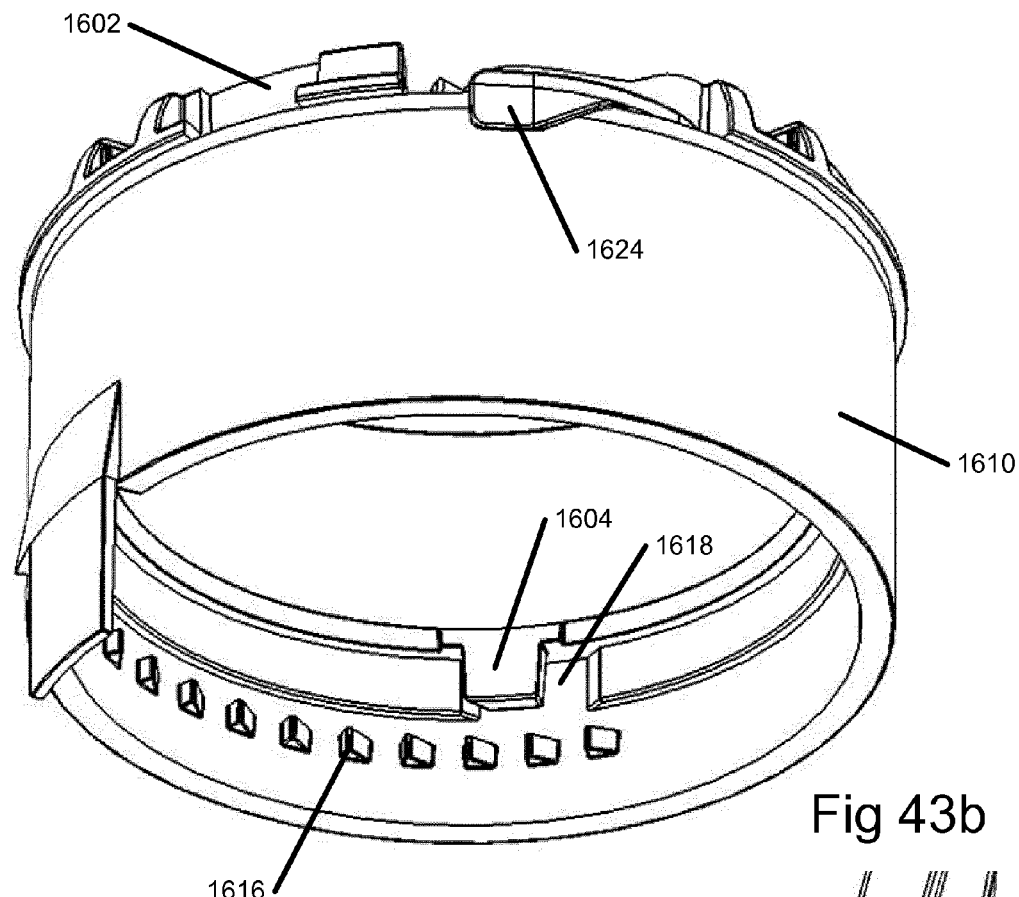
Figure 43C:
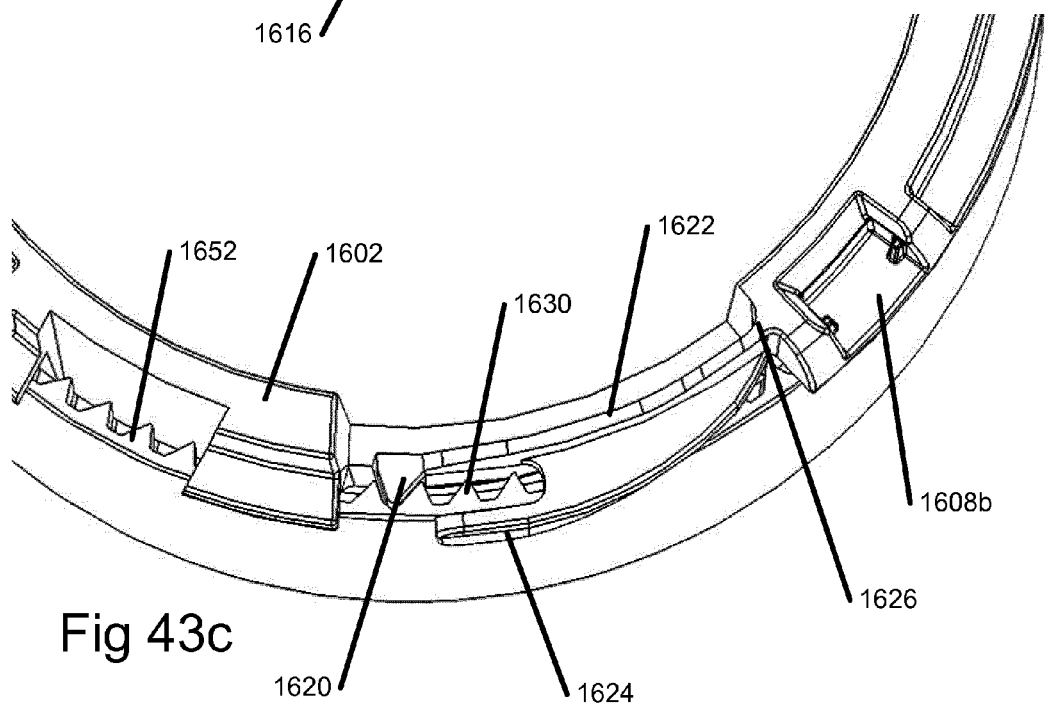

FIG. 10 a rear view of the junction member;

FIG. 11 is a cross-sectional side view of the junction member on the line A-A in FIG. 10;

FIG. 12 is a cross-sectional side view of the cover on line C-C in FIG. 6;

FIG. 13 is a central, cross-sectional side view of the cover on line B-B in FIG. 6;

FIG. 14 is a perspective view from behind of a flap of the dispenser;

FIG. 15 is a plan view of the flap;

FIG. 16 is a side view of the flap;

FIG. 17 is a series of scrap views of the flap and kink valve in the junction member illustrating operation of the valve;

FIG. 18 shows an upper portion of a preferred main body part of the dispenser;

FIG. 19 is an underside view of a preferred dispenser cap;

FIG. 20a is an upper-end view of the dispenser cap of FIG. 19;

FIG. 20b is a perspective view of the dispenser cap of FIG. 19;

FIG. 21 is a cut-through view of the dispenser cap of FIG. 19 through axis X-X of FIG. 20a;

FIG. 22 is a preferred dispenser cap closure device;

FIG. 23 is a cut-through view along the X-X line of the dispenser cap closure device of FIG. 22;

FIG. 24a is the dispenser cap closure device of FIG. 22 in an extended state;

FIG. 24b is the dispenser cap closure device of FIG. 22 in a collapsed state;

FIGS. 25a to 25f show a sequence of steps of the dispenser cap assembly;

FIG. 26a is a perspective view of a dispenser including a counter;

FIG. 26b is a perspective view of a dispenser including the counter;

FIGS. 27a and 27b show a drive mechanism for the counter;

FIGS. 28a to 28d are schematic diagrams showing a part of the principle of operation of the drive mechanism of the counter;

FIGS. 29a to 29d are schematic diagrams showing another part of the principle of operation of the drive mechanism of the counter;

FIGS. 30a and 30b show a preferred drive mechanism for the counter;

FIG. 30c shows a yoke (also known as a counter driver or teeth-bearing member) of a preferred embodiment of the counter;

FIG. 30d shows a junction member of a preferred embodiment of the dispenser;

FIG. 30e shows a top perspective view of a main body part for use with the yoke of FIG. 30c;

FIGS. 31a to 31d are schematic diagrams showing a part of the principle of operation of the preferred drive mechanism of the counter;

FIGS. 32a to 32d are schematic diagrams showing a part of the principle of operation of the preferred drive mechanism of the counter;

FIG. 33 is a perspective view of the counter;

FIG. 34 is a perspective view of a first ring member of the counter of FIG. 33;

FIG. 35 is a top view of the counter of FIG. 33;

FIGS. 36a to 36d schematically show in perspective view the operating principle of the counter;

FIGS. 37a to 37d schematically show from a top view the operating principle of the counter;

FIGS. 38a to 38c are schematic diagrams showing the principle of operation of the counter;

FIG. 39 is a perspective view of a dispenser including the counter;

FIG. 40 is a perspective view of a dispenser including the counter;

FIGS. 41a to 41d are perspective views of a limiting ring member;

FIG. 42 is a perspective view of a counter ring member adapted to work with the limiting ring member of FIGS. 41a to 41d; and FIGS. 43a to 43c are perspective views of the limiting ring member of FIGS. 41a to 41d coupled with the counter ring member of FIG. 42.

DETAILED DESCRIPTION OF THE PREFERRED EMBODIMENTS

Dispenser

To explain the invention, a brief overview of some features and operating principles of exemplary dispensers is initially provided. As used herein the term "dispenser" is intended to mean any device having a body suitable to receive a container holding a product and which has a mechanism to dispense the product from the container upon actuation.

Figure 8:
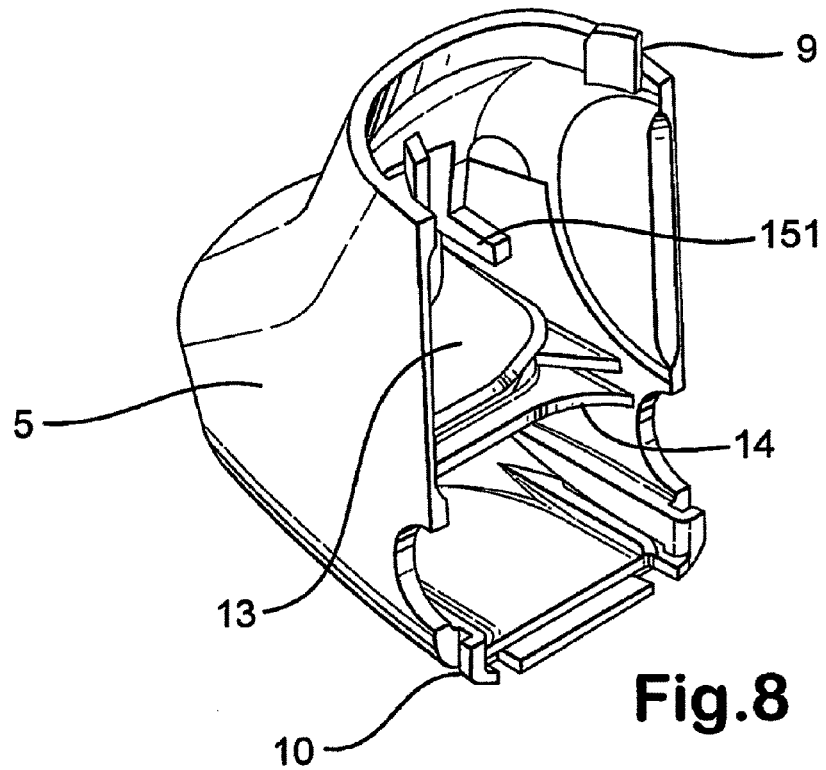
FIG. 8 is a view from the opposite direction of the front body part.

Referring first to FIGS. 1 to 4 of the drawings, the dispenser has a body 1 with a mouthpiece 2 and a pivoted mouthpiece cover 3. The mouthpiece is formed as an aperture 4 in a separate body part 5 clipped to a main body part 6 (although the skilled reader would appreciate that this formation could be made using a single-moulded piece). The main part 6 has upper and lower formations 7,8 (see FIG. 5a) and the mouthpiece part has upper and lower complementary formations 9,10 (see FIG. 8) which engage when the mouthpiece part is slid from below to engage with the main part. The separate body part 5 has cutaway 11 with respect to the main body part 6, to define an air inlet 12 exposed by the cover 3 when this is opened. A medicament can C is fitted to the body part 6. The medicament can C is also known as a substance source or a container. In preferred embodiments, the substance source C is a Pressurised Metered Dose Inhaler (pMDI). Immediately within the air inlet 12 is a guard 13 against fingers. It is backed up by strengthening flanges 14, which additionally guard the cam mechanism to be described in the next paragraph.

Figure 7:
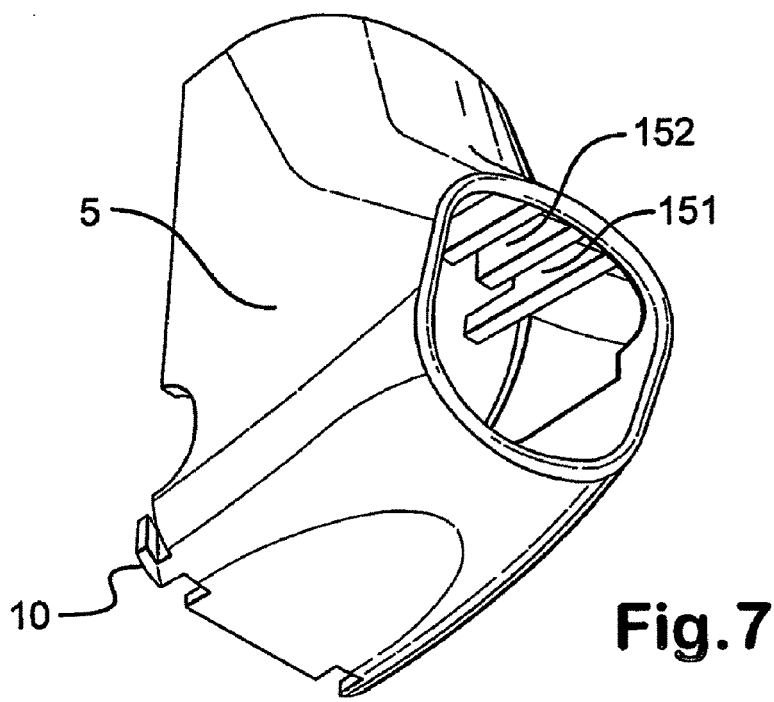
FIG. 7 is an oblique view from the front and below of a front body part of the dispenser.

Above the guard 13, a series of four ribs 151, 152 (in FIG. 7) extend and provide rigidity to the structure. The end ones 151 are longer and provide eventual stops for the flap of the actuation mechanism described below in the case of malfunction. The inner ones 152 act as flow restrictors to cause a pressure drop between the inlet 12 and the aperture 4 when the mechanism has been actuated, primarily to control the air flow rate through the device.

The cover 3 (see FIGS. 6, 12 & 13) is pivoted about an axis A low in the body 6 at the joint between the two body parts. Integrally moulded with the cover 3 is a C section shaft 21, via webs 22. The shaft carries a cam arrangement 23 (see FIG. 4), comprising two cam lobes 231 and 232, together with two fingers, a central one 24 and a outer one 25. The latter is integral with one of a pair of discs 26, between which are the cam lobes, the shaft is bearingly supported by part circular journals 27 in flanges 28 integrally moulded within the main body part 6 (see FIG. 5*a*). At the joint line between the two body parts 5 and 6 further coaxial scallops 29 are provided in the main body part 6 for the shaft 21.

The body parts 5,6, and the cover 3 (with the shaft and cam arrangement) in the described embodiments are of moulded polypropylene material, whereby they can be fitted together with a modicum of flexure.

The can C is held in an opening 31 at the upper end of the main body part 6, where the body part extends completely around a valve crimp portion CP of the can C.

Moulded inside the main body part, inwards of the opening are internal grooves 32 (FIG. 5*a*). A junction member 41 (see FIGS. 9, 10 & 11) is slidably accommodated in the body with the grooves 32 engaged by ribs 42 at its periphery. The junction member in this embodiment also is of moulded polypropylene. Centrally, the junction member has a socket 43 for accommodating a spout or an outlet stem S of the can C. The socket is continued by a flexible tube 44, which has a thin wall, kinkable location 45 and a nozzle end 46. This is in a movable outlet member 48 of the junction member. The main part 411 of the junction member 41 and the outlet member 48 are connected by a living hinge 49, in the form of two membranes 491,492 at respective sides of the junction member between lugs 561,562 and tabs 563, 564. The tabs are interconnected by a bar 52 having the nozzle aperture 53. Between the lugs 561,562 and on either side of the kinkable location 45 extend two followers 541,542, which are integral with the respective lugs 561,562 and are acted on by the cam lobes 231,232 (see FIG. 6), with the interposition of tongues 551,552 extending from the inside of the main body part 6 to react lateral action on the junction member from the cam arrangement. The followers 541,542 have radiused portions 56, centred on the hinge axis, with upper and lower valve travel stops 571,572.

The lugs 561,562 carry on their sides facing the same direction as the radiused portions 56, pairs of pivot clips 581,582 for pivotally locating the flap to be described below. One the same side of moulding a pair of sears 591,592 are provided on the tabs 563,564.

It was found in prior dispensers that a reliable longitudinal action on the junction member (i.e. motion along the longitudinal axis of the main body part 6, that is along the long axis of the main body part) was not provided. For example, the force from the cam did not always translate into a sufficient longitudinal movement of the junction member, which affected the dispensing of the medicament from a medicament source, or the action of the counter (described below—the counter is driven by the motion of the junction member).

In order to overcome this problem, we propose the features shown in FIGS. 5*a* to 5*e*, which show a preferred embodiment of the main body part 6 comprising a guide 15 along a back wall of the main body part. Two guide rails 20 are provided in the guide, and a protrusion 34 is provided at a lower portion of the base (extending from the back wall of the main body part).

Into the guide sits a cam follower 16, having a base 17. Two substantially rigid protrusions 18*a* and 18*b* extend from the base 17. Two guide rails 19*a*, 19*b* are disposed on the rear of the base 17. The cam follower 16 slides longitudinally within the guide 15 of the main body part 6, with the guide rails 20 and 19*a*, 19*b* interacting to retain the cam follower 16 in the guide 15. The cam lobes 231, 232 contact the underside surface of the protrusions 18, 18*b* and the junction member sits atop the upper surface of the protrusions 18*a*, 18*b*. As such, the cam lobes indirectly can apply a force to the junction member via the cam follower.

Since the protrusions 18*a*, 18*b* are substantially rigid, the whole cam follower moves longitudinally up and down as the cam arrangement imparts an upward force on the protrusion. In the preferred embodiment, the protrusions 18*a*, 18*b* remain rigidly in place and the cam follower slideably moves within the guide of the main body part. As such, this enables a more reliable longitudinal action of the junction member 41.

To aid with the manufacturing and assembling process, resiliently deformable clips 35 are disposed along the lower edge of the base of the cam follower. The clips are arranged to cooperate with the protrusion 34 in the main body part 6. During assembly, the cam follower is placed in the guide, and the resiliently deformable clips engage with the protrusion 34 in order to retain the cam follower in place (i.e. along the lower edge of the main body part). The clips and protrusion are configured such that the force generated by the cam as the mouthpiece is opened is much greater than the force which can be resisted by the clips. As such, the clips do not affect the operation of the cam follower during use.

The flap 61 (see FIGS. 14, 15 & 16) has a pivot axis B. At opposite ends of the axis, the flap has small thrust flanges 62, with pivot pins 60 set in from them. Inboard of the pins, two swellings 63 are formed. Each has a finger 64,65 extending obliquely down from it. One of the swellings has a spring loop 66 extending backwards, inwards and forwards again with its distal end 67 adjacent the swelling to which its proximal end 68 is attached. Set into the swellings 63 from the pins are apertures 69 formed from above and latches 70 extending below the apertures. These have latch surfaces 71 formed during moulding by projections through the apertures. The latches have cam surfaces 72. These are positioned so as to abut the sears 591,592 as the device is in the ready position. The sears then pass over the end of the cam surfaces and come to engage on the latch surfaces. The final feature of the flap is a tongue 73, which extends between the followers 541,542 to control air leakage as might otherwise occur.

The operation of the device will now be described.

Initially, the device is closed and the flexible members are relaxed. In others words the flap is in its upper, upstream position, as shown in FIGS. 3, 9 & 17 (4), and the outlet member 48 of the junction member is in its lower position. The flap is held in this position by its spring 66, bearing with it distal end 67 on an abutment 81 set in from the lug 562 and the flap 61 resting on crown 41*a* of the junction member. The outlet member 48 of the junction member is pivoted down, due to the tendency of the kinked location to straighten to its as moulded state. Its position is controlled by two fingers 82 projecting laterally from the bar 52 to abut with the cam lobes 231,232.

On opening of the cover, the cam lobes act via substantially rigid protrusions 18a, 18b of the cam follower 16 on the followers 541,542 of the junction member 41. The cam follower 16 slides within the guide 15 of the main body part 6, which lifts the junction member 41 against the internal spring (not shown) of the metering valve in the can, with displacement of stem S inwards of the can. As the cover 3 is rotated, the central finger 24 between the cam lobes engages with a notched projection 83 between the fingers 82 on the outlet member of the junction member. This action lifts the outlet member and closes the kinked location. Further lifting of the junction member opens the can's valve and a dose metered by the can's valve is released into the inlet end of the flexible tube. It is retained there by the kinked location acting as a closed valve.

Naturally, the dose is retained only whilst the outlet member 48 of the junction member is retained in the upper ready position to which it has been moved. This is achieved by the sears 591,592 running along the cam surfaces 72 of the flap 61 (see FIGS. 13, 14 and 16) and engaging with the latch surfaces 71. As the sears move into engagement, the latches 70 are moved back, rotating the flap down against the action of the spring 66. Once the sears clear the end of the cam surfaces, the spring 66 urges the latches fully under the sears. There is clearance for the outlet member 48 to continue to pivot further, until the central finger 24 passes on out of engagement with the projection 83. The device is now ready for inhalation.

Breathing in through the mouthpiece causes an air flow down through the air inlet 12, exposed on opening of the cover, and impinging on the flap 61. The flap is forced down against the action of the spring 66, releasing the sears 591, 592. The kink tube tends to straighten under the action of its own resilience and the pressure of the retained dose; thus the outlet member straightens through flexing of the hinges 491, 492 and the dose is released through the nozzle into the mouthpiece for inhalation, the nozzle traversing the mouthpiece aperture 4 as the dose is released.

The geometrical arrangement of the flap and the outlet member 48 can be seen in FIG. 17. The pivot axis B of the flap is spaced from the pivot axis D of the hingable part, with the point of engagement of the sears 591, 592 and latches 70 lying between parallel planes B' and D' passing through the axes B and D. The actual points of engagement lie to the flap side of a common plane P passing through the axes.

After use, the mouthpiece cover is closed. The rotation of the cam arrangement allows the junction member 41 to return down and the finger 24 passes the notched projection 83 as a result of cam surfaces on its reverse faces.

Should the kink tube have lost its resilience and be slow in opening, the finger 64, at the spring side of the flap pivot acts on a lug 85 moulded integrally with the outlet member's lug 563 and extending back past the hinge axis H. Thus the hingable part is moved to its open position.

A further eventuality is closure of the mouthpiece cover without inhalation. In this event, the finger 65 is engaged by the finger 25 to deflect the flap to its position in which the outlet member releases the dose. The spring 66 returns the flap after this movement of it (which of course occurs on closure even if the dose has been released by inhalation). Thus the device is returned to its initial position in which the plastics material resilient features are relaxed.

All the components of the device (excluding the can) are moulded of polypropylene, with the exception of the flap, whose spring dictates use of acetal copolymer.

Dispenser Cap Arrangement

As discussed above, tolerances in the length of the can and its spout and in other components with which the can is in contact mean that the can is not always seated in the same position relative to the body and a dispenser cap (not shown in FIGS. 1 to 4, but the cap surrounds the upper portion of the can and is coupled to the main body part 6). Since the can C is preferably seated so that the movement of the junction member is able to effect dispensing of a precise dose of medicament, there is need of a device to take up the variable height of the can C and/or its spout relative to the body.

We will now describe a dispenser cap arrangement, dispenser cap closure device and dispenser cap that has been designed to take up these tolerances and to allow the dispenser to work as intended.

With reference to FIGS. 18 to 21, a dispenser cap 91 has a plurality of openings 93 shaped and configured to engage with the protrusions 51 on the main body part 6 so that the dispenser cap and main body part remain affixed to one another. The lower open end 92 (the dispenser cap is shown upside down in FIG. 19) is shaped and dimensioned to receive the portion of the can that extends from the main body part when mounted in the main body part. The dispenser cap may also be shaped and dimensioned to receive a counter mechanism between the dispenser cap and the can. Before assembly with the dispenser cap closure device, the dispenser cap has an open upper end 94.

A plurality of teeth 101 is provided along an upper part of the dispenser cap. These teeth are configured to engage with the dispenser cap closure device to prevent rotation once the latter is in the correct position. Preferably, the teeth are provided at least partially around the circumference of the upper part of the dispenser cap. This will be described in more detail below. In preferred embodiments, there are three toothed sections around the circumference of the upper part of the dispenser cap, with gaps 95 between each section. Each toothed section has a lower ramped surface 102. Again, this will be described in more detail with reference to the dispenser cap closure device.

One or more protrusions 111 may also be provided along an upper part of the dispenser cap 91, which are arranged to engage with a correspondingly shaped portion of the dispenser cap closure device 120 to help retain the dispenser cap closure device in place once inserted into the end of the dispenser cap. In preferred embodiments, there is one protrusion 111 for each gap 95.

We will now describe a cap closure device (or 'bung') that works with the above-described dispenser cap 91 to close the end of the dispenser, and take up any tolerances in the length of the container.

With reference to FIGS. 22 to 24, the dispenser cap closure device 120 comprises an upper cap closure portion 121 and a lower cap closure portion 122. The upper 121 and lower 122 cap closure portions are separated by a bistable portion 130, 131, 132, 133. The upper cap closure portion 121 comprises a plurality of radial extending ribs or ridges 124 located on an underside or lower surface of the upper cap closure portion 121. The upper cap closure portion 121 is configured to engage with the upper open end 94 of the dispenser cap 91 and to close the upper open end 94 when the two are engaged. Protrusions in the form of radial extending ribs or ridges 124 are configured to engage with the teeth 101 on the upper lip of the dispenser cap 91 to prevent rotation of the dispenser cap closure device 120 when engaged with the dispenser cap 91. Furthermore, ridge 141 in the circumferential edge of the upper cap closure portion 121 is configured to engage with the protrusions 111 in the dispenser cap 91 to help retain the dispenser cap closure device in place once inserted into the end of the dispenser cap.

The lower cap closure portion 122 has a lower surface that is configured to contact the end of a canister C in the dispenser when the dispenser cap closure device is engaged with the dispenser cap. A plurality of protrusions 123 is also located radially around the lower cap closure portion. The protrusions 123 are configured to engage with the ramped portion 102 of the dispenser cap 91 as will be described below.

The bistable portion 130, 131, 132, 133 comprises a substantially rigid separator 130 and a resiliently deformable separator 131. The substantially rigid separator 130 is fixed to or integral with the upper cap closure portion 121. The resiliently deformable separator 131 is connected to the substantially rigid separator 130 at one end by means of a resiliently deformable joint 132, and the resiliently deformable separator 131 is connected to the lower cap closure portion 122 at the other end by means of a resiliently deformable joint 133.

The structure of the resiliently deformable separator 131 and resiliently deformable joints 132, 133 are configured to enable the dispenser cap closure device to switch or invert between a first stable form in which the bistable portion is extended (shown in FIG. 24a) and a second stable form in which the bistable portion is collapsed (shown in FIG. 24b). The upper 121 and lower 122 portions of the dispenser cap closure device are brought closer together in the second stable form (i.e. collapsed state). As can be seen in FIGS. 24a and 24b, an angle between the outer surface of the substantially rigid separator 130 and the outer surface of the resiliently deformable separator 131 is generally obtuse when the cap closure device is in the first stable form, and generally acute when the cap closure device is in the second stable form. The purpose of these two stable forms will be explained below.

The structure of the resiliently deformable separator 131 and resiliently deformable joints 132, 133 are configured such that the bistable portion, once in one of the two stable forms, remains in that stable form. A force applied to the upper 121 cap closure portion is required to switch the bistable portion from the first to the second stable form. Effectively, the force required to switch the bistable portion is proportional to the force required to deform the resiliently deformable separator 131 sufficiently such that the resiliently deformable separator 131 may pass through a substantially horizontal position (for example see FIGS. 23 and 24), which coincides with the shortest distance between the resiliently deformable joints 132, 133.

The dispenser cap assembly comprising the dispenser cap 91 and dispenser cap closure device 120 will now be described with reference to FIGS. 25a to 25f.

Figures 25A, 25B:
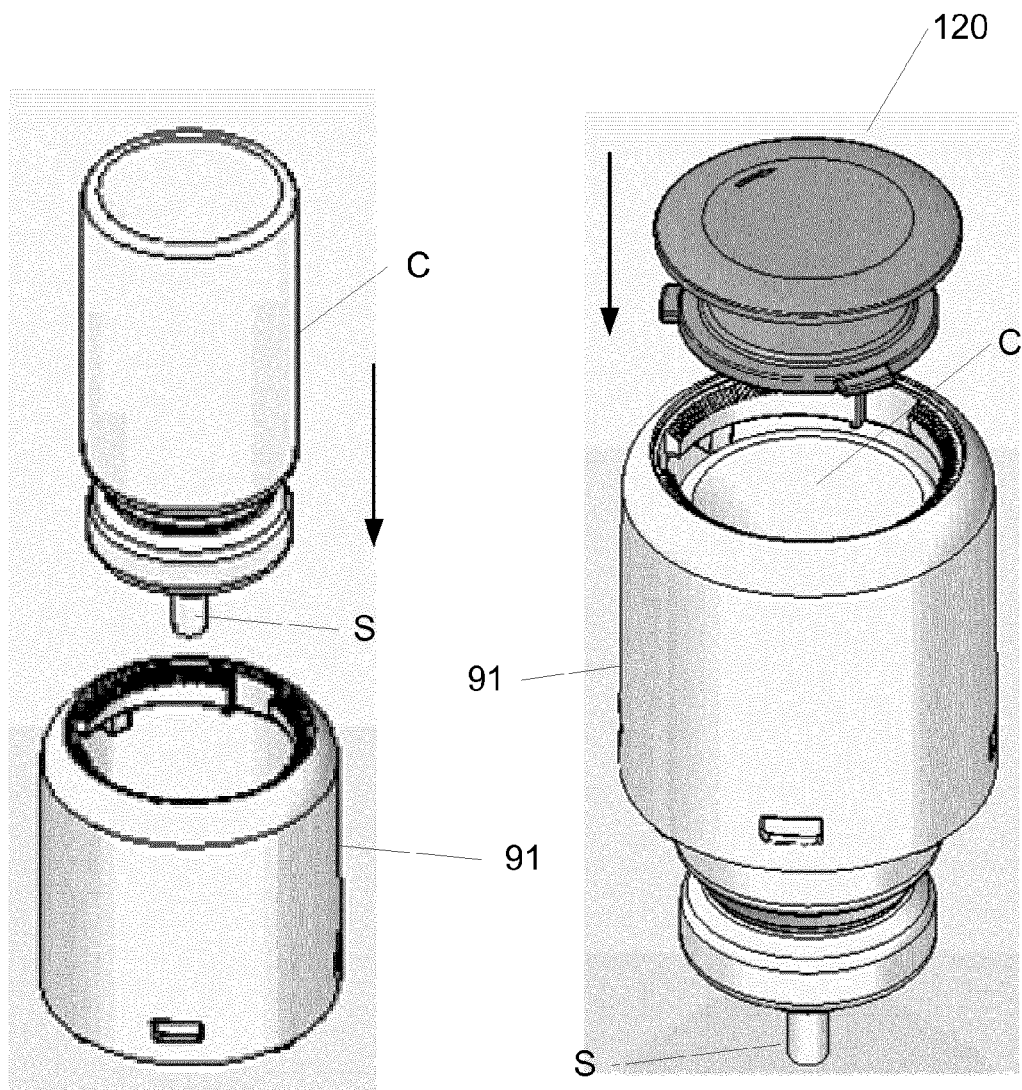

In FIG. 25a, the dispenser cap 91 is affixed to the main body part 6 of the dispenser (not shown). The upper open end of the dispenser cap is configured to receive the canister or container C, which is inserted through the upper opening and the spout S is seated in the junction member 41 in the body (not shown). Alternatively, the container C may be located before the dispenser cap 91 is affixed to the main body part 6.

Figure 25C:
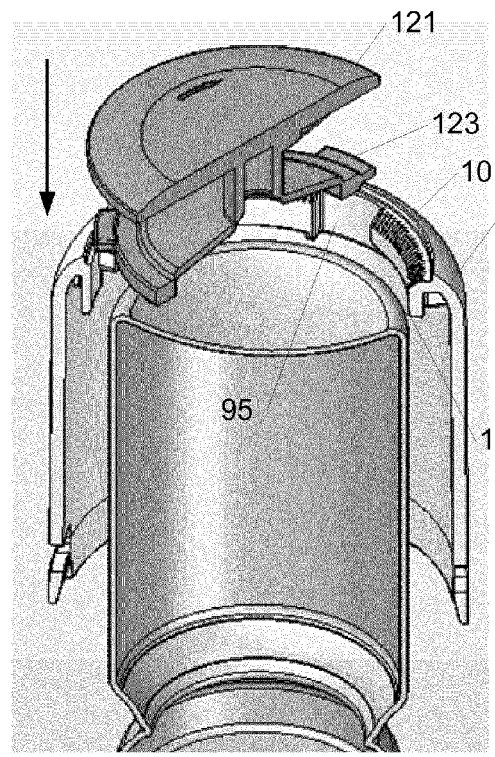
Figure 25D:
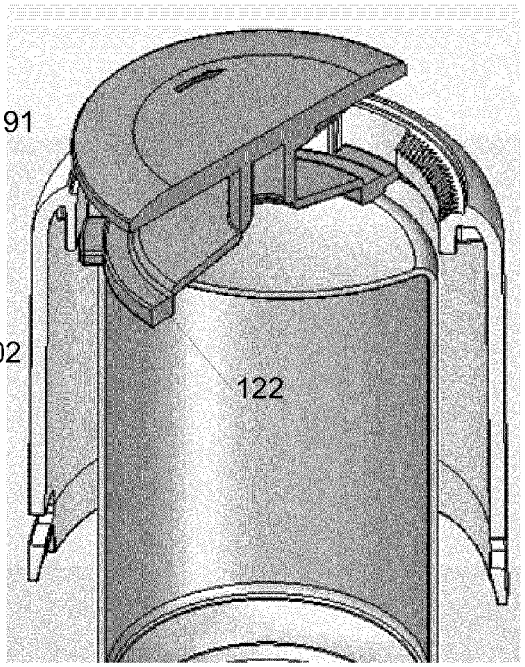

In FIGS. 25b, 25c and 25d (once the canister C is seated correctly), the dispenser cap closure device 120 (in its first stable form i.e. extended) is lowered into the upper open end of the dispenser cap 91 until the lower cap closure portion 122 is seated on the end of the canister C. In order for this to happen, each of the protrusions 123 on the lower portion 122 is aligned with a corresponding gap 95 between the toothed sections or the upper open end of the cap, which allows the cap closure device 120 to drop through to the canister C.

Figure 25E:
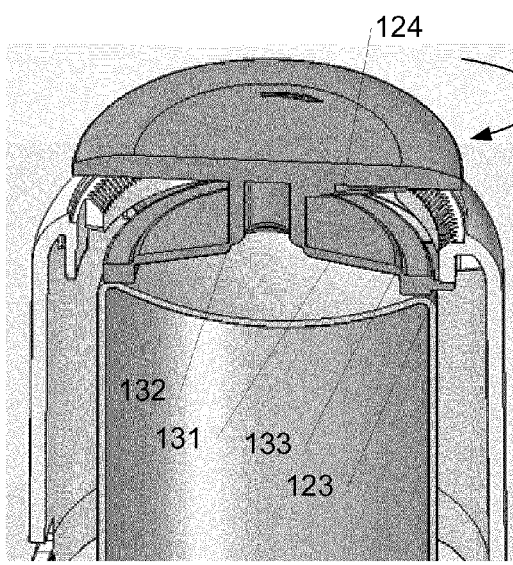

In FIG. 25e, the cap closure device 120 is rotated. In doing so, protrusions 123 engage with the ramped surface 102 under each of the toothed sections 91. Each of the ramped portions 102 are configured such that rotation of the cap closure device 120 in one direction drives the protrusions (and therefore the cap closure device) downwards towards the canister C, which draws the cap closure device 120 further into the dispenser cap 91. Furthermore, this downward drive pushes the lower cap closure portion 122 against the end of the canister C. Continued rotation beyond an initial contact between the protrusion 123, ramped portion 102 and the end of the canister will apply a positive force in a longitudinal axis of the dispenser against the canister.

The amount of rotation of the dispenser cap closure device 120 is dependent upon the length of the canister and/or its spout (i.e. the tolerances that are being negated), and whether or not a positive pressure on the canister is desirable. During assembly, the amount of rotation can be determined in advance of the dispenser cap closure device 120 being inserted (for example by measuring the height of the end of the canister relative to the body), and the assembly machinery could be configured to turn the cap closure device a specific number of degrees of rotation (assuming that the slope of the ramped portion 101 is known). Alternatively, a force measuring device could be used during assembly to measure a back force registering on the cap closure device 120 when it is being rotated (or an increase in torque required to turn the cap closure device), with the machine being configured to stop rotation when a registered force reaches a threshold or desired level.

Figure 25F:
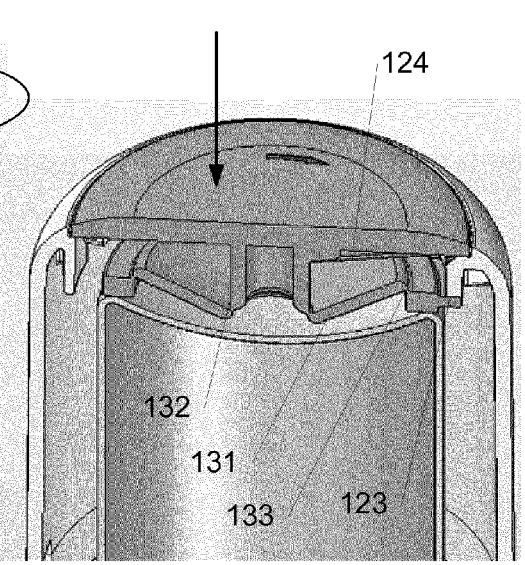

In FIG. 25f, and once the desired rotation of the cap closure device 120 has been reached, the upper portion 121 of the cap closure device is pushed down towards the canister such that it switches from the first stable form (i.e. extended) to the second stable form (i.e. collapsed). In the second stable form (as shown), radially extending ribs or ridges 124 on the underside of the upper portion 121 engage with the teeth portions 101 on the upper end of the dispenser cap 91. Such engagement between the ribs or ridges 124 and teeth portions 101 prevent further rotation (in either direction) of the cap closure device 120. Furthermore, protrusions 111 in the dispenser cap 91 engage with the ridge 141 in the upper cap closure portion 121 to help retain the dispenser cap closure device in place once inserted into the end of the dispenser cap. Since pressurised containers C generally have concave ends, the cap closure device 120 may extend below the original level of the lower portion 122 into the concave portion of such containers.

It will be noted that, since a force is required to deform the resiliently deformable separator 131 to overcome the horizontal position as described above (and therefore switch the bistable portion from the second to the first stable form), the dispenser cap closure device 120 is prevented from opening of its own accord. As such, once the dispenser cap closure device is in the second stable form, it is very difficult to undo or remove the device, which increases safety and security of the dispenser, since it makes it difficult for the user to tamper or take the dispenser apart.

In preferred embodiments, the dispenser cap 91 is transparent so that a counter can be read from beneath the surface.

Alternatively, a transparent portion defining a window may be provided on the dispenser cap. Preferably, the dispenser cap 91 is made from polypropylene (for example R7051-10N).

In preferred embodiments, the dispenser cap closure device 120 is made from polypropylene (for example ELTEX 200CA25).

Counter

We shall now describe a counter for counting the number of doses remaining in a medicament container, or the number of doses dispensed from a medicament container for use with the dispenser described above.

Drive Mechanism

The term "drive mechanism" is to be interpreted broadly as any means by which the dispensing of a dose from the medicament container is linked to a count being made by the counter. In described embodiments the dispensing of a dose will involve a vertical movement, e.g. of junction member 41, as described earlier. In the described preferred embodiment, this vertical movement is translated into an incremental rotation that is counted. In other embodiments the vertical movement that is translated into an incremental rotation of a counter may be the movement of a medicament container.

FIGS. 26a and 26b schematically show a dispenser 200 having a counter 203 and a drive mechanism 205. The counter comprises a second ring member 201 and a first ring member 202. The drive mechanism 205 is a pawl-and-teeth mechanism having a pawl-bearing member 204 (not shown in FIG. 26b) and a teeth-bearing member 206 (partially hidden from view in FIG. 26b). In this particular embodiment, the teeth-bearing member 206 is a hollow cylinder integral with the second ring member 201. The pawl-bearing member 204 extends fully around the teeth-bearing member 206. The reverse configuration may also be used, i.e. the pawl bearing member 206 may be integral with the second ring member 201. This arrangement is shown in FIG. 30.

Two pawls 208 are defined by a cutaway portion of pawl-bearing member 204. The pawls operatively engage with a ring of teeth 210 moulded on an outwardly facing surface of the teeth-bearing member 206 by means of inwardly extending protrusions on the tips of the pawls, as will be described in more detail later. A pair of arms 212a, 212b extend downwardly from the pawl-bearing member on either side of the metering valve assembly. The arms can be spring-loaded against, or affixed to, an upper portion of a junction member (hidden from view) (see also FIGS. 30c and 30d). The junction member moves vertically when a dose is dispensed. Alternatively the arms can be spring-loaded against, or affixed to, a moving container, e.g. a moving medicament container.

The action of lifting the junction member (which causes the release of a dose from a pressurised medicament container C) imparts an upward force on the pawl-bearing member 204 in a direction parallel to the vertical axis 214 of the dispenser 200. This results in frictional engagement between the pawl(s) and the teeth. In turn, the teeth-bearing member 206 and second ring member 201 are rotated (clockwise in this particular case) about the vertical axis 214 by an increment.

Once a dose is released and the mouthpiece cover is being closed or is closed, the junction and pawl-bearing members are able to move downwards to their original positions by, for example, an internal spring (not shown) of the medicament container. This downward movement also results in frictional engagement between the pawl-bearing and teeth-bearing members, resulting in a further clockwise rotation of members 206, 201 about the vertical axis 214 by an increment.

Taken together, these two increments of rotation define a "complete" incremental rotation of the second ring-like member 201 from a first to a second position.

FIG. 27a illustrates an exemplary drive mechanism 205 in which the ring of teeth 210 is disposed on an inwardly facing surface of the teeth-bearing member 206, with the pawl-bearing member 204 being disposed within its bore. It will be recognised that the pawl- and teeth-bearing members are in a reverse configuration compared to the configuration shown in FIGS. 26a and 26b, though the operating principle of the drive mechanism remains substantially the same.

Two pawls 402a, 402b, are integrally defined in the pawl-bearing member 204, by a cutaway portion of its body. Viewed from this perspective, each pawl extends toward the ring of teeth 210 in an annular plane of the pawl-bearing member 204, at about the same (but opposite) angle α, β. The second (lower) pawl 402b is offset in a circumferential direction relative to the first (upper) pawl 402a. The pawls each have a root end and a free end. A lip 408a, 408b, protrudes radially outwardly from each of the free ends, to operatively engage with the teeth.

The valve stem of the metering valve assembly inserts down through the clearance hole in the base of the pawl-bearing member 204 to rest on a shelf 420 in a stem block 422.

In operation, and viewed from this perspective, the pawl-bearing member 204 moves up and down, and rotates, relative to the teeth-bearing member 206. For convenience, the upward and downward movements of the pawl-bearing member 204 will be referred to as the 'count stroke' and 'return stroke', respectively. These terms are only used for convenience and are not to be construed as meaning that a count only occurs during the count stroke. It will be apparent to those skilled in the art (and from the following description) that a count may occur during the count stroke, return stroke or a combination of both strokes.

Figure 28A:
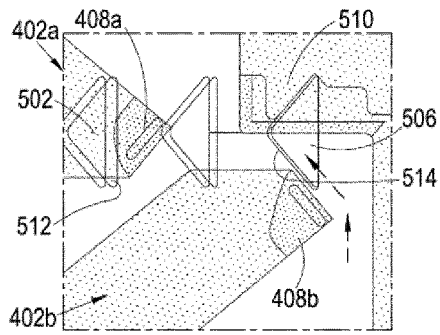
Figure 28B:
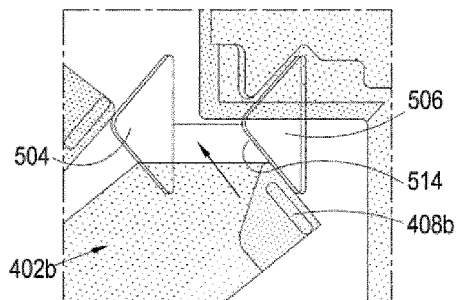
Figure 28C:
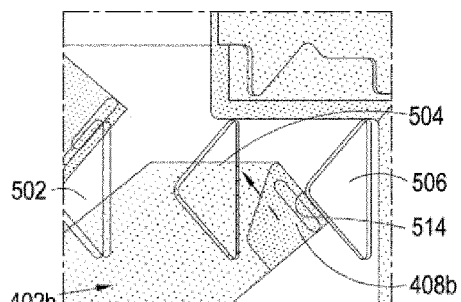
Figure 28D:
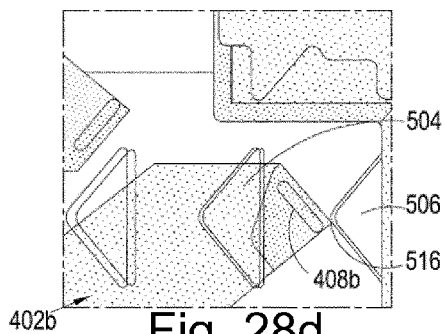

FIGS. 28a to 28d show a sequence of cross-sectional views of the drive mechanism during the count stroke. In FIG. 28a, the pawl-bearing member is at rest on the teeth by means of a protruding block 510. An upwardly directed force on the pawl-bearing member initially results in frictional engagement between the lip 408a of the first (upper) pawl 402a and a vertical face 512 of tooth 502. This action guides the pawl-bearing member substantially vertically upwards, until such a time as the lip 408b of the second (lower) pawl 402b engages with a lower, sloped face 514 of tooth 506 (FIG. 28b). This effects an upward diagonal movement, which proceeds until lip 408b reaches, and then surpasses, the apex 516 of tooth 506 (FIGS. 28c and 28d, respectively). At the same time, the first (upper) pawl 402a flexes slightly inwardly to allow lip 408a to pass over tooth 502 (FIG. 28c). Dashed arrows indicate the direction of movement.

FIGS. 29a to 29d show a sequence of cross-sectional views of the drive mechanism during the return stroke. Like elements to those of FIG. 28 are indicated by like reference numerals.

Figure 29A:
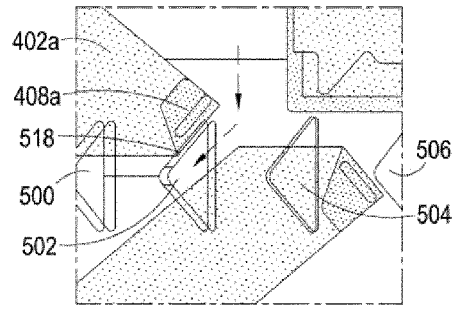
Figure 29B:
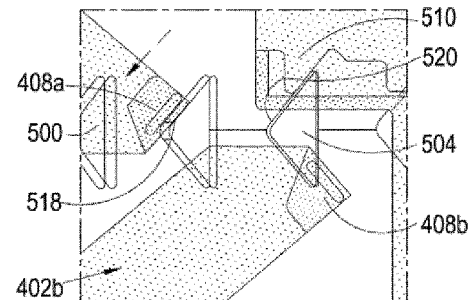
Figure 29C:
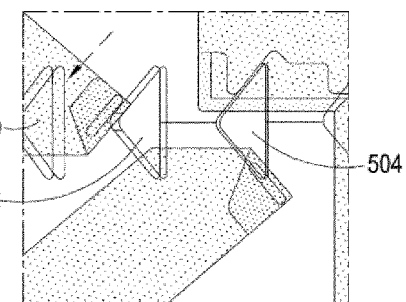
Figure 29D:
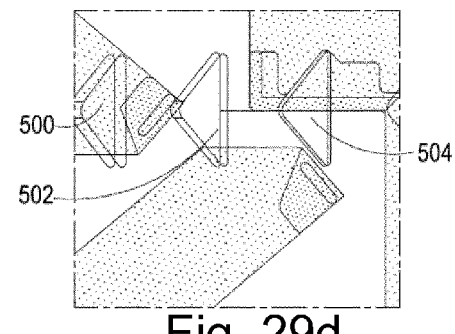

In FIG. 29a, which corresponds substantially to FIG. 28d, the lip 408a of the first (upper) pawl 402a moves vertically downwards until it frictionally engages with an upper, sloped face 518 of tooth 502, resulting in a downward diagonal movement. In FIG. 29b, the lip 408a has proceeded further down face 518, and block 510 now engages an upper, sloped face 520 of tooth 504. This time the second (lower)

pawl 402b flexes slightly inwardly to allow lip 408b to pass over tooth 504. This proceeds until the pawl-bearing member again comes to rest on the teeth (FIGS. 29c and 29d). FIG. 29d corresponds substantially to FIG. 28a, but rotated by one tooth, i.e. from tooth 506 to tooth 504.

Referring to FIG. 27b, this shows a side profile of the pawls 402a and 402b and the lips 408a and 408b. Each lip comprises a driving engagement face 440, which contacts a tooth during a driving engagement of that lip 408. Each lip also comprises a sliding engagement face 430, which enables a lip 408 to contact and lift over a tooth without engaging the tooth. The large arrows denote the faces of the pawl lips that contact teeth during one of the strokes. The opposite faces (shown without arrows) contact teeth during the other stroke. The angle γ (that is the angle of the slope of the sliding engagement face 430 of the lip with respect to a vertical axis in the figure) must be sufficiently large enough to enable the lip 408b lift away and ride over the teeth when lip 408a is engaged with a tooth (i.e. driving engagement face 440a is in contact with, and drivingly engaged with a tooth). An angle greater than 15° is preferred. If the angle is less than 15°, the pawl may not lift above the tooth.

FIG. 30a illustrates a preferred embodiment of the drive mechanism 205 in which the ring of teeth 210 is disposed on an outwardly facing surface of a teeth-bearing member 206, which is placed within the bore of the pawl-bearing member 204. In this embodiment, the teeth-bearing member is a yoke (also known as a counter driver), and the pawl-bearing member is the second ring (or units ring) of the counter.

Two pawls 402a, 402b, are integrally defined in the pawl-bearing member 204, by a cutaway portion of its body. Viewed from this perspective, each pawl comprises two arms extending toward the ring of teeth 210 in an annular plane of the pawl-bearing member 204. The second pawl 402b is offset in a circumferential direction relative to the first pawl 402a. A lip 408a, 408b, protrudes radially outwardly from the point at which the two arms meet, to operatively engage with the teeth.

FIG. 30b shows a side profile of the pawls 402a, 402b. The numerals of FIG. 27b refer to like features of FIG. 30b. As with FIG. 27b, the angle γ (i.e. the angle of the sliding engagement face 430 from the vertical of the drawing) must be sufficiently large enough to enable the sliding engaging face 430 to lift up and ride over the tooth (not shown). For example, the angle is preferably larger than 15°. More preferably, the angle is approximately 45°. It will also be noted that the orientation of the first pawl 402a is reversed to that shown in FIG. 27b. It will be appreciated that the engaged pawl (i.e. the pawl in driving engagement with the tooth) experiences a compression force that forces the pawl towards the toothed surface during engagement.

In operation, and viewed from this perspective, the teeth-bearing member 206 moves up and down (driven by the actuation of the junction member as described above), causing the pawl-bearing member 204 to rotate relative to the teeth-bearing member 206. For convenience, the upward and downward movements of the teeth-bearing member 206 will be referred to as the 'count stroke' and 'return stroke', respectively.

In preferred embodiment of the counter, the pawl-bearing member (i.e. the second ring member, or units ring of the counter) is provided with two sets of pawls, located substantially 180° apart around the pawl-bearing member. The second set of pawls is not shown in FIG. 30a.

FIG. 30c shows a yoke 206 (or teeth-bearing member or counter driver) according to preferred embodiments. In this preferred embodiment, the yoke comprises a notched portion 220, which is shaped and dimensioned to slideably engage with correspondingly shaped protrusions (230) on the inside of the main body part 6 (see FIG. 30e). Only one protrusion 230 is shown in the figure. In preferred embodiments, a second protrusion is positioned on the inside surface opposite protrusion or rail 230, which corresponds with an appropriately positioned notch on the yoke 206. These notches and protrusions allow the yoke to move longitudinally within the main body and prevents the yoke from rotating in the same axis of the counter rings. As such, this provides a more reliable count, as there is no rotational movement of the yoke (which would cause the counter mechanism to over count or under count). Whilst we describe feature 230 as a protrusion, the feature may also be considered a rail. FIG. 30e also shows a recess 240, into which the arms of the yoke 206 are slideably arranged to allow movement in the longitudinal axis of the main body part 6.

The preferred yoke 206 is also provided with protrusions 222a and 222b, which are shaped to engage with correspondingly shaped holes 450a and 450b in the junction member 41 (see FIG. 30d). In such embodiment, the yoke is coupled to the junction member via the protrusions and holes such that longitudinal motion of the junction member produces longitudinal motion of the yoke (which in turn drives the counter mechanism).

Figure 31A:
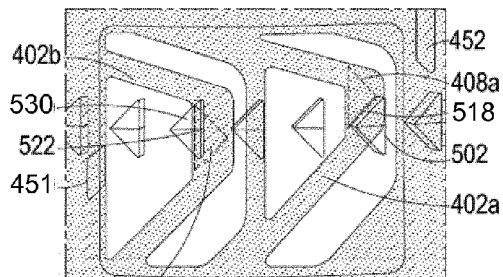

FIGS. 31a to 31d show a sequence of cross-sectional views of the preferred drive mechanism during the count stroke. In FIG. 31a, the teeth- and pawl-bearing members are at rest. An anti-slip bar 451, comprising a protrusion extending from the inner surface of the pawl-bearing member, is in an engaged position that is sufficiently in line with the teeth to prevent non-count rotation of the pawl-bearing member (i.e. rotation of the pawl-bearing member in an opposite direction to that of the pawl-bearing member during a count). The anti-slip bar 451 is configured to prevent relative rotation between the teeth-bearing member and pawl-bearing member in a non-count direction by blocking motion of the pawl-bearing member. The bar extends sufficiently from the inner surface of the pawl-bearing to hit one of the teeth, but not the outer surface of the teeth-bearing member.

An upwardly directed force on the teeth-bearing member initially results in an edge of the lip 408a coming into frictional engagement with a sloped face 518 of tooth 502 and moves the anti-slip bar 451 out of the path of the teeth to permit rotation. Further upward movement of the teeth-bearing member causes rotational movement of the pawl-bearing member (towards the left of the figure). At the same time, the inner non-vertical surface of lip 408b (shown as the arrowed surface in FIG. 30b) contacts a vertical non-leading edge 522 of tooth 530, which causes the pawl 402b to lift away from the plane of the teeth, and permits the pawl 402b to ride over the tooth without engagement.

Rotational movement of the pawl-bearing member continues until lip 408a and surface 518 no longer contact. At this point, lip 408b has cleared tooth 530, and falls back to the plane of the teeth by virtue of the pawl arms being resiliently deformable. Further upward motion of the teeth-bearing member has no further effect on rotation of the pawl-bearing member. However, a second anti-slip bar 452 (configured similarly to anti-slip bar 451) is brought into the path of the teeth to prevent backward (i.e. non-count) rotation of the pawl-bearing member.

FIGS. 32a to 32d show a sequence of cross-sectional views of the drive mechanism during the return stroke. Like elements to those of FIG. 31 are indicated by like reference numerals.

Figure 32A:
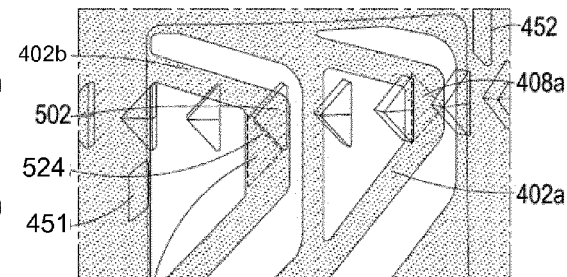
Figure 31B:
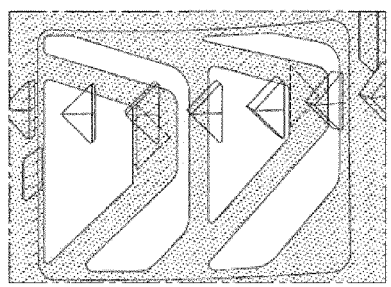
Figure 32B:
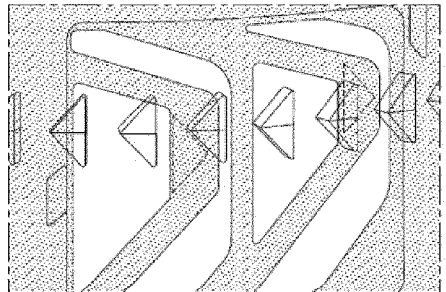
Figure 31C:
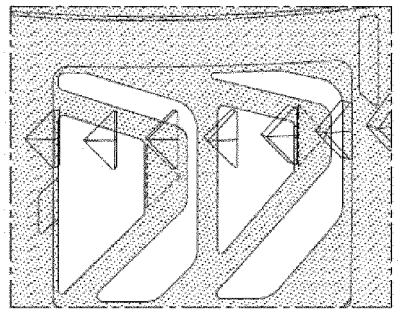
Figure 32C:
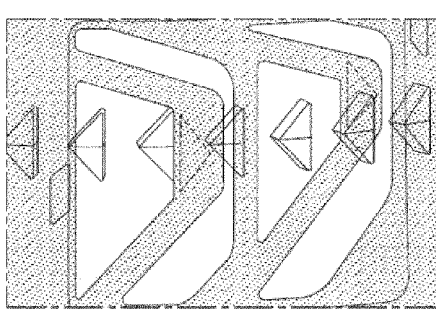
Figure 31D:
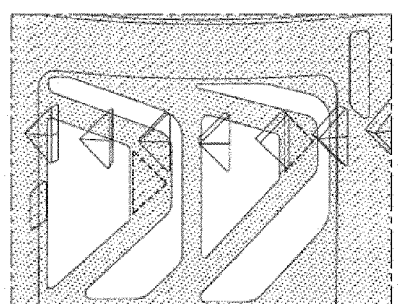
Figure 32D:
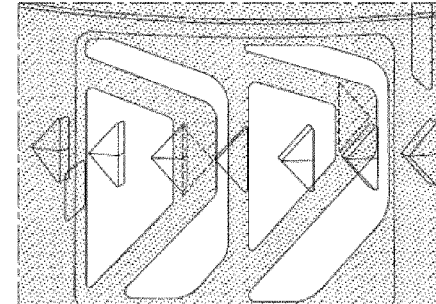

In FIG. 32a, which substantially follows FIG. 31d, the teeth-bearing member is lowered until lip 408b of the first pawl 402b frictionally engages with a lower, sloped face 524 of tooth 502 (simultaneously, the second anti-slip bar 452 is moved from the path of the teeth). Further downward movement of the teeth-bearing member causes rotational movement of the pawl-bearing member by virtue of the face 524 and lip 408a being frictionally engaged.

Face 524 proceeds further down lip 408b. At the same time, the inner non-vertical surface of lip 408a contacts a vertical non-leading edge of a tooth, which causes the pawl 402a to lift away from the plane of the teeth, and permits the pawl 402a to ride over the tooth without engagement.

Rotational movement of the pawl-bearing member continues until lip 408b and surface 524 no longer contact. At this point, lip 408a has cleared the tooth over which it was riding, and falls back to the plane of the teeth by virtue of the pawl arms being resiliently deformable. Further downward motion of the teeth-bearing member has no further effect on rotation of the pawl-bearing member. However, the first anti-slip bar 451 is brought back into the path of the teeth to prevent backward rotation of the pawl-bearing member.

Although the foregoing discussion describes the case where the pawl-bearing member rotates about an axis (i.e. rotates relative to the dispenser as a whole), it is equally possible that the teeth-bearing member could rotate if the teeth-bearing member were integral with the second ring member and the pawl mechanism were integral with the counter driver (or yoke). Naturally it is also possible that the teeth could point in either direction around the circumference of the teeth bearing member.

It will be appreciated that a rotational displacement need not be performed by way of two engagements (though this may be beneficial), nor need it comprise vertical and rotational movement. For example, a drive mechanism providing purely rotational motion, in other words without vertical movement, could also be used.

Counter Mechanism

FIGS. 33 to 40 provide various depictions of the counter in more detail.

Turning first to FIG. 33, the counter 203 is comprised of second ring member 201 and first ring member 202. The ring members are rotatably and coaxially arranged about the central axis 214, encircling the container of the dispenser. The first ring member is arranged substantially flush on top of the second ring member, with their outer circumferential surfaces being aligned so as to form a substantially continuous surface interrupted only by a hairline 720 where the two ring members meet. A pawl-bearing member 205 of a drive mechanism is integral with the second ring member 201.

A first row of numbers 701 ('8', '9', '0', '1') is displayed on the second ring member 201, with a second row of numbers 702 ('0', '1', '2', '3', '4') and a third row of numbers 703 ('1', '1', '1') displayed on the first ring member 202. For clarity, only some of the numbers are depicted. A coupling mechanism 700 comprising an arm 704, a series of equally spaced protrusions 705, and a deflector 1002 can also be seen. The coupling mechanism allows the second ring member 201 to be coupled to the first ring member 202, so that they can be rotated in tandem by the drive mechanism when coupled, as detailed below. The spaced apart protrusions 705 are formed on an inner surface of the first ring member 202, and in this particular case extend only half way around the axis.

It will become clear in due course that, depending on the counting scheme used, multiple arms and/or deflectors may be provided. However, for purposes of clarity only, only one arm and/or deflector is depicted in these figures. In preferred embodiments of the counter, the coupling mechanism 700 comprises four arms 704 equally spaced around the upper radial surface of the second ring member.

Referring now to FIG. 34, the arm 704 is integrally formed with an annular band 706 that fixedly sits in a recess of an upper radial surface 716 of the second ring member 201. Alternatively, the arm 704 can be directly mounted on, or integral with, upper radial surface 804. The arm 704 has a slotted body 712 which extends arcuately with approximately the same curvature of second ring member 201, and an upwardly extending contact end 710.

With reference to FIG. 35, being a view of FIG. 33 from above, the first ring member 202 (shown as a shaded ring) is slidably mounted on an outer portion of the upper radial surface 804 of the second ring member (shown as a blank ring, part of which is hidden from view underneath the shaded ring). From this perspective, it is apparent that the thickness of the first ring member 202, designated 't2', is about a third of the thickness of the second ring member 201, designated 't1'. The thickness of the second ring member 201 may be consistent along its height or it may be tapered, it being thickest at its upper radial surface 804. The dashed line represents an imaginary boundary line between the arm 704 and the spaced apart protrusions 705 formed on the inner surface 902 of the first ring member 202.

FIGS. 36 and 37 show, in a series of corresponding perspective and downward views respectively, the operation of the coupling mechanism.

Figure 36A:
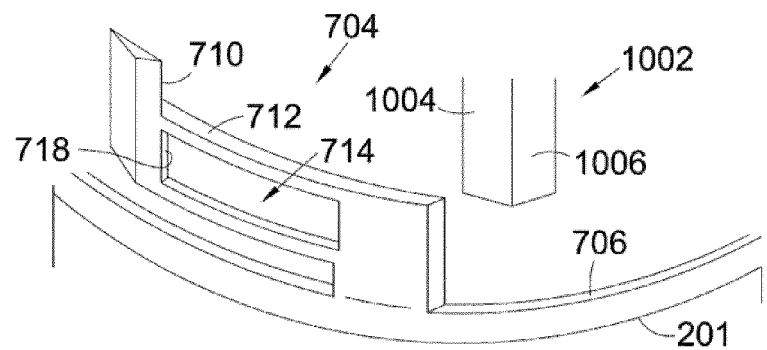
Figure 36B:
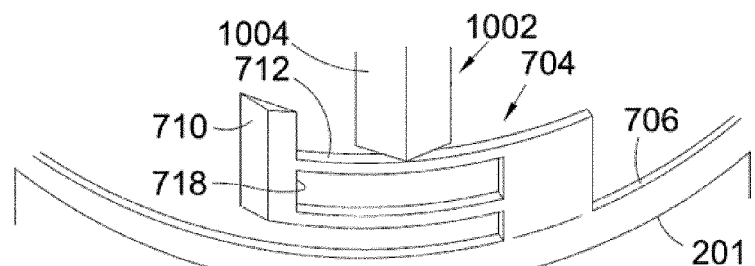
Figure 37A:
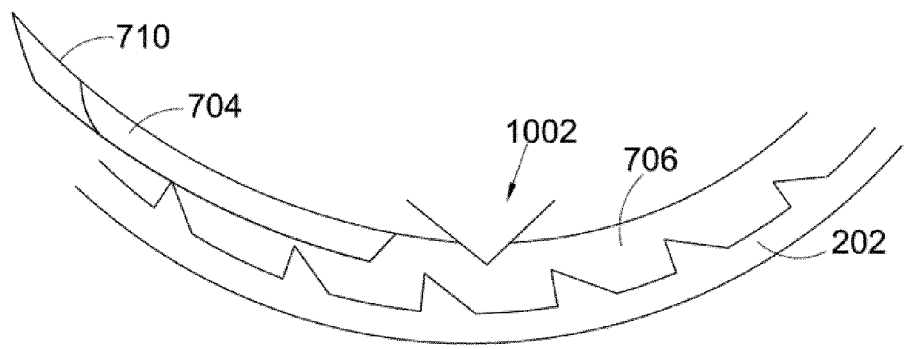
Figure 37B:
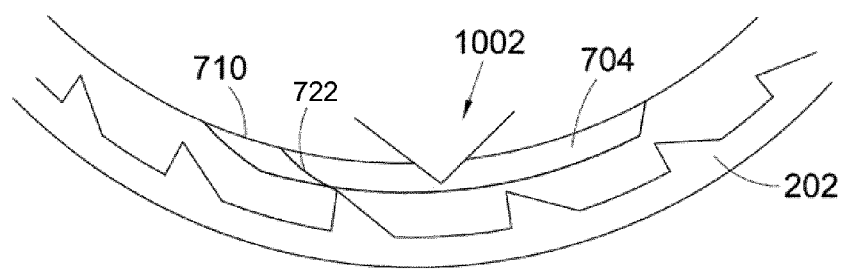

FIGS. 36a and 37a show the arm 704 at a distance from the deflector 1002. In FIGS. 36b and 37b, the second ring member 201 and arm 704 are rotated in an anticlockwise direction, so that the upwardly extending contact end 710 of the arm 704 approaches the deflector 1002. The deflector 1002 is fixed to the container, or alternatively to an upper portion of a housing of the dispenser and/or to a sleeve surrounding the container. The deflector extends downwardly only to such an extent that the body 712 of the arm is allowed to pass underneath unimpeded.

Figure 36C:
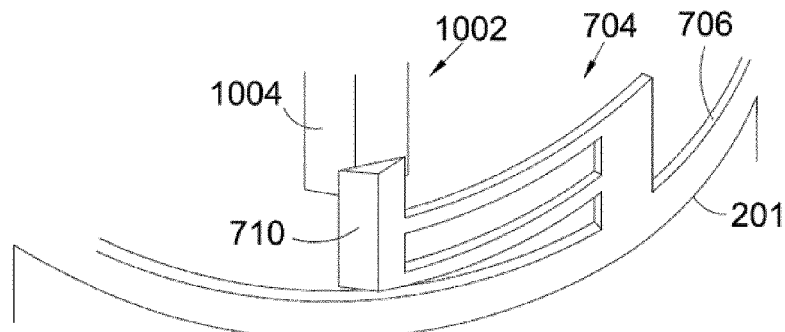
Figure 36D:
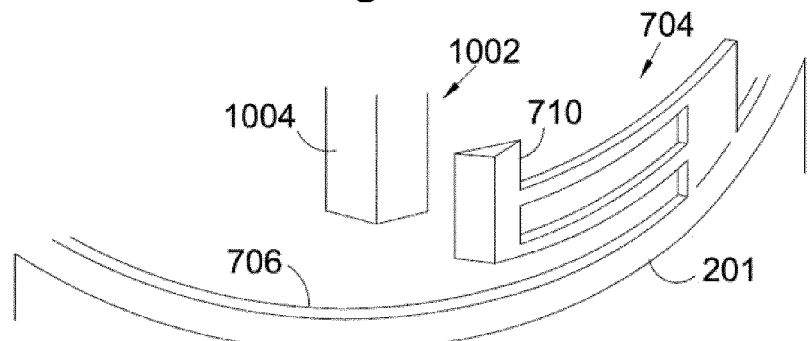
Figure 37C:
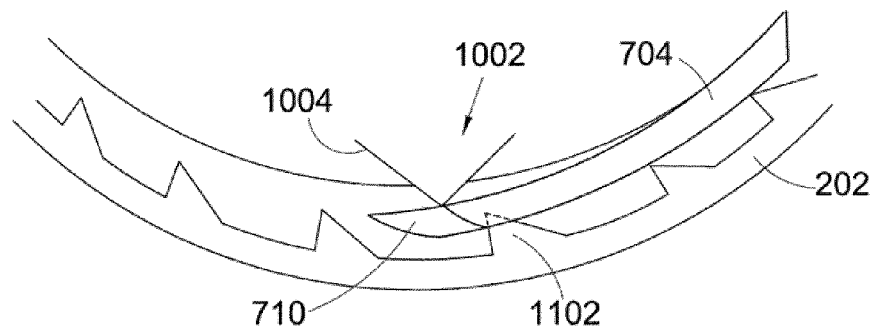
Figure 37D:
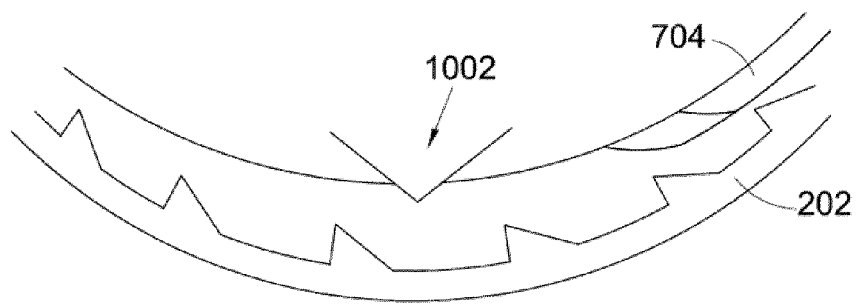

As the contact end 710 reaches an inclined face 1004 of the deflector 1002, the arm 704 is deflected outwards (FIGS. 36c and 37c). At this point a trailing end 718 of the slot 714 catches one of the teeth 1102, thereby causing the first ring member 202 to be pulled along. When the contact end descends down face 1006 of the deflector, the tooth 1102 is released by the trailing end of the slot and the arm returns to its non-flexed position (FIGS. 36d and 37d). As seen in FIG. 37b, the upwardly extending contact end 710 of the arm 704 may have a face 722 complementing the inclined face 1004 of the deflector 1002, to allow for a smooth deflection. Preferably the contact end 710 is pointed so that when it reaches the apex of deflector 1002, the arm can immediately begin to return to its non-flexed position.

As shown herein, the slot 714 forms an engaging portion of the arm 704, but it is recognized that any suitable engaging means could be used such as a hook. Accordingly, recesses could be formed in the first ring member instead of protrusions.

The arm 704 is sufficiently flexible to permit a radially outward deflection (that is, towards the protrusions) when encouraged to do so, but also resilient enough to return to its original position. The counter may additionally comprise a second deflector that functions to move or deflect the engagement means (e.g. arm 704) back to its non-flexed position. This second deflector may, for example, be fixed to, or integral with, an inner surface of the first ring member 202. Additionally the first ring member is preferably slidably mounted on the second ring member so as to resist rotation when there is no engagement between the arm and the teeth.

An exemplary counting scheme for a counter configured for 200 doses is now described with reference to FIGS. 38*a* to 38*c*, which show the second and first ring members in three different display positions. For convenience, the ring members 201, 202 are shown as flat rings. Also shown are the protrusions 705, the deflector 1002, a window 1202 through which the counter can viewed, and a display cover element 1204.

In this particular scheme, the second ring member 201 has a first row of numbers comprising four repeated sets of consecutive integers '0' to '9', i.e.:

01234567890123456789012345678901234567 89.

Each set of integers covers a quarter turn of the second ring member 201, and here represents the 'units' digits of a count.

The first ring member 202 has second and a third rows of numbers. The second row comprises two repeated sets of consecutive integers '1' to '9' separated by a '0', while the third row comprises ten '1's optionally followed by a '2', e.g.:

11111111112
12345678901234567890

Similarly, each set of integers of the second and third rows covers a quarter turn of the first ring member 202. Here, the second row represents 'tens' digits, and the third row represent 'hundreds' digits of a count. Also shown on the first ring is a warning symbol in the form of an exclamation mark '!'.

In practice it may be more convenient to start a count at say '199' rather than '200', to avoid having to rotate the first ring member 202 initially. The integers forming the number '200' seen to the right of the window 1202 in FIG. 38*a* may therefore be omitted. Thus, when the second and first ring members are initially aligned in a housing of the dispenser, the first, second and third rows cooperatively display the number '199' (when read from top to bottom):

- - - - - - - - - - - - - - - - - - - - - - - - - - - - -1111111111
- - - - - - - - - - - - - - - - - - - -01234567890123456789
01234567890123456789012345678901234567 89 where '-' indicates a blank space.

For each of the first nine dispensed doses, the second ring member is rotated anticlockwise by an increment, i.e. counting down from '9' to '0', until the number '190' is displayed. Then for the tenth dispensed dose, the second and first ring members are coupled by means of the coupling mechanism so that the ring members are rotated in tandem by an increment. This results in the number '189' being displayed through window 1202. For the subsequent nine dispensed doses, the second ring member is again rotated anticlockwise by increments until the number '180' is displayed. For the twentieth dispensed dose, the coupling mechanism is again engaged, so that the second and first ring members are rotated in tandem by an increment and the number '179' is displayed through the window 1202.

FIG. 38*b* shows an intermediate count position, in which the number '72' is displayed. In this position, the third row has run out and a blank space appears instead. Alternatively, the blank space may be filled with indicia other than numbers, such as colours.

As the container becomes exhausted, e.g. below ten doses remaining, the second row of numbers can be replaced by an exclamation marks '!' or other warning indicators. Preferred warning indicators for this purpose are colours (e.g. red). Once the final dose has been dispensed (FIG. 38*c*), a cover element 1204 that is preferably attached to the first ring member and has therefore rotated at the same rate, is aligned with the window 1202. This occludes from view any indicia. The cover may have the word 'EMTPY' written on it for example.

Further actuations of the dispenser may still result in the second ring member 201 being rotated. However, since the teeth are disposed only half way around the first ring member 202, the coupling mechanism can no longer be engaged, i.e. there are no teeth for the slot of the arm to engage with. Thus, no further rotations of the first ring member 202 can be effected, so that the display cover element 1204 remains in place even if the second ring is still rotated by further actuations of the dispenser.

In preferred embodiments the protrusions (e.g. teeth) are equally spaced apart. Particularly preferably the protrusions only extend three quarters of the way (e.g. about 270°) around the ring member, still more preferably the protrusions only extend between a quarter and half way (e.g. about 90°, 108° or 180°, or any angle therebetween) around the ring member.

It will be apparent that the number of deflectors and/or arms (not shown in FIG. 38) will depend on the implemented counting scheme. In FIG. 38 for example, where the second ring member 201 has a first row of numbers comprising four repeated sets of consecutive integers '0' to '9' such that each set covers a quarter turn of the second ring member 201, and where one deflector 1002 is provided, the counter will have four arms spaced at 90 degree intervals. Of course, other configurations will also be possible. For example, where the second ring member 201 has a first row of numbers comprising two repeated sets of consecutive integers '0' to '9' such that each set covers half a turn of the second ring member 201, and where one deflector 1002 is provided, the counter will have two arms spaced at 180 degree intervals. Alternatively, it may be possible to have a single arm and multiple deflectors 1002 spaced at intervals, or multiple arms and deflectors.

FIGS. 39 and 40 are perspective views of a dispenser including the counter. In contrast to FIGS. 26*a* and 26*b*, the pawl-bearing member rather than the teeth-bearing member is integral with the second ring member 201. Also visible in FIG. 39 is a strip of colour following the third row of numbers 703. FIG. 40 shows how a count ('119') can be viewed through a window 1202 of a housing 1402 of the dispenser.

Limiting Mechanism

Preferably, the counter comprises a limiting mechanism, which prevents free rotation of the first ring member. That is, to prevent over-rotation of the first ring member when the first ring member is driven to register a count. Over-rotation of the first ring member during a count leads to an incorrect dosage value being displayed. The limiting mechanism may also be configured to limit free rotation in a reverse count direction, again to prevent an incorrect dosage value being displayed. Preferably the limiting mechanism not only limits free rotation in the reverse count direction, but also prevents any rotation in the reverse count direction.

It has been found that some limiting mechanisms do not always reliably prevent over- or back-rotation of the first ring member. For example, some limiting mechanisms 1506 acts in the vertical direction (i.e. a direction parallel to the longitudinal axis of the dispenser and counter rings). It has been found, however, that manufacturing tolerances in each of the components acting or in the vertical path may stack up beyond a value that is acceptable. As such, the limiting mechanism may not always limit rotation of the first ring member.

We have therefore appreciated the need for an improved limiting mechanism that may provide a more reliable action.

The limiting mechanism will now be described with reference to FIGS. 41 to 43, in which FIGS. 41a to 41d are perspective views of a limiting ring member, FIG. 42 is a perspective view of a counter ring member (for example a first ring member) adapted to work with the limiting ring member of FIGS. 41a to 41d, and FIGS. 43a to 43c are perspective views of the limiting ring member of FIGS. 41a to 41d coupled with the counter ring member of FIG. 42.

The first ring member 1610 is rotatably and coaxially arranged with a second ring member 201 about a central axis 214 as described above (and as shown in FIGS. 33 and 34). For clarity, the second ring member 201 is not shown in these drawings.

As with the embodiments described above, the first ring member is arranged substantially flush on top of the second ring member, with their outer circumferential surfaces being aligned so as to form a substantially continuous surface interrupted only by a hairline where the two ring members meet. A pawl-bearing member 205 of a drive mechanism is integral with the second ring member 201.

The limiting ring member 1602 is coaxially arranged with the first ring member 1610. The limiting ring member 1602 sits atop the first ring member 1610, with edge 1650 on the limiting ring member 1602 contacting and resting on the edge 1652 of the first ring member 1610.

In use, the limiting ring member 1602 does not rotate. The limiting ring member comprises a deflector 1604 to deflect arm 704 on the second ring member 201 to engage with protrusions 1616 on the inside surface of the first ring member 1610 in the manner as described above with reference to FIGS. 36 and 37. As can be seen, the limiting ring member has a gap 1618 in its outer wall to enable the arm 704 to deflect outwards. A sloped edge on the trailing boundary of the window 1618 engages with an edge of the arm 704 to push the arm 704 away from the teeth 1616 after the arm has engaged with the teeth 1616. This ensures that unwanted further engagement of the tens (first) ring member (which would lead to an incorrect dosage value being displayed) does not happen.

The limiting ring member 1602 further comprises a limiting mechanism 1606 which comprises an engaging portion 1620 arranged to act radially (inwardly and/or outwardly) with respect to the first ring member 1610 to contact the first ring member to limit free rotation of the first ring member relative to the limiting member about the coaxial axis. The engaging portion 1620 is preferably a tooth.

The purpose of the limiting mechanism is to prevent free rotation of the first ring member. That is, to prevent over-rotation of the first ring member when the first ring member is driven to register a count. Over-rotation of the first ring member during a count leads to an incorrect dosage value being displayed. The limiting mechanism may also be configured to limit free rotation in a reverse count direction, again to prevent an incorrect dosage value being displayed. Preferably the limiting mechanism not only limits free rotation in the reverse count direction, but also prevents any rotation in the reverse count direction.

The engaging portion 1620 is preferably located on a base or panel 1622. One end of the panel 1622 is fixed to the limiting ring member 1602 at location 1626. The other end of the panel 1622 comprises a floating end. The panel is flexibly fixed at location 1626 to the limiting ring member 1602 such that the floating end of the panel may swing radially with respect to the first ring member. As such, the floating end is moveable radially inwardly and outwardly with respect to the first ring member. Preferably, the engaging portion 1620 is located at the floating end of the panel. As such, radial movement of the floating end enables the engaging portion to come into contact with a surface of the first ring member. The engaging portion 1620 may be configured to contact an inner or outer surface of the first ring member 1610.

Preferably, the engaging portion 1620 contacts an inner surface of the first ring member 1610.

The inner surface of the first ring member 1610 is preferably also provided with an engaging portion 1630, which preferably comprises a plurality of teeth that are shaped to co-operate with the engaging portion 1620 of the limiting mechanism. The engaging portion teeth 1630 are preferably ratchet teeth or teeth in the shape of a saw-tooth formation.

When the dispenser is not in use (i.e. no count operation is being performed), engaging portion 1620 rests between neighbouring teeth 1630 of the first ring member 1610.

When the first ring member 1610 is required to move in a count direction (i.e. to register a count when deflector 1604 deflects arm 704 on the second ring member 201 to engage with protrusions 1616 on the inside surface of the first ring member 1610 in the manner as described above with reference to FIGS. 36 and 37), engaging portion 1620 rides up the surface of a tooth 1630. As it does so, the base 1622 flexes at point 1626 to accommodate the height of the tooth until engaging portion 1620 falls between the next pair of neighbouring teeth 1630 on the first ring member. Since there is resilience in the flexing in the base 1622 at point 1626, and since there is frictional contact between the engaging portion 1620 and surface of the tooth 1630, a force that is greater than the frictional forces between engaging portion 1620 and tooth 1630 is required to enable the first ring member 1610 to rotate. This is achieved by the drive mechanism rotating the second ring member, which in turn drives the first ring member. The frictional forces, however, limit the free rotation of the first ring member in that the first ring member cannot freely rotate.

Thus a rotation of the second ring member 201, driven by the drive mechanism, can only cause the first ring member 1610 to rotate by one increment. Since the teeth 1630 are ratchet teeth or saw-tooth shaped-teeth, the angle of the slope on surface of the tooth 1630 in the reverse count direction is greater than the angle of the surface of the tooth 1630 in the forward count direction. As such, the steeper slope of the tooth 1630 abuts the engaging portion 1620 to prevent rotation of the first ring member in the reverse count direction.

In the embodiment shown, the pitch between teeth 1630 is half of the pitch between protrusions 1616 in the coupling mechanism between the second and first ring members. As such, for every protrusion 1616, the engaging portion 1620 moves two teeth 1630 forward. Of course, the skilled reader would appreciate that the pitch between teeth 1630 could be more or less than half of the pitch between protrusions 1616. For example, the pitch between teeth 1630 could be 1:1, or it could be even smaller, such as ⅓, ¼, ⅕.

The limiting mechanism 1606 may also comprise a guide in the form of an arm 1624, which projects from the base or panel 1622. The purpose of the arm 1624 is to keep the engaging portion 1620 in contact with the engaging portion teeth 1630 on the first ring member 1610. As such, the arm 1624 is arranged in a fixed relation to the engaging portion 1620 (i.e. it remains a fixed distance apart), and the arm contacts on the opposite surface of the first ring member 1610 to the engaging portion teeth 1630. In the embodiment shown in the figures, the arm 1624 therefore contacts the outer surface of the first ring member 1610. When in position, the first ring member therefore sits between the arm 1624 and the engaging portion 1620, as shown in FIGS. 43a to 43c.

By using a limiting mechanism 1606 that acts radially with respect to the first ring member, this alleviates the problems with manufacturing tolerances in the vertical direction. Instead of all of the manufacturing tolerances stacking up in the vertical direction, the only manufacturing tolerances that influence the operation of the limiting mechanism 1606 are those associated with the manufacturing of the limiting mechanism 1606 itself, and the radial dimensions of the first ring member 1610. As such, more reliable operation of the limiting mechanism is experienced.

Furthermore, by providing the guide arm 1624 at a fixed distance from the engaging portion 1620 on the base 1622 that may move radially due to the fixed, flexible end 1626, the engaging portion 1620 may more reliably track the first ring member, to ensure that the engaging portion 1620 remains in contact with the engaging portion teeth 1630 on the first ring member 1610. That is, movement of the first ring member 1610 in the radial direction (for example if there is some radial play between the first ring member and the limiting ring member) should not cause the engaging portion 1620 to disengage with the teeth 1630, since the arm 1624 will follow the movement of the first ring member or any contours that the first ring member may have (since it is in contact with the first ring member) when the first ring member moves radially outwards, and the engaging portion 1620 will follow movement of the first ring member when the first ring member moves radially inwardly.

In embodiments, the limiting ring member also comprises a plurality of locating recesses 1608a, 1608b and 1608c in the upper circumferential surface. Correspondingly-shaped protrusions locate within these recesses to hold the limiting ring member in place and therefore to prevent rotation of the limiting ring member. The protrusions may be located in a container or a dispenser (e.g. in a dispenser cap). By preventing the limiting ring member from rotation, this ensures that the deflector 1604 remains in a consistent position relative to the second and first ring members.

A plurality of corresponding-shaped protrusions located in a container or dispenser may be designed with an asymmetrical pattern to provide a keying function. That is, the limiting ring member will only locate in one rotational position relative to the container and dispenser, and therefore also the second and first ring members. This ensures that the limiting ring member is always located correctly with respect to the second and first ring members to allow the count to correctly register.

The first ring member 1610 may also comprises a display cover element 1614 for obscuring a view of the first indicia (as described above with reference to FIG. 38) to indicate that the counter has reached zero, indicating an empty dispenser.

Whilst the limiting mechanism 1606 has been described with reference to a two-ring counter mechanism (i.e. second, unit, ring member and first, tens, unit ring member), the limiting mechanism may instead be used with a single ring member counter mechanism (i.e. using only the second, units, ring). In such an embodiment, the second ring member would comprise the pawl mechanism as described above, but would not comprise the coupling arms 704. Furthermore, the limiting mechanism may also be used in a counter mechanism having more than two ring members, for example a three or four-ring counter mechanism.

Whilst the limiting mechanism has been described above with reference to a limiting ring member disposed co-axially with the first ring member, it is alternatively envisaged that a limiting mechanism may be provided that protrudes from a dispenser cap or canister within the dispenser i.e. that does not comprise a limiting ring member arranged co-axially with the first ring member. In this alternative configuration, the limiting mechanism 1606 must remain in fixed relation to the first ring member. As with the preferred embodiment described above, the alternative limiting mechanism also acts radially, and would comprise the engaging portion 1620 disposed on a base with a floating and fixed end, and having a guide arm as arranged above. In such an alternative embodiment, the deflector 1604 also would need to be arranged to protrude from the canister or dispense or dispenser cap and remain in a fixed position relative to the first ring member.

It will be apparent that the limiting ring member does not comprise indicia, and it is not intended to carry indicia, as this embodiment requires the limiting ring member to remain in a fixed rotational position relative to the second and first ring members for the count to indicate the correct remaining doses.

While the invention has been exemplified by the above description of specific embodiments, and uses thereof, the foregoing should not be considered by the reader as a limitation on the scope of the invention, which is defined in the appended claims.

The invention claimed is:

1. A dispenser for dispensing a dose of a gaseous, gas borne or droplet substance from a substance source, the dispenser comprising:
   a body for receiving the substance source, the body having a mouthpiece;
   a junction member slideably arranged in the body for movement in a longitudinal axis of the body to release a dose of the substance from the substance source, the junction member comprising a socket for receiving a spout of the substance source;
   a dispenser driver for moving the junction member in the longitudinal axis of the body to release a dose of the substance from the substance source, the dispenser driver comprising a pivot shaft and a cam arranged on the shaft, the dispenser driver being arranged within the body such that rotation of the pivot shaft causes the cam to rotate and apply a force to the junction member so as to move the junction member in the longitudinal axis;
   a cam follower slideably arranged within the body, the cam follower comprising a base and a substantially rigid protrusion extending from the base, the protrusion being arranged between the dispenser driver and the junction member such that a force applied by the cam of the dispenser driver to the protrusion causes the cam follower to slideably move in the longitudinal axis of the body and apply a force to the junction member so as to release a dose of the substance from the substance source;

a dispenser cap comprising a hollow body having a lower open end engageable with the body, and an upper open end for receiving a cap closure device for closing the upper open end, the upper open end comprising an engageable portion; and the cap closure device, comprising:

an upper cap closure portion for engaging with the upper open end of the dispenser cap to close the upper open end of the dispenser cap;

a lower cap closure portion for engaging with the engageable portion to secure the cap closure device to the dispenser cap; and a bistable portion connecting the upper cap closure portion and the lower cap closure portion, the bistable portion being switchable between a first stable form in which the bistable portion is extended, and a second stable form in which the bistable portion is collapsed, wherein, when the bistable portion is in the second stable form, the upper cap closure portion engages with the upper open end of the dispenser cap to close the dispenser cap;

a dose counter for indicating a number of actuations of the dispenser corresponding to a number of doses dispensed from the substance source, or a number of doses remaining in the substance source, the dose counter comprising:

a first ring member having a first indicia and being rotatable in increments about the longitudinal axis, the first indicia indicating a count; and a limiting member comprising a limiting mechanism, wherein the limiting mechanism comprises an engaging portion arranged to act radially with respect to the first ring member to contact the first ring member to limit free rotation of the first ring member relative to the limiting member about the axis.

2. A dispenser according to claim 1, wherein the limiting mechanism engaging portion comprises one or more teeth arranged to contact an inner circumferential surface of the first ring member.

3. A dispenser according to claim 1, wherein the first ring member comprises an engaging portion arranged to cooperate with the engaging portion of the limiting member to limit free rotation of the first ring member relative to the limiting member about the axis.

4. A dispenser according to claim 3, wherein the engaging portion on the first ring member comprises a plurality of teeth on an inner circumferential surface of the first ring member.

5. A dispenser according to claim 1, wherein the limiting mechanism comprises a guide, the guide comprising an arm spaced apart from the limiting member engaging portion in a fixed relation, the guide being configured to contact the first ring member such that the limiting member engaging portion maintains contact with the first ring member.

6. A dispenser according to claim 1, wherein the limiting mechanism is supported on a base having a fixed end and a floating end, the fixed end being coupled to the limiting member and the floating end being free of the limiting member, and wherein the base is flexible at the fixed end such that the floating end is moveable radically with respect to the first ring member.

7. A dispenser according to claim 1, wherein the limiting member comprises a limiting ring member coaxially arranged about the same axis as the first ring member.

8. A dispenser according to claim 1, wherein the limiting mechanism is configured to provide a frictional resistance to the first ring member in a forward count direction of the first ring member, and to prevent movement of the first ring member in a reverse count direction.

9. A dispenser according to claim 1, wherein the body comprises a guide for guiding the slideable motion of the cam follower base in the longitudinal axis, the guide being shaped to receive the base of the cam follower in a slideable engagement.

10. A dispenser according to claim 1, wherein the cam follower further comprises a resiliently deformable clip disposed on a lower edge of the base for engaging with a correspondingly shaped protrusion in the body, and wherein, when the clip is engaged with the protrusion, the cam follower is retained in the longitudinal position in the body until a force is exerted on the cam follower by the cam.

11. A dispenser according to claim 1, wherein the bistable portion of the cap closure device comprises:

a substantially rigid separator connected to the upper cap closure portion; and a resiliently deformable separator having first and second ends, the first end being connected to the substantially rigid separator via a resiliently deformable joint, and the second end being connected to the lower cap closure portion via a resiliently deformable joint, wherein the resiliently deformable separator is configured to resiliently deform upon application of a force to the upper cap closure portion and lower cap closure portion so as to permit a change of form of the dispenser cap closure device between the first stable form and second stable form.

12. A dispenser according to claim 1, wherein the lower cap closure portion comprises a plurality of protrusions extending radially outwards having an upper surface for engaging with the engageable portion of the dispenser cap, and wherein a lower surface of the lower cap closure portion is engageable with a surface of the substance source when received in the dispenser.

13. A dispenser according to claim 12, wherein the engageable portion of the dispenser cap comprises a ramped portion, and wherein the ramped portion and the protrusions on the lower cap closure portion are configured such that rotation of the cap closure device causes the upper surface of the plurality of protrusions to ride along the ramped portion so as to draw the cap closure device further into the dispenser cap.

14. A dispenser according to claim 13, wherein the ramped portion comprises a plurality of ramped portions around the circumference of a lip of the dispenser cap, the plurality of ramped portions equalling the number of plurality of protrusions on the lower cap portion of the cap closure device.

15. A dispenser according to claim 1, wherein an upper surface of the dispenser cap comprises a limiting means for preventing rotation of the cap closure device when in the second stable form.

16. A dispenser according to claim 1, wherein the dispenser cap comprises one or more protrusions in the upper open end of the dispenser cap, the one or more protrusions being arranged to engage with a correspondingly shaped recess in the upper cap closure portion when the dispenser cap is closed by the dispenser closure device.

17. A dispenser according to claim 1, further comprising a substance source.

18. A dispenser according to claim 2, wherein the one or more teeth of the limiting mechanism engaging portion comprises one or more triangular or ratchet-shaped teeth.

19. A dispenser according to claim 4, wherein the plurality of teeth on the inner circumferential surface of the first ring comprise ratchet teeth.

20. A dispenser according to claim 5, wherein the guide is configured to contact the first ring member on an outer circumferential surface.

21. A dispenser according to claim 6, wherein the limiting member engaging portion is located at the floating end of the base.

22. A dispenser according to claim 7, wherein the limiting ring member comprises one or more locating recesses disposed in an upper circumferential surface for engaging with correspondingly-shaped protrusions in the hollow body of the dispenser cap for preventing rotation of the limiting ring member about the axis.

23. A dispenser according to claim 9, wherein the guide comprises one or more guide rails arranged and adapted to co-operate with one or more guide rails on the cam follower base such that the cam follower is slideable within the body.

24. A dispenser according to claim 11, wherein an angle defined between an outer surface of the substantially rigid separator and the resiliently deformable separator is acute when in the second stable form, and obtuse when in the first stable form.

25. A dispenser according to claim 13, wherein, when the cap closure device is rotated, the riding of the upper surface of the protrusions along the ramped portion causes the lower surface of the lower cap closure portion to drive down onto the substance source when received in the dispenser.

26. A dispenser according to claim 14, wherein the ramped portions are separated from one and other by a gap having a width that is greater than or equal to the width of a protrusion on the lower cap closure portion.

27. A dispenser according to claim 15, wherein the limiting means comprises a plurality of teeth located on an upper surface of the dispenser cap, and wherein the dispenser cap closure device comprises a plurality of protrusions on a lower surface of the upper cap closure portion, the teeth and protrusions being configured to engage with one another so as to prevent rotation of the cap closure device when in the second stable form.

28. A dispenser according to claim 17, wherein the substance source is a pressurised metered-dose inhaler (pMDI).

29. A dispenser according to claim 1, further comprising a pivotally mounted closure for the mouthpiece, the closure being coupled to the dispenser driver such that pivoting of the cover causes rotation of the pivot shaft of the dispenser driver.

30. A dispenser according to claim 1, further comprising:
a breath actuatable valve incorporated with the junction member, for controlling the release of a gas and/or liquid comprising the substance, the valve comprising:
a flexible tube for receiving a dose of the substance, the tube extending from an inlet end connected to the junction member socket, having a location which is kinkable for closure of the valve in a ready position and moveable to a release position in which the tube is un-kinked for opening of the valve, and having an outlet end moveable for kinking/un-kinking of the tube; and
an outlet member carrying the outlet end of the flexible tube and pivotally connected to the junction member for control of kinking/un-kinking movement of the flexible tube;
the tube being kinked to an obturating extent when the pivotal outlet member is in a ready position and un-kinked when the pivotal outlet member is moved to a release position.

31. A dispenser according to claim 30, further comprising:
a sear on the outlet member to hold the outlet member in the ready position prior to inhalation;
a breath actuatable flap carried on the junction member and arranged for action of inhalation breath on it, the flap having:
a latch complementary to the sear;
the flap being arranged:
to releasably receive the pivotal outlet member for kinked closure of the flexible tube by cooperation of the latch and the sear and
to release the pivotal outlet member for un-kinking of the tube, and substance release, on inhalation, by release of the sear from the latch and movement to the release position of the outlet member.

32. A dispenser according to claim 1, comprising:
a second ring member having second indicia, the second ring member being rotatable in increments about the same axis as the first ring member, the second indicia indicating a count;
a coupling mechanism for releasably coupling the second ring member to the first ring member, to allow the second and first ring members to rotate cooperatively when coupled and to allow independent rotating of the second ring member when not coupled;
wherein the coupling mechanism comprises first and second engagement means, the first engagement means being movable radially outwardly and radially inwardly relative to the axis.

33. A dispenser according to claim 32 wherein the coupling mechanism comprises a deflector to deflect the first engagement means radially outwardly.

34. A dispenser according to claim 33 wherein the first engagement means is deflected radially outwardly after a predetermined degree of rotation of the second ring member, the predetermined amount of rotation of the second ring member being less than a full rotation of the second ring member about the axis.

35. A dispenser according to claim 33 wherein the first engagement means comprises an arm having a slot and a contact end.

36. A dispenser according to claim 33, wherein the deflector is connected to, or integral with the limiting member.

37. A dispenser for dispensing a dose of a gaseous, gas borne or droplet substance from a substance source, the dispenser comprising:
a body for receiving the substance source, the body having a mouthpiece;
a junction member slideably arranged in the body for movement in a longitudinal axis of the body to release a dose of the substance from the substance source, the junction member comprising a socket for receiving a spout of the substance source;
a dispenser driver for moving the junction member in the longitudinal axis of the body to release a dose of the substance from the substance source, the dispenser driver comprising a pivot shaft and a cam arranged on the shaft, the dispenser driver being arranged within the body such that rotation of the pivot shaft causes the cam to rotate and apply a force to the junction member so as to move the junction member in the longitudinal axis;

a cam follower slideably arranged within the body, the cam follower comprising a base and a substantially rigid protrusion extending from the base, the protrusion being arranged between the dispenser driver and the junction member such that a force applied by the cam of the dispenser driver to the protrusion causes the cam follower to slideably move in the longitudinal axis of the body and apply a force to the junction member so as to release a dose of the substance from the substance source;

a dispenser cap comprising a hollow body having a lower open end engageable with the body, and an upper open end for receiving a cap closure device for closing the upper open end, the upper open end comprising an engageable portion; and the cap closure device, comprising:

an upper cap closure portion for engaging with the upper open end of the dispenser cap to close the upper open end of the dispenser cap;

a lower cap closure portion for engaging with the engageable portion to secure the cap closure device to the dispenser cap; and a bistable portion connecting the upper cap closure portion and the lower cap closure portion, the bistable portion being switchable between a first stable form in which the bistable portion is extended, and a second stable form in which the bistable portion is collapsed, wherein, when the bistable portion is in the second stable form, the upper cap closure portion engages with the upper open end of the dispenser cap to close the dispenser cap.

38. A dispenser according to claim 37, further comprising a dose counter for indicating a number of actuations of the dispenser corresponding to a number of doses dispensed from the substance source, or a number of doses remaining in the substance source.

39. A dispenser according to claim 38, wherein the dispenser counter comprises:

a first ring member having a first indicia and being rotatable in increments about the longitudinal axis, the first indicia indicating a count;

a second ring member having second indicia, the second ring member being rotatable in increments about the same axis as the first ring member, the second indicia indicating a count;

a coupling mechanism for releasably coupling the second ring member to the first ring member, to allow the second and first ring members to rotate cooperatively when coupled and to allow independent rotating of the second ring member when not coupled;

wherein the coupling mechanism comprises first and second engagement means, the first engagement means being movable radially outwardly and radially inwardly relative to the axis.

40. A dispenser according to claim 39, comprising:

a limiting member comprising a limiting mechanism, wherein the limiting mechanism limits free rotation of the first ring member relative to the limiting member about the axis.

41. A dispenser according to claim 40, comprising a drive mechanism for rotating the second ring member, and wherein at least part of the drive mechanism is integral with the second ring member.

42. A dispenser according to claim 41, wherein the drive mechanism comprises a pawl-and-teeth mechanism.

43. A dispenser according to claim 41, wherein the pawl-and-teeth mechanism comprises:

a first and second pawl engageable with a plurality of teeth, and wherein each of the first and second pawls comprise a driving engagement face for engaging in a driving engagement with one of the plurality of teeth, and a sliding engagement face for sliding over one of the plurality of teeth.

44. A dispenser according to claim 43, wherein each of the first and second pawls is arranged such that:

the second pawl rides over one of the plurality of teeth during a count stroke of the drive mechanism, and the first pawl rides over one of the plurality of teeth during a return stroke of the drive mechanism.

45. A dispenser according to claim 43, wherein the first and second pawls are integral with the second ring member, and the plurality of teeth are disposed on a counter driver, the counter driver being coupleable to the junction member and arranged to be reciprocally moveable within a bore of the second ring member, and wherein the pawl-and-teeth mechanism is configured such that reciprocal movement of the counter driver within the bore of the second ring member causes rotational movement of the second ring member.

46. A dispenser according to claim 45, wherein the body comprises a counter driver guide configured to guide the counter driver in the body so as to prevent rotation of the counter driver in the longitudinal axis.

47. A dispenser according to claim 45, wherein the junction member comprises one or more slots, and the counter driver comprises one or more protrusions for engaging with the junction member so as to couple the junction member and counter driver.

48. A dispenser according to claim 43, wherein each of the first and second pawls is arranged such that:

the first pawl engages in a driving engagement with one of the plurality of teeth during a count stroke of the drive mechanism, and the second pawl engages in a driving engagement with one of the plurality of teeth during a return stroke of the drive mechanism.

49. A dispenser according to claim 45, wherein the drive mechanism comprises third and fourth pawls engageable with the plurality of teeth, the third and fourth pawls being integral with the first ring member on a surface radially opposing the first and second pawls.

50. A dispenser according to claim 46, wherein the counter driver guide comprises a protrusion extending from the body, the protrusion being configured and shaped so as to co-operate with a correspondingly shaped notch in the counter driver.

51. A dispenser for dispensing a dose of a gaseous, gas borne or droplet substance from a substance source, the dispenser comprising:

a body for receiving the substance source, the body having a mouthpiece;

a junction member slideably arranged in the body for movement in a longitudinal axis of the body to release a dose of the substance from the substance source, the junction member comprising a socket for receiving a spout of the substance source;

a dispenser driver for moving the junction member in the longitudinal axis of the body to release a dose of the substance from the substance source, the dispenser driver comprising a pivot shaft and a cam arranged on the shaft, the dispenser driver being arranged within the body such that rotation of the pivot shaft causes the cam to rotate and apply a force to the junction member so as to move the junction member in the longitudinal axis;
a cam follower slideably arranged within the body, the cam follower comprising a base and a substantially rigid protrusion extending from the base, the protrusion being arranged between the dispenser driver and the junction member such that a force applied by the cam of the dispenser driver to the protrusion causes the cam follower to slideably move in the longitudinal axis of the body and apply a force to the junction member so as to release a dose of the substance from the substance source;
a dose counter for indicating a number of actuations of the dispenser corresponding to a number of doses dispensed from the substance source, or a number of doses remaining in the substance source, the dose counter comprising:
a first ring member having a first indicia and being rotatable in increments about an axis, the first indicia indicating a count; and
a limiting member comprising a limiting mechanism,
wherein the limiting mechanism comprises an engaging portion arranged to act radially with respect to the first ring member to contact the first ring member to limit free rotation of the first ring member relative to the limiting member about the axis.

52. A dispenser according to claim 51, said limiting mechanism engaging portion comprising one or more teeth arranged to contact an inner circumferential surface of the first ring member,
and/or the body comprises a guide for guiding the slideable motion of the cam follower base in the longitudinal axis, the guide being shaped to receive the base of the cam follower in a slideable engagement,
and/or the cam follower further comprises a resiliently deformable clip disposed on a lower edge of the base for engaging with a correspondingly shaped protrusion in the body, and wherein, when the clip is engaged with the protrusion, the cam follower is retained in the longitudinal position in the body until a force is exerted on the cam follower by the cam.

53. A dispenser according to claim 52, wherein the one or more teeth of said limiting mechanism engaging portion comprise one or more triangular or ratchet-shaped teeth.

54. A dispenser according to claim 52, wherein the guide comprises one or more guide rails arranged and adapted to co-operate with one or more guide rails on the cam follower base such that the cam follower is slideable within the body.

55. A dispenser for dispensing a dose of a gaseous, gas borne or droplet substance from a substance source, the dispenser comprising:
a body for receiving the substance source, the body having a mouthpiece;
a dispenser cap comprising a hollow body having a lower open end engageable with the body, and an upper open end for receiving a cap closure device for closing the upper open end, the upper open end comprising an engageable portion; and
the cap closure device, comprising:
an upper cap closure portion for engaging with the upper open end of the dispenser cap to close the upper open end of the dispenser cap;
a lower cap closure portion for engaging with the engageable portion to secure the cap closure device to the dispenser cap; and
a bistable portion connecting the upper cap closure portion and the lower cap closure portion, the bistable portion being switchable between a first stable form in which the bistable portion is extended, and a second stable form in which the bistable portion is collapsed,
wherein, when the bistable portion is in the second stable form, the upper cap closure portion engages with the upper open end of the dispenser cap to close the dispenser cap;
a dose counter for indicating a number of actuations of the dispenser corresponding to a number of doses dispensed from the substance source, or a number of doses remaining in the substance source, the dose counter comprising:
a first ring member having a first indicia and being rotatable in increments about an axis, the first indicia indicating a count; and
a limiting member comprising a limiting mechanism,
wherein the limiting mechanism comprises an engaging portion arranged to act radially with respect to the first ring member to contact the first ring member to limit free rotation of the first ring member relative to the limiting member about the axis.

56. A dispenser according to claim 55, said limiting mechanism engaging portion comprising one or more teeth arranged to contact an inner circumferential surface of the first ring member,
and/or the bistable portion of the cap closure device comprises:
a substantially rigid separator connected to the upper cap closure portion; and
a resiliently deformable separator having first and second ends, the first end being connected to the substantially rigid separator via a resiliently deformable joint, and the second end being connected to the lower cap closure portion via a resiliently deformable joint,
wherein the resiliently deformable separator is configured to resiliently deform upon application of a force to the upper cap closure portion and lower cap closure portion so as to permit a change of form of the dispenser cap closure device between the first stable form and second stable form,
and/or the lower cap closure portion comprises a plurality of protrusions extending radially outwards having an upper surface for engaging with the engageable portion of the dispenser cap, and a lower surface of the lower cap closure portion is engageable with a surface of the substance source when received in the dispenser, the engageable portion of the dispenser cap comprising a ramped portion, and the ramped portion and the protrusions on the lower cap closure portion are configured such that rotation of the cap closure device causes the upper surface of the plurality of protrusions to ride along the ramped portion so as to draw the cap closure device further into the dispenser cap.

57. A dispenser according to claim 56, wherein the one or more teeth of the limiting mechanism engaging portion comprise one or more triangular or ratchet-shaped teeth.

58. A dispenser according to claim 56, wherein an angle defined between an outer surface of the substantially rigid separator and the resiliently deformable separator is acute when in the second stable form, and obtuse when in the first stable form.

59. A dispenser according to claim 56, wherein, when the cap closure device is rotated, the riding of the upper surface of the protrusions along the ramped portion causes the lower surface of the lower cap closure portion to drive down onto the substance source when received in the dispenser.

\* \* \* \* \*